(12) United States Patent
Buhimschi et al.

(10) Patent No.: US 11,953,505 B2
(45) Date of Patent: Apr. 9, 2024

(54) METHODS AND COMPOSITIONS FOR DETECTING MISFOLDED PROTEINS

(71) Applicant: Yale University, New Haven, CT (US)

(72) Inventors: Irina Buhimschi, Columbus, OH (US); Catalin S. Buhimschi, Columbus, OH (US); Michael Choma, Hamden, CT (US); Hemant Tagare, North Haven, CT (US); Stephan Michael Jonas, Alsdorf (DE)

(73) Assignee: Yale University, New Haven, CT (US)

( * ) Notice: Subject to any disclaimer, the term of this patent is extended or adjusted under 35 U.S.C. 154(b) by 113 days.

(21) Appl. No.: 17/361,967

(22) Filed: Jun. 29, 2021

(65) Prior Publication Data

US 2022/0043001 A1 Feb. 10, 2022

Related U.S. Application Data

(60) Continuation of application No. 16/406,942, filed on May 8, 2019, now Pat. No. 11,079,392, which is a
(Continued)

(51) Int. Cl.
*G01N 33/52* (2006.01)
*C09B 69/10* (2006.01)
(Continued)

(52) U.S. Cl.
CPC ........... *G01N 33/689* (2013.01); *G01N 33/52* (2013.01); *G01N 33/6839* (2013.01);
(Continued)

(58) Field of Classification Search
CPC .. G01N 33/689; G01N 33/52; G01N 33/6839; G01N 21/78; G01N 2800/368; G01N 33/68; C09B 69/106
See application file for complete search history.

(56) References Cited

U.S. PATENT DOCUMENTS

| 4,444,879 A | 4/1984 | Foster et al. |
| 5,998,216 A | 12/1999 | O'Donnell |

(Continued)

FOREIGN PATENT DOCUMENTS

| CN | 102483418 A | 5/2012 |
| CN | 103012599 A | 4/2013 |

(Continued)

OTHER PUBLICATIONS

International Search Report and Written Opinion for International Application No. PCT/US2009/005957 dated May 26, 2010.
(Continued)

*Primary Examiner* — Jennifer Wecker
*Assistant Examiner* — Ali Husain Faraz
(74) *Attorney, Agent, or Firm* — Wolf, Greenfield & Sacks, P.C.

(57) ABSTRACT

Various aspects and embodiments of the present disclosure are directed to methods and compositions (e.g., kits) for the identification of subjects with misfolded proteins in their urine. For example, methods and compositions for determining that a urine sample from a pregnant woman contains or does not contain misfolded are provided. In some embodiments, the presence of misfolded proteins in a urine sample from a pregnant woman is an indication of preeclampsia.

20 Claims, 44 Drawing Sheets

Specification includes a Sequence Listing.

Related U.S. Application Data division of application No. 14/683,908, filed on Apr. 10, 2015, now Pat. No. 10,324,094.

(60) Provisional application No. 61/978,158, filed on Apr. 10, 2014.

(51) Int. Cl.
*G01N 33/68* (2006.01)
*G01N 21/78* (2006.01)

(52) U.S. Cl.
CPC ............ *C09B 69/106* (2013.01); *G01N 21/78* (2013.01); *G01N 2800/368* (2013.01)

(56) References Cited

U.S. PATENT DOCUMENTS

| | | |
|---|---|---|
| 6,444,435 B1 | 9/2002 | Christner |
| 7,727,733 B2 | 6/2010 | Buhimschi et al. |
| 7,935,496 B2 | 5/2011 | Buhimschi et al. |
| 8,263,342 B2 | 9/2012 | Buhimschi et al. |
| 9,229,009 B2 | 1/2016 | Buhimschi et al. |
| 10,048,276 B2 | 8/2018 | Buhimschi et al. |
| 10,324,094 B2 | 6/2019 | Buhimschi et al. |
| 11,079,392 B2 | 8/2021 | Buhimschi et al. |
| 2005/0051052 A1 | 3/2005 | Vanmaele et al. |
| 2011/0065139 A1 | 3/2011 | Mullerad et al. |
| 2011/0280863 A1* | 11/2011 | Buhimschi ......... G01N 33/6866 436/501 |
| 2015/0293115 A1 | 10/2015 | Buhimschi et al. |
| 2016/0097775 A1 | 4/2016 | Buhimschi et al. |
| 2017/0356920 A1 | 12/2017 | Buhimschi et al. |
| 2019/0353662 A1 | 11/2019 | Buhimschi et al. |
| 2022/0043001 A1 | 2/2022 | Buhimschi et al. |

FOREIGN PATENT DOCUMENTS

| | | |
|---|---|---|
| EP | 1 733 762 A1 | 12/2006 |
| JP | 2002-172162 A | 6/2002 |
| WO | WO 92/017769 A1 | 10/1992 |
| WO | WO 1998/028006 A1 | 7/1998 |
| WO | WO 2004/008946 A2 | 1/2004 |
| WO | WO 2004/024090 A2 | 3/2004 |
| WO | WO 2007/051069 A2 | 5/2007 |
| WO | WO 2007/053161 A2 | 5/2007 |
| WO | WO 2010/062377 A | 6/2010 |
| WO | WO 2015/157704 A | 10/2015 |

OTHER PUBLICATIONS

International Preliminary Report on Patentability for International Application No. PCT/US2009/005957 dated May 12, 2011.
International Search Report and Written Opinion for International Application No. PCT/US2015/025432 dated Mar. 15, 2016.
International Preliminary Report on Patentability for International Application No. PCT/US2015/025432 dated Oct. 20, 2016.
Extended European Search Report for EP Application No. EP 20168843.9 dated Oct. 30, 2020.
Abou-Zahr et al., Antenatal care in developing countries: promises, achievements and missed opportunities: an analysis of trends, levels and differentials, 1990-2001. World Health Organization, Geneva, Switzerland, 2003. 36 pages.
Acog Committee On Obstetric Practice. Acog practice bulletin. Diagnosis and management of preeclampsia and eclampsia. No. 33, Jan. 2002. American College of Obstetricians and Gynecologists. Int J Gynaecol Obstet. Apr. 2002;77(1):67-75.
Buhimschi et al., 239: Preeclampsia is a disease characterized by specific supramolecular aggregates of misfolded proteins and congophilia. American Journal of Obstetrics & Gynecology. 2008;199(6):S78 Abstract Only.
Buhimschi et al., Protein misfolding, congophilia, oligomerization, and defective amyloid processing in preeclampsia. Sci Transl Med. Jul. 16, 2014;6(245):245ra92. doi: 10.1126/scitranslmed.3008808.
Buhimschi et al., Proteomic profiling of urine identifies specific fragments of SERPINA1 and albumin as biomarkers of preeclampsia. Am J Obstet Gynecol. Nov. 2008;199(5):551.e1-16. doi: 10.1016/j.ajog.2008.07.006.
Buhimschi et al., The nitric oxide pathway in pre-eclampsia: pathophysiological implications. Hum Reprod Update. Jan.-Feb. 1998;4(1):25-42. Review.
Buhimschi et al., Urinary angiogenic factors cluster hypertensive disorders and identify women with severe preeclampsia. Am J Obstet Gynecol. Mar. 2005;192(3):734-41.
Calbiochem General Catalog (2002-2003), catalog #234610, p. 180.
Carrell et al., Alpha1-antitrypsin deficiency—a model for conformational diseases. N Engl J Med. Jan. 3, 2002;346(1):45-53. Review.
Chang et al., Identification of a 4-mer peptide inhibitor that effectively blocks the polymerization of pathogenic Z alpha1-antitrypsin. Am J Respir Cell Mol Biol. Nov. 2006;35(5):540-8. Epub Jun. 15, 2006.
Davis et al., Supramolecular assembly dynamics. Proc Natl Acad Sci U S A. Apr. 16, 2002;99(8):4793-6. Epub Mar. 5, 2002.
Devlin et al., Prevention of polymerization of M and Z alpha1-Antitrypsin (alpha1-AT) with trimethylamine N-oxide. Implications for the treatment of alpha1-at deficiency. Am J Respir Cell Mol Biol. Jun. 2001;24(6):727-32.
Eiland et al., Preeclampsia 2012. J Pregnancy. 2012;2012:586578. doi: 10.1155/2012/586578. Epub Jul. 11, 2012. Review.
Engel et al., Remote real-time monitoring of free flaps via smartphone photography and 3G wireless Internet: a prospective study evidencing diagnostic accuracy. Microsurgery. Nov. 2011;31(8):589-95. doi: 10.1002/micr.20921. Epub Aug. 24, 2011.
Faas et al., A new animal model for human preeclampsia: ultra-low-dose endotoxin infusion in pregnant rats. Am J Obstet Gynecol. Jul. 1994; 171(1):158-64.
Frid et al., Congo red and protein aggregation in neurodegenerative diseases. Brain Res Rev. Jan. 2007;53(1):135-60. Epub Sep. 7, 2006. Review.
Halimi et al., Prion urine comprises a glycosaminoglycan-light chain IgG complex that can be stained by Congo red. J Virol Methods. May 2006;133(2):205-10. Epub Jan. 4, 2006.
Harlow et al., The diversity of diagnoses of preeclampsia. Hypertens Pregnancy. 2001;20(1):57-67. Review.
Hinberg et al., Sensitivity of in vitro diagnostic dipstick tests to urinary protein. Clin Biochem. Apr. 1978;11(2):62-4.
Howie et al., Optical properties of amyloid stained by Congo red: history and mechanisms. Micron. Apr. 2009;40(3):285-301. doi:10. 1016/j.micron.2008.10.002. Epub Oct. 15, 2008. Review.
Hrncic et al., Antibody-mediated resolution of light chain-associated amyloid deposits. Am J Pathol. Oct. 2000; 157(4):1239-46.
Ikonomovic et al., X-34 labeling of abnormal protein aggregates during the progression of Alzheimer's disease. Methods Enzymol. 2006;412:123-44. Review.
Jonathan et al., Investigating a smartphone imaging unit for photoplethysmography. Physiol Meas. Nov. 2010;31(11):N79-83. doi: 10.1088/0967-3334/31/11/N01. Epub Sep. 24, 2010.
Joundi et al., Rapid tremor frequency assessment with the iPhone accelerometer. Parkinsonism Relat Disord. May 2011;17(4):288-90. doi: 10.1016/j.parkreldis.2011.01.001. Epub Feb. 5, 2011.
Kayed et al., Annular protofibrils are a structurally and functionally distinct type of amyloid oligomer. J Biol Chem. Feb. 13, 2009;284(7):4230-7. doi: 10.1074/jbc.M808591200. Epub Dec. 18, 2008.
Kayed et al., Common structure of soluble amyloid oligomers implies common mechanism of pathogenesis. Science. Apr. 18, 2003;300(5618):486-9.
Kayed et al., Conformation-dependent anti-amyloid oligomer antibodies. Methods Enzymol. 2006;413:326-44.
Kayed et al., Fibril specific, conformation dependent antibodies recognize a generic epitope common to amyloid fibrils and fibrillar oligomers that is absent in prefibrillar oligomers. Mol Neurodegener. Sep. 26, 2007;2:18.
Khan et al., WHO analysis of causes of maternal death: a systematic review. Lancet. Apr. 1, 2006;367(9516):1066-74. Review.

(56) References Cited

OTHER PUBLICATIONS

Klunk et al., Quantifying amyloid beta-peptide (Abeta) aggregation using the Congo red-Abeta (CR-abeta) spectrophotometric assay. Anal Biochem. Jan. 1, 1999;266(1):66-76.
Lehn, Toward self-organization and complex matter. Science. Mar. 29, 2002;295(5564):2400-3.
Lehn, Supramolecular Chemistry—Scope and Perspectives. Molecules—Supermolecules—Molecular Devices. Nobel lecture, Dec. 8, 1987. 48 pages.
Lemoyne et al., Implementation of an iPhone as a wireless accelerometer for quantifying gait characteristics. Conf Proc IEEE Eng Med Biol Soc. 2010;2010:3847-51. doi: 10.1109/IEMBS.2010.5627699.
Lemoyne et al., Implementation of an iPhone for characterizing Parkinson's disease tremor through a wireless accelerometer application. Conf Proc IEEE Eng Med Biol Soc. 2010;2010:4954-8. doi: 10.1109/IEMBS.2010.5627240.
Levine et al., Circulating angiogenic factors and the risk of preeclampsia. N Engl J Med. Feb. 12, 2004;350(7):672-83. Epub Feb. 5, 2004.
Levine, Urinary placental growth factor and risk of preeclampsia. JAMA. Jan. 5, 2005;293(1):77-85.
Levites et al., Anti-Abeta42- and anti-Abeta40-specific mAbs attenuate amyloid deposition in an Alzheimer disease mouse model. J Clin Invest. Jan. 2006; 116(1):193-201. Epub Dec. 8, 2005.
Linke, Highly sensitive diagnosis of amyloid and various amyloid syndromes using Congo red fluorescence. Virchows Arch. May 2000;436(5):439-48.
Lomas et al., Alpha1-antitrypsin polymerization and the serpinopathies: pathobiology and prospects for therapy. J Clin Invest. Dec. 2002;110(11):1585-90. Review.
Maisnar et al., The problems of proteinuria measurement in urine with presence of Bence Jones protein. Clin Biochem. Apr. 2011;44(5-6):403-5. doi: 10.1016/j.clinbiochem.2011.01.008. Epub Feb. 1, 2011.
Maynard, et al., Excess placental soluble fms-like tyrosine kinase 1 (sFlt1) may contribute to endothelial dysfunction, hypertension, and proteinuria in preeclampsia. J Clin Invest. Mar. 2003;111(5):649-58.
Murray et al., The clinical utility of routine urinalysis in pregnancy: a prospective study. Med J Aust. Nov. 4, 2002;177(9):477-80.
Oliver et al., Activation of the receptor for advanced glycation end products system in women with severe preeclampsia. J Clin Endocrinol Metab. Mar. 2011;96(3):689-98. doi: 10.1210/jc.2010-1418. Epub Feb. 16, 2011.
O'Nuallain et al., Conformational Abs recognizing a generic amyloid fibril epitope. Proc Natl Acad Sci U S A. Feb. 5, 2002;99(3): 1485-90. Epub Jan. 29, 2002.
Oresko et al., A wearable smartphone-based platform for real-time cardiovascular disease detection via electrocardiogram processing. IEEE Trans Inf Technol Biomed. May 2010;14(3):734-40. doi: 10.1109/TITB.2010.2047865. Epub Apr. 12, 2010.
Ozdalga et al., The smartphone in medicine: a review of current and potential use among physicians and students. J Med Internet Res. Sep. 27, 2012;14(5):e128. Review.
Paas Magical Color Cups (2005). 1 page.
Publications Committee, Society for Maternal-Fetal Medicine et al., Evaluation and management of severe preeclampsia before 34 weeks' gestation. Am J Obstet Gynecol. Sep. 2011;205(3):191-8. doi: 10.1016/j.ajog.2011.07.017. Epub Jul. 20, 2011. Review.
Roberts et al., Pre-eclampsia: more than pregnancy-induced hypertension. Lancet. Jun. 5, 1993;341(8858): 1447-51. Erratum in: Lancet Aug. 21, 1993;342(8869):504.
Ruano-Lopez et al., The SmartBioPhone, a point of care vision under development through two European projects: OPTOLABCARD and LABONFOIL. Lab Chip. Jun. 7, 2009;9(11):1495- 9. doi: 10.1039/b902354m. Epub Mar. 10, 2009.
Rybarska et al., Evidence that supramolecular Congo red is the sole ligation form of this dye for L chain lambda derived amyloid proteins. Folia Histochem Cytobiol. 2001;39(4):307-14.
Rybarska et al., In vivo accumulation of self-assembling dye Congo red in an area marked by specific immune complexes: possible relevance to chemotherapy. Folia Histochem Cytobiol. 2004;42(2):101-10.
Simon K. [Mechanism of reaction of Congo red with protein in filter paper]. Med Monatsschr. Nov. 1953;7(11):714-5.
Stopa et al., Effect of self association of bis-ANS and bis-azo dyes on protein binding. Biochimie. 1997;79(1):23-6.
Styren et al., X-34, a fluorescent derivative of Congo Red: A novel histochemical stain for Alzheimer's disease pathology. J of Histochem and Cytochem. 2000 48(9):1223-32.
Talaga, Inhibitors of beta-amyloid aggregation: still an issue of structure and function? Drug Discovery Today: Therapeutic Strategies. Sep. 2004;1(1):7-12.
Tang et al., Decreased levels of folate receptor-β and reduced numbers of fetal macrophages (Hofbauer cells) in placentas from pregnancies with severe pre-eclampsia. Am J Reprod Immunol. Aug. 2013;70(2):104-15. doi: 10.1111/aji.12112. Epub Mar. 11, 2013.
Thangaratinam et al., Estimation of proteinuria as a predictor of complications of pre-eclampsia: a systematic review. BMC Med. Mar. 24, 2009;7:10. doi: 10.1186/1741-7015-7-10. Review.
Vieira et al., Small molecule inhibitors of lysozyme amyloid aggregation. Cell Biochem Biophys. 2006;44(3):549-53.
Wallukat et al., Patients with preeclampsia develop agonistic autoantibodies against the angiotensin AT1 receptor. J Clin Invest. Apr. 1999; 103(7):945-52.
Ward et al., A molecular variant of angiotensinogen associated with preeclampsia. Nat Genet. May 1993;4(1):59-61.
Wolf et al., Diagnostic inaccuracy of smartphone applications for melanoma detection. JAMA Dermatol. Apr. 2013;149(4):422-6. doi: 10.1001/jamadermatol.2013.2382.
Wu et al., Dual binding modes of Congo red to amyloid protofibril surface observed in molecular dynamics simulations. J Am Chem Soc. Feb. 7, 2007;129(5):1225-32.
Zhang et al., Maternal vasculopathy and histologic diagnosis of preeclampsia: poor correlation of histologic changes and clinical manifestation. Am J Obstet Gynecol. Apr. 2006;194(4): 1050-6.

* cited by examiner

Characteristics

Case 1: CRR 125%
sPE, 30w =>MIED

Case 2: CRR 44%
PE?, 36w => MIED

Case 3: CRR 0%
P-CRL, 28w =>TD

FIGS. 3A-3C
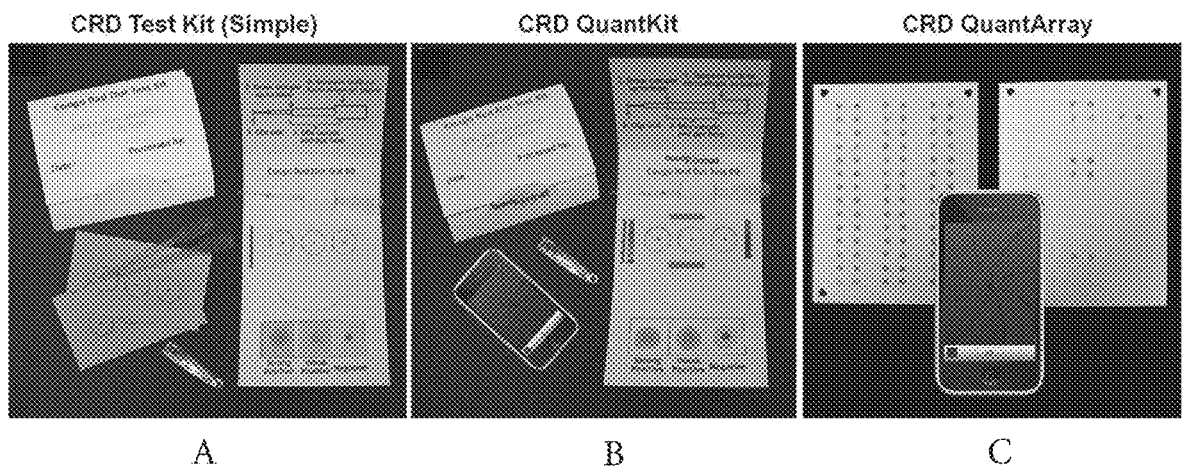
A        B        C
FIG. 4
1. Array preparation     2. Acquisition of images
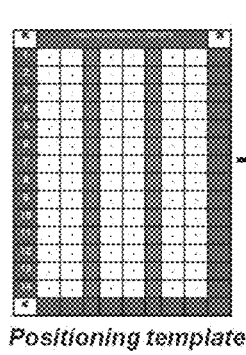
*Positioning template*
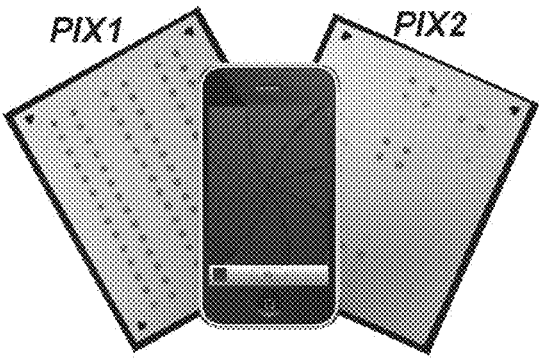
3. Image processing     4. CRR calculation
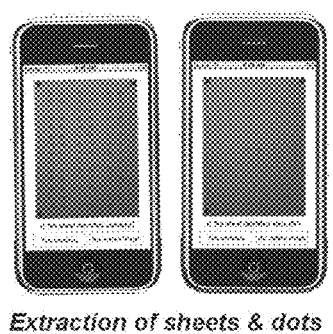
*Extraction of sheets & dots*
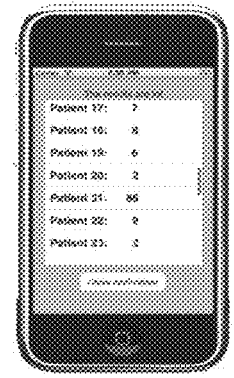

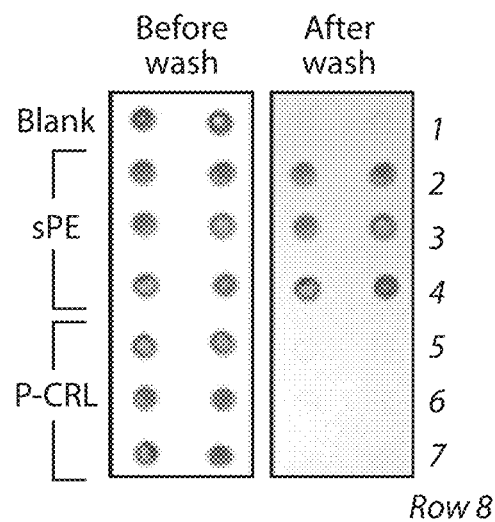
FIG. 6A
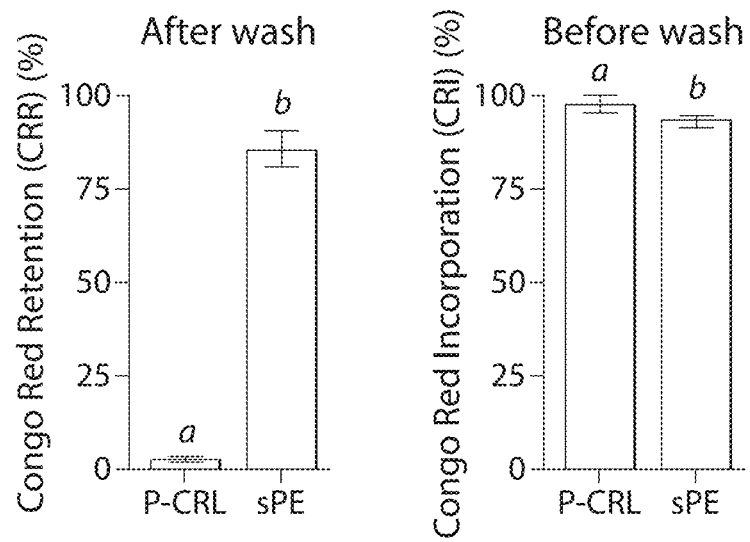
FIG. 6B
FIG. 6C

```
MRQKAVSLFLCYLLLFTCSGVEA----------GKKKCSESSDSGSGFWKALTFMAVGGGLA    52  P09912 Isoform A  IFI6_HUMAN
MRQKAVSLFLCYLLLFTCSGVEAGENA------GKKKCSESSDSGSGFWKALTFMAVGGGLA    56  P09912 Isoform B  IFI6_HUMAN
MRQKAVSLFLCYLLLFTCSGVEAGENAGKDAGKKKCSESSDSGSGFWKALTFMAVGGGLA      60  P09912 Isoform C  IFI6_HUMAN
***********************    ****************************

VAGLPALGFTGAGIAANSVAASLMSWSAILNGGGVPAGGLVATLQSLGAGGSSVVIGNIG    112  P09912 Isoform A  IFI6_HUMAN
VAGLPALGFTGAGIAANSVAASLMSWSAILNGGGVPAGGLVATLQSLGAGGSSVVIGNIG    116  P09912 Isoform B  IFI6_HUMAN
VAGLPALGFTGAGIAANSVAASLMSWSAILNGGGVPAGGLVATLQSLGAGGSSVVIGNIG    120  P09912 Isoform C  IFI6_HUMAN
************************************************************

ALMGYATHKYLDSEEDEE    130  P09912 Isoform A  IFI6_HUMAN
ALMGYATHKYLDSEEDEE    134  P09912 Isoform B  IFI6_HUMAN
ALMGYATHKYLDSEEDEE    138  P09912 Isoform C  IFI6_HUMAN
```

Back

Inside

Red Dot (CRD) Quant Kit

Affix identifier
bar code here

Date:                Processed by:

FIGS. 27A-27B
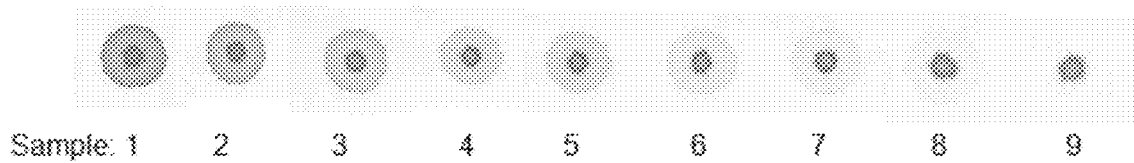
(a) Diffusion of normal urine drops (increasing CR/food dye ratio from left to right).
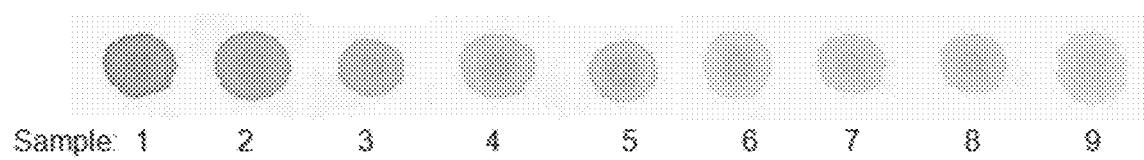
(b) Diffusion of pre-eclamptic urine drops (increasing CR/food dye ratio from left to right in the same ratio as (a) above).
FIG. 28
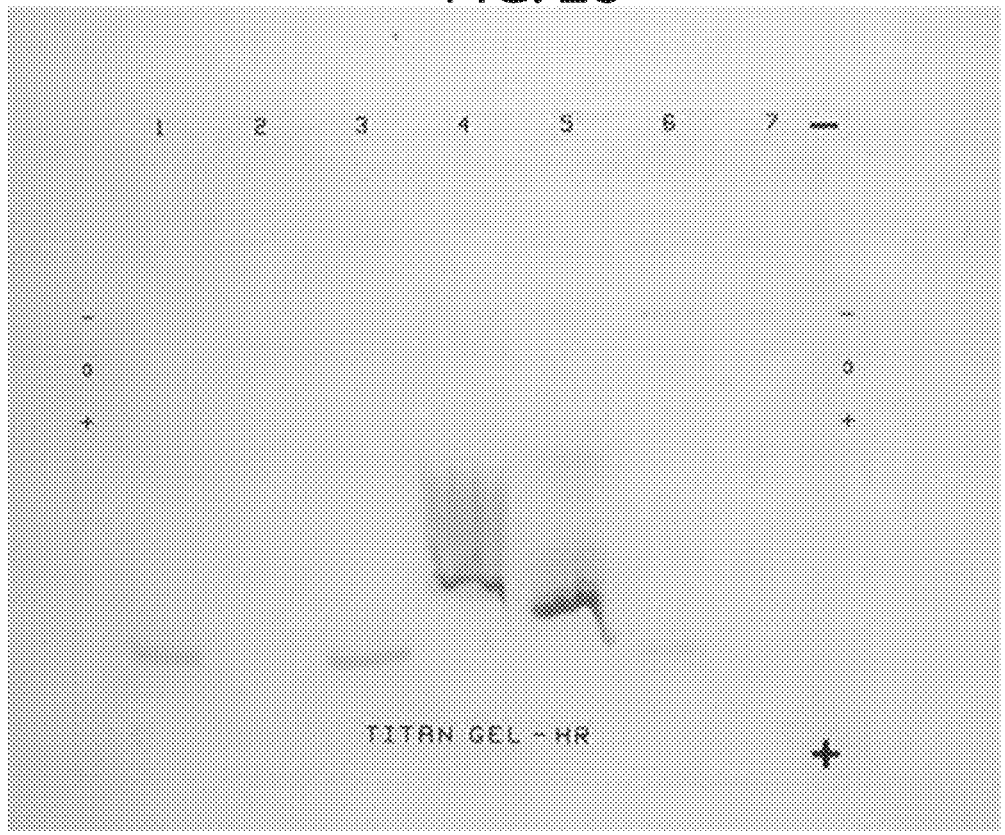

SEQUENCE LISTING

<160> NUMBER OF SEQ ID NOS: 6

<210> SEQ ID NO 1
<211> LENGTH: 130
<212> TYPE: PRT
<213> ORGANISM: Artificial Sequence
<220> FEATURE:
<223> OTHER INFORMATION: Synthetic Polypeptide

<400> SEQUENCE: 1

Met Arg Gln Lys Ala Val Ser Leu Phe Leu Cys Tyr Leu Leu Leu Phe
1               5                   10                  15

Thr Cys Ser Gly Val Glu Ala Gly Lys Lys Cys Ser Glu Ser Ser
            20                  25                  30

Asp Ser Gly Ser Gly Phe Trp Lys Ala Leu Thr Phe Met Ala Val Gly
            35                  40                  45

Gly Gly Leu Ala Val Ala Gly Leu Pro Ala Leu Gly Phe Thr Gly Ala
    50                  55                  60

Gly Ile Ala Ala Asn Ser Val Ala Ala Ser Leu Met Ser Met Ser Ala
65                  70                  75                  80

Ile Leu Asn Gly Gly Val Pro Ala Gly Leu Val Ala Thr Leu
                85                  90                  95

Gln Ser Leu Gly Ala Gly Gly Ser Ser Val Val Ile Gly Asn Ile Gly
            100                 105                 110

Ala Leu Met Gly Tyr Ala Thr His Lys Tyr Leu Asp Ser Glu Glu Asp
        115                 120                 125

Glu Glu
    130

<210> SEQ ID NO 2
<211> LENGTH: 134
<212> TYPE: PRT
<213> ORGANISM: Artificial Sequence
<220> FEATURE:
<223> OTHER INFORMATION: Synthetic Polypeptide

<400> SEQUENCE: 2

Met Arg Gln Lys Ala Val Ser Leu Phe Leu Cys Tyr Leu Leu Leu Phe
1               5                   10                  15

Thr Cys Ser Gly Val Glu Ala Gly Glu Asn Ala Gly Lys Lys Cys
            20                  25                  30

Ser Glu Ser Ser Asp Ser Gly Ser Gly Phe Trp Lys Ala Leu Thr Phe
        35                  40                  45

Met Ala Val Gly Gly Gly Leu Ala Val Ala Gly Leu Pro Ala Leu Gly
    50                  55                  60

Phe Thr Gly Ala Gly Ile Ala Ala Asn Ser Val Ala Ala Ser Leu Met
65                  70                  75                  80

Ser Met Ser Ala Ile Leu Asn Gly Gly Val Pro Ala Gly Gly Leu
                85                  90                  95

Val Ala Thr Leu Gln Ser Leu Gly Ala Gly Gly Ser Ser Val Val Ile
            100                 105                 110

Gly Asn Ile Gly Ala Leu Met Gly Tyr Ala Thr His Lys Tyr Leu Asp
        115                 120                 125

Ser Glu Glu Asp Glu Glu
    130

<210> SEQ ID NO 3
<211> LENGTH: 138

```
<212> TYPE: PRT
<213> ORGANISM: Artificial Sequence
<220> FEATURE:
<223> OTHER INFORMATION: Synthetic Polypeptide

<400> SEQUENCE: 3

Met Arg Gln Lys Ala Val Ser Leu Phe Leu Cys Tyr Leu Leu Leu Phe
1               5                   10                  15

Thr Cys Ser Gly Val Glu Ala Gly Glu Asn Ala Gly Lys Asp Ala Gly
            20                  25                  30

Lys Lys Lys Cys Ser Glu Ser Ser Asp Ser Gly Ser Gly Phe Trp Lys
        35                  40                  45

Ala Leu Thr Phe Met Ala Val Gly Gly Gly Leu Ala Val Ala Gly Leu
    50                  55                  60

Pro Ala Leu Gly Phe Thr Gly Ala Gly Ile Ala Ala Asn Ser Val Ala
65                  70                  75                  80

Ala Ser Leu Met Ser Met Ser Ala Ile Leu Asn Gly Gly Val Pro
                85                  90                  95

Ala Gly Gly Leu Val Ala Thr Leu Gln Ser Leu Gly Ala Gly Gly Ser
            100                 105                 110

Ser Val Val Ile Gly Asn Ile Gly Ala Leu Met Gly Tyr Ala Thr His
            115                 120                 125

Lys Tyr Leu Asp Ser Glu Glu Asp Glu Glu
        130                 135

<210> SEQ ID NO 4
<211> LENGTH: 418
<212> TYPE: PRT
<213> ORGANISM: Artificial Sequence
<220> FEATURE:
<223> OTHER INFORMATION: Synthetic Polypeptide

<400> SEQUENCE: 4

Met Pro Ser Ser Val Ser Trp Gly Ile Leu Leu Leu Ala Gly Leu Cys
1               5                   10                  15

Cys Leu Val Pro Val Ser Leu Ala Glu Asp Pro Gln Gly Asp Ala Ala
            20                  25                  30

Gln Lys Thr Asp Thr Ser His His Asp Gln Asp His Pro Thr Phe Asn
        35                  40                  45

Lys Ile Thr Pro Asn Leu Ala Glu Phe Ala Phe Ser Leu Tyr Arg Gln
    50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Ala Gln Ile His Glu Gly Phe Gln Glu Leu Leu Arg Thr Leu Asn
            115                 120                 125

Gln Pro Asp Ser Gln Leu Gln Leu Thr Thr Gly Asn Gly Leu Phe Leu
        130                 135                 140

Ser Glu Gly Leu Lys Leu Val Asp Lys Phe Leu Glu Asp Val Lys Lys
145                 150                 155                 160

Leu Tyr His Ser Glu Ala Phe Thr Val Asn Phe Gly Asp Thr Glu Glu
                165                 170                 175

Ala Lys Lys Gln Ile Asn Asp Tyr Val Glu Lys Gly Thr Gln Gly Lys
            180                 185                 190
```

```
Ile Val Asp Leu Val Lys Glu Leu Asp Arg Asp Thr Val Phe Ala Leu
            195                 200                 205
Val Asn Tyr Ile Phe Phe Lys Gly Lys Trp Glu Arg Pro Phe Glu Val
    210                 215                 220
Lys Asp Thr Glu Glu Glu Asp Phe His Val Asp Gln Val Thr Thr Val
225                 230                 235                 240
Lys Val Pro Met Met Lys Arg Leu Gly Met Phe Asn Ile Gln His Cys
                245                 250                 255
Lys Lys Leu Ser Ser Trp Val Leu Leu Met Lys Tyr Leu Gly Asn Ala
            260                 265                 270
Thr Ala Ile Phe Phe Leu Pro Asp Glu Gly Lys Leu Gln His Leu Glu
            275                 280                 285
Asn Glu Leu Thr His Asp Ile Ile Thr Lys Phe Leu Glu Asn Glu Asp
    290                 295                 300
Arg Arg Ser Ala Ser Leu His Leu Pro Lys Leu Ser Ile Thr Gly Thr
305                 310                 315                 320
Tyr Asp Leu Lys Ser Val Leu Gly Gln Leu Gly Ile Thr Lys Val Phe
                325                 330                 335
Ser Asn Gly Ala Asp Leu Ser Gly Val Thr Glu Glu Ala Pro Leu Lys
            340                 345                 350
Leu Ser Lys Ala Val His Lys Ala Val Leu Thr Ile Asp Glu Lys Gly
            355                 360                 365
Thr Glu Ala Ala Gly Ala Met Phe Leu Glu Ala Ile Pro Met Ser Ile
    370                 375                 380
Pro Pro Glu Val Lys Phe Asn Lys Pro Phe Val Phe Leu Met Ile Glu
385                 390                 395                 400
Gln Asn Thr Lys Ser Pro Leu Phe Met Gly Lys Val Val Asn Pro Thr
                405                 410                 415
Gln Lys

<210> SEQ ID NO 5
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 5

Met Ile Glu Gln Asn Thr Lys Ser Pro Leu Phe Met Gly Lys Val Val
1               5                   10                  15

Asn Pro Thr Gln Lys
            20

<210> SEQ ID NO 6
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 6

Leu Met Ile Glu Gln Asn Thr Lys Ser Pro Leu Phe Met Gly Lys Val
1               5                   10                  15

Val Asn Pro Thr Gln Lys
            20
```

METHODS AND COMPOSITIONS FOR DETECTING MISFOLDED PROTEINS

RELATED APPLICATIONS

This application is a continuation of U.S. application Ser. No. 16/406,942, filed May 8, 2019, which is a division of U.S. application Ser. No. 14/683,908, filed Apr. 10, 2015, which claims the benefit under 35 U.S.C. § 119(e) of U.S. provisional application No. 61/978,158, filed Apr. 10, 2014, each of which is incorporated by reference herein in its entirety.

FIELD

Aspects of the present disclosure relate to the fields of diagnostics and prognostics.

BACKGROUND

Preeclampsia (PE) is a pregnancy-specific hypertensive disorder and a leading cause of maternal and perinatal morbidity and death worldwide. World Health Organization (WHO) estimates that 16% of global maternal mortality (63,000 maternal deaths annually) is due to PE alone. In the U.S., preeclampsia affects 5-8% of all pregnancies or 270,000 women and is responsible for 18% of maternal deaths each year and the occurrence is rising. Infants are also at risk; 10,500 babies die each year due to preeclampsia in the US. Preeclampsia is diagnosed based on observed symptoms. There is no accurate diagnostic product for preeclampsia.

The risk of maternal death is much higher in resource-limited settings. The most often recognized factor responsible for major maternal and fetal morbidity is failure to recognize preeclampsia in a timely manner. This is a major obstacle because it does not allow for transfer of the woman with preeclampsia to a higher level health care facility where she can be managed with magnesium, steroid therapy and/or emergent delivery prior to eclampsia, maternal hypertensive stroke or fetal death due to abruption. Preeclampsia is an evolving condition. Therefore, improving detection of preeclampsia in women who are clinically asymptomatic or questionably symptomatic for preeclampsia will be of significant clinical importance. This strategy is known as secondary preeclampsia prevention, and has the potential of reducing pregnancy-related mortality and morbidity by preventing eclampsia and damage to end-organ systems due to convulsions, stroke, pulmonary edema, liver and/or kidney failure and maternal death.

Once severe preeclampsia (sPE) is diagnosed, magnesium sulfate, antihypertensive drugs and medically indicated delivery are effective strategies that have already proven lifesaving (strategies known as tertiary preeclampsia prevention). For preterm pregnancies, correct timing of medically indicated delivery to allow for conservative management (e.g., steroids) is also known to improve neonatal outcomes. The use of therapeutic strategies for prevention of preeclampsia complication is conditioned by the accurate diagnosis of this condition.

SUMMARY

Preeclampsia is a hypertensive proteinuric syndrome unique to human pregnancy. One problem with diagnosing preeclampsia is that neither hypertension nor proteinuria is sensitive or specific, especially in women with atypical presentations. Urine of preeclamptic women is highly enriched in misfolded proteins. Because of this enrichment in misfolded proteins, a simple dye test, using a dye with an affinity for misfolded proteins can be used as a diagnostic and clinical prognostic tool for preeclampsia. An example of one such dye test is the Congo Red Dot test, which includes the use of an azo dye, Congo Red, with an affinity for (e.g., ability to bind to) misfolded proteins.

Provided herein, in some embodiments, are scientific and technological approaches to address the limitations of the typical urine dipstick for evaluation of proteinuria. The present disclosure provides, in some embodiments, a paper-based method (referred to, in some embodiments, as the Congo Red Dot Simple Kit) that permits semi-quantitative results in a short time period (e.g., 2 minutes). The present disclosure also provides, in some embodiments, a smart phone-based method (referred to, in some embodiments, as the Congo Red Dot Quant Kit) for image analysis, which permits a quantitative and unbiased assessment of misfolded proteins in urine in a short period of time (e.g., 7 minutes) with potential, for example, to address the inability to complete a 24 hour proteinuria assessment in health care facilities, such as resource-limited health care facilities.

It should be understood that Congo Red is one non-limiting example of a dye that can be used in accordance with the present disclosure. For simplicity, the tests and kits described herein are referred to with specific reference to Congo Red (e.g., Congo Red Dot Simple Kit); however, in some embodiments, a dye, other than Congo Red, with an affinity for misfolded proteins and, as explained below, cellulose can be used. Similarly, reference is made to "urine congophilia," which refers to urine with misfolded proteins that bind Congo Red. It should be understood that this term is not intended to be limiting. Proteins that are congophilic may also have an affinity for other dyes that can be used as a substitute for Congo Red.

Some aspects of the present disclosure provide methods of determining that a sample (e.g., a urine sample) obtained from a subject (e.g., pregnant woman) contains or does not contain misfolded proteins. In some embodiments, the methods comprise (a) combining a sample (e.g., a urine sample) obtained from a subject (e.g., pregnant woman) with a dye that binds misfolded proteins and a material that contains free hydroxyl groups (e.g., cellulose), thereby producing a solution (e.g., of urine and dye); (b) applying the solution to a surface that comprises a material that contain free hydroxyl groups (e.g., cellulose), under conditions under which the dye binds misfolded proteins and a material that contains free hydroxyl groups (e.g., cellulose), thereby producing a spot on the surface (e.g., a spot comprising dye); (c) maintaining the spot on the surface under conditions under which diffusion of a solution (e.g., of urine comprising misfolded proteins and dye) occurs; and (d) determining that the sample (e.g., urine sample) contains misfolded proteins if dye diffuses (e.g., diffuses radially) to an appreciable extent from the spot on the surface, or determining that the sample (e.g., urine sample) does not contain misfolded proteins if dye does not diffuse (e.g., diffuse radially) to an appreciable extent from the spot on the surface. In some embodiments, conditions under which the dye binds misfolded proteins and a material that contains free hydroxyl groups include room temperature (e.g., ~25° C.) conditions for 30 minutes to 3 hours, or more (e.g., 30 minutes, 1 hour, 2 hours, or 3 hours).

Some aspects of the present disclosure provide methods of detecting misfolded proteins in a sample (e.g., a urine sample) obtained from a subject (e.g., pregnant woman). In some embodiments, the methods comprise (a) combining a sample (e.g., a urine sample) obtained from a subject (e.g., pregnant woman) with a dye that binds misfolded proteins and a surface that comprises a material containing free hydroxyl groups (e.g., cellulose), thereby producing a solution of the sample (e.g., urine) and dye; (b) applying the solution to a surface that comprises a material containing free hydroxyl groups, such as a surface that comprises cellulose, under conditions under which the dye binds misfolded proteins, binds a surface that comprises a material containing free hydroxyl groups, or binds misfolded proteins and a surface that comprises a material containing free hydroxyl groups, thereby producing a spot on the surface; (c) maintaining the spot on the surface under conditions under which diffusion of a solution (e.g., of urine comprising misfolded proteins and dye) occurs; and (d) detecting misfolded proteins in the sample (e.g., urine sample) if dye diffuses (e.g., diffuses radially) to an appreciable extent from the spot on the surface, or not detecting misfolded proteins in the sample (e.g., urine sample) if dye does not diffuse (e.g., does not diffuse radially) to an appreciable extent from the spot on the surface.

Some aspects of the present disclosure provide methods of detecting misfolded proteins in a sample (e.g., a urine sample) obtained from a subject (e.g., pregnant woman). In some embodiments, the methods comprise (a) combining a sample (e.g., a urine sample) obtained from a subject (e.g., pregnant woman) with a dye that binds misfolded proteins and a surface that comprises a material containing free hydroxyl groups (e.g., cellulose), thereby producing a solution of the sample (e.g., urine) and dye; (b) applying the solution to a surface that comprises a material containing free hydroxyl groups, such as a surface that comprises cellulose, under conditions under which the dye binds misfolded proteins, binds the surface that comprises a material containing free hydroxyl groups, or binds misfolded proteins and the surface that comprises a material containing free hydroxyl groups, thereby producing a spot on the surface; (c) maintaining the spot on the surface under conditions under which diffusion of a solution (e.g., of urine comprising misfolded proteins and dye) occurs; and (d) determining if dye diffuses to an appreciable extent from the spot on the surface, wherein if dye diffuses to an appreciable extent, misfolded proteins are detected in the sample (e.g., urine sample) and if dye does not diffuse to an appreciable extent, misfolded proteins are not detected in the urine sample.

Some aspects of the present disclosure provide methods of determining that a sample (e.g., a urine sample) obtained from a pregnant woman contains or does not contain misfolded proteins, comprising (a) combining a sample (e.g., a urine sample) obtained from a pregnant woman with a dye that binds misfolded proteins and a surface that comprises a material containing free hydroxyl groups (e.g., cellulose), thereby producing a solution the sample (e.g., urine) and dye; (b) applying the solution to a surface that comprises a material containing free hydroxyl groups (e.g., cellulose), under conditions under which the dye binds misfolded proteins, binds the surface that comprises a material containing free hydroxyl groups, or binds misfolded proteins and the surface that comprises a material containing free hydroxyl groups, thereby producing a spot on the surface; (c) maintaining the spot on the surface under conditions under which diffusion of a solution (e.g., of urine comprising misfolded proteins and dye) occurs; and (d) determining that the sample (e.g., urine sample) contains misfolded proteins if solution that passes through the surface is colored, or determining that the sample (e.g., urine sample) does not contain misfolded proteins if solution that passes through the surface is colorless.

In some embodiments, methods further comprise comparing the extent to which the solution (e.g., of urine and dye) diffuses (e.g., diffuses radially) from the spot on the surface to the extent to which a positive control diffuses, and determining that the sample (e.g., urine sample) contains misfolded proteins if the extent to which the solution (e.g., of urine and dye) diffuses (e.g., diffuses radially) from the spot on the surface is comparable to the extent to which diffusion occurs in a positive control.

In some embodiments, methods further comprise comparing the extent to which the solution (e.g., of urine and dye) diffuses (e.g., diffuses radially) from the spot on the surface to the extent to which a negative control diffuses, and determining that the sample (e.g., urine sample) does not contain misfolded proteins if the extent to which the solution (e.g., of urine and dye) diffuses (e.g., diffuses radially) from the spot on the surface is comparable to the extent to which diffusion occurs in a negative control.

In some embodiments, methods further comprise (e) diluting an additional sample (e.g., urine sample) from the pregnant woman, thereby producing a dilute sample (e.g., dilute urine sample); (f) combining the dilute sample (e.g., urine sample) with a dye that binds misfolded proteins and a surface that comprises a material containing free hydroxyl groups (e.g., cellulose), thereby producing a solution (e.g., of urine and the dye); (g) applying the solution of (f) to a surface that comprises cellulose, under conditions under which the dye binds misfolded proteins, binds a surface that comprises a material containing free hydroxyl groups, or binds misfolded proteins and a surface that comprises a material containing free hydroxyl groups, thereby producing a spot on the surface; (h) maintaining the spot on the surface of under conditions under which diffusion of a solution (e.g., of urine comprising misfolded proteins and dye) occurs; and (i) determining that the dilute sample (e.g., dilute urine sample) contains misfolded proteins if dye diffuses (e.g., diffuses radially) from the spot on the surface of step (h) or determining that the sample (e.g., urine sample) does not contain misfolded proteins if dye does not diffuse (e.g., diffuse radially) from the spot on the surface maintained in (h).

In some embodiments, the additional sample (e.g., urine sample) is diluted to the extent needed for the conditions under which the method is carried out, such as 5-fold to 15-fold (e.g., 5-fold, 6-fold, 7-fold, 8-fold, 9-fold, 10-fold, 11-fold, 12-fold, 13-fold, 14-fold or 15-fold).

In some embodiments, the subject is a pregnant woman. In some embodiments, the subject is a pregnant woman suspected of having preeclampsia. In some embodiments, the subject is a pregnant woman at risk of developing (e.g., is genetically predisposed to, or has previously had) preeclampsia. In some embodiments, the methods further comprise diagnosing the pregnant woman as having preeclampsia, or as likely to develop preeclampsia, if the sample (e.g., urine sample) contains misfolded proteins or if misfolded proteins are detected.

In some embodiments, the dye is Congo Red.

In some embodiments, the concentration of the dye in the solution is 0.05% to 0.2%. For example, the concentration of the dye in the solution may be 0.1%.

In some embodiments, the material that contains free hydroxyl groups is cellulose. In some embodiments, the surface is paper or contains paper.

In some embodiments, the surface further comprises an adhesive backing.

Some aspects of the present disclosure provide methods of determining that a sample (e.g., a urine sample) obtained from a subject (e.g., a pregnant woman) contains or does not contain misfolded proteins. In some embodiments, the methods comprise (a) combining a sample (e.g., a urine sample) obtained from a subject (e.g., a pregnant woman) with a first dye that binds misfolded proteins and a material that contains free hydroxyl groups (e.g., cellulose) and a second dye that is a different color from the first dye and does not bind misfolded proteins and a material that contains free hydroxyl groups (e.g., cellulose), thereby producing a solution (e.g., of urine and two dyes); (b) applying the solution to a surface that comprises a material that contains free hydroxyl groups (e.g., cellulose), under conditions under which the first dye binds misfolded proteins, binds the surface that comprises material containing free hydroxyl groups (e.g., cellulose), or binds misfolded proteins and the surface that comprises material containing free hydroxyl groups, thereby producing a spot on the surface; (c) maintaining the spot on the surface under conditions under which diffusion of a solution (e.g., of urine comprising misfolded proteins and dye) occurs; and (d) determining that the sample (e.g., urine sample) contains misfolded proteins if the first dye and the second dye diffuse (e.g., radially) to an appreciable extent from the spot on the surface, or determining that the sample (e.g., urine sample) does not contain misfolded proteins if the second dye, but not the first dye, diffuses (e.g., radially) to an appreciable extent from the spot on the surface.

Some aspects of the present disclosure provide methods of detecting misfolded proteins in a subject (e.g., a pregnant woman). In some embodiments, the methods comprise (a) combining a sample (e.g., a urine sample) obtained from a subject (e.g., a pregnant woman) with (i) a first dye that binds misfolded proteins and a material that contains free hydroxyl groups (e.g., cellulose) and (ii) a second dye that is a different color from the first dye and does not bind misfolded proteins and a material that contains free hydroxyl groups (e.g., cellulose), thereby producing a solution (e.g., of urine and two dyes); (b) applying the solution to a surface that comprises cellulose, under conditions under which the first dye binds misfolded proteins and cellulose, thereby producing a spot on the surface; (c) maintaining the spot on the surface under conditions under which diffusion of a solution (e.g., of urine comprising misfolded proteins and dye) occurs; and (d) detecting misfolded proteins in the sample (e.g., urine sample) if the first dye and the second dye diffuse (e.g., diffuse radially) to an appreciable extent from the spot on the surface, or not detecting misfolded proteins in the sample (e.g., urine sample) if the second dye, but not the first dye, diffuses (e.g., radially) to an appreciable extent from the spot on the surface.

In some embodiments, the methods further comprise comparing the extent to which the solution (e.g., of urine and two dyes) diffuses (e.g., diffuses radially) from the spot on the surface to the extent to which diffusion occurs in a positive control, and determining that the sample (e.g., urine sample) contains misfolded proteins if the extent to which the solution (e.g., of urine and two dyes) diffuses radially from the spot on the surface is comparable to the extent to which diffusion occurs in the positive control.

In some embodiments, the methods further comprise comparing the extent to which the solution (e.g., of urine and two dyes) diffuses (e.g., diffuses radially) from the spot on the surface to the extent to which diffusion occurs in a negative control, and determining that the sample (e.g., urine sample) contains misfolded proteins if the extent to which the solution (e.g., of urine and two dyes) diffuses radially from the spot on the surface is comparable to the extent to which diffusion occurs in the negative control.

In some embodiments, the methods further comprise acquiring an image of the spot on the surface. An image may be acquired, for example, using a mobile telephone.

In some embodiments, the methods further comprise quantifying the difference between the extent to which the first dye diffuses radially from the spot on the surface and the extent to which the second dye diffuses radially from the spot on the surface. Two different dyes may be used, for example, in the calibration procedure, as provided herein.

In some embodiments, the methods further comprise calculating a correlation coefficient between the extent to which the first dye diffuses radially from the spot on the surface and the extent to which the second dye diffuses radially from the spot on the surface. For example, a correlation coefficient may be calculated using an algorithm (e.g., algorithm that assesses the correlation coefficient (p) between the signal in different color channels of pictures taken with a smartphone).

In some embodiments, the first dye is Congo Red.

In some embodiments, the second dye is erioglaucine.

In some embodiments, the concentration of the first dye in the solution is 0.05% to 0.2%. For example, the concentration of the first dye in the solution may be 0.1%.

In some embodiments, the concentration of the second dye in the solution is 0.05% to 0.2%. For example, the concentration of the second dye in the solution may be 0.1%.

In some embodiments, the methods further comprise (e) diluting an additional sample (e.g., urine sample) from the pregnant woman, thereby producing a dilute sample (e.g., urine sample), (f) combining the sample (e.g., urine sample) with a first dye that binds misfolded proteins and a material that contains free hydroxyl groups (e.g., cellulose) and a second dye that is different from the first dye and does not bind misfolded proteins and a material that contains free hydroxyl groups (e.g., cellulose), thereby producing a solution (e.g., of urine and two dyes); (g) applying the solution of (f) to a surface that comprises a material that contains free hydroxyl groups (e.g., cellulose) under conditions under which the first dye binds misfolded proteins and a material that contains free hydroxyl groups (e.g., cellulose), thereby producing a spot on the surface; (h) maintaining the spot on the surface of step (g) under conditions under which diffusion of a solution (e.g., of urine comprising misfolded proteins and dye occurs); and (i) determining that the dilute sample (e.g., urine sample) contains misfolded proteins if the first dye and the second dye diffuse (e.g., diffuse radially) from the spot on the surface of (h), or determining that the sample (e.g., urine sample) does not contain misfolded proteins if the second dye, but not the first dye, diffuses (e.g., diffuses radially) from the spot on the surface of (h).

In some embodiments, the additional sample (e.g., urine sample) is diluted 5-fold to 15-fold.

Also described herein are kits for determining that a sample (e.g., a urine sample) obtained from a subject (e.g., pregnant woman) contains or does not contain misfolded proteins. Some embodiments are kits for detecting misfolded proteins in a sample (e.g., a urine sample) obtained from a subject (e.g., pregnant woman). In some embodiments, the kits comprise (a) a dye that binds misfolded proteins and cellulose, (b) a surface that comprises a material that contains free hydroxyl groups (e.g., cellulose) and, optionally, an applicator.

In some embodiments, the surface that comprises a material that contains free hydroxyl groups (e.g., cellulose) is affixed to an additional surface.

In some embodiments, the dye is in an aqueous solution (e.g., preloaded within an applicator). An aqueous solution may comprise, for example, water or other buffer (e.g., phosphate buffered saline). In some embodiments, an aqueous solution does not contain an alcohol (e.g., ethanol, methanol, isopropanol).

In some embodiments, the concentration of the dye in the aqueous solution is 0.2% to 1.0%. For example, the concentration of the dye in the aqueous solution may be 0.5%.

In some embodiments, the volume of the aqueous solution is 1 µl to 10 µl. For example, the volume of the aqueous solution may be 5 µl.

In some embodiments, the kit further comprises an applicator (e.g., a pipette, such as a disposable pipette). In some embodiments, the applicator is preloaded with the dye.

In some embodiments, the kit further comprises a positive control, a negative control, or both a positive control and a negative control.

In some embodiments, the kit further comprises images of positive and negative results for comparison to test results to determine if the sample is positive or negative for the presence of misfolded proteins.

Also described herein are kits for determining that a sample (e.g., urine sample) obtained from a subject (e.g., pregnant woman) contains or does not contain misfolded proteins. Some embodiments are kits for detecting misfolded proteins in a sample (e.g., urine sample) obtained from a subject (e.g., pregnant woman). In some embodiments, the kits comprise (a) a first dye that binds misfolded proteins and a material that contains free hydroxyl groups (e.g., cellulose), (b) a second dye that is a different color from the first dye and does not bind misfolded proteins and a material that contains free hydroxyl groups (e.g., cellulose), (c) a surface that comprises a material that contains free hydroxyl groups (e.g., cellulose), and (d) optionally, an applicator.

In some embodiments, the first dye is Congo Red. In some embodiments, the second dye is erioglaucine.

In some embodiments, the surface is paper.

In some embodiments, the first dye and the second dye are combined in an aqueous solution, thereby producing an aqueous solution of two dyes.

In some embodiments, the concentration of the two dyes in the aqueous solution is 0.2% to 1.0%. For example, the concentration of the two dyes in the aqueous solution may be 0.5%.

In some embodiments, the volume of the aqueous solution is 1 µl to 10 µl. For example, the volume of the aqueous solution may be 7.5 µl.

In some embodiments, the applicator is preloaded with the aqueous solution of two dyes.

In some embodiments, the applicator is a pipette (e.g., a disposable pipette).

In some embodiments, the kits further comprise a positive control, a negative control, or both a positive control and a negative control.

Also described herein are compositions comprising urine (e.g., obtained from a pregnant woman), a dye that binds misfolded proteins and cellulose, and a surface that comprises cellulose.

Further described herein is an apparatus comprising any one of the kits described herein and a urine sample obtained from a pregnant woman.

In some embodiments, the method further comprises treating the subject for preeclampsia (e.g., administering medication to lower blood pressure, administering a corticosteroid, administering an anticonvulsant medication).

Some aspects relate to methods of determining whether a pregnant woman has, or is at risk of, preeclampsia, the method comprising (a) combining a urine sample from a pregnant woman with Congo Red, thereby producing a solution of urine and Congo Red; (b) applying the solution to a surface that comprises cellulose, thereby producing a spot on the surface; (c) maintaining the spot on the surface under conditions under which diffusion of a solution of urine comprising dye occurs; and (d) determining that the pregnant woman has, or is at risk of, preeclampsia if the Congo Red diffuses to an appreciable extent from the spot on the surface.

Some aspects provide methods of detecting misfolded proteins in a urine sample obtained from a pregnant woman, comprising (a) applying, to a surface onto which Congo Red is adsorbed, a urine sample obtained from a pregnant woman, thereby producing a surface that contains urine and Congo Red, and (b) subjecting the surface that contains urine and Congo Red to isoelectric focusing, and (c) determining the extent of, or the rate of, migration of Congo Red. In some embodiments, the methods further comprise comparing the extent of, or the rate of, migration of Congo Red to an appropriate positive or negative control, wherein a difference in the extent of, or the rate of, migration of Congo Red relative to the appropriate control is indicative of misfolded proteins in the urine sample. "Isoelectric focusing" refers to a technique for separating different molecules by differences in their isoelectric point (pI). Isoelectric focusing is a type of zone electrophoresis, typically performed on proteins in a gel (or other porous substrate), that takes advantage of the fact that overall charge on the molecule of interest is a function of the pH of its surroundings.

In some embodiments, the surface is a porous surface that permits movement (e.g., migration, e.g., toward a positive or negative electrode) of proteins and dye. For example, the surface may be an agarose gel or agarose beads. Other porous surfaces are contemplated herein.

BRIEF DESCRIPTION OF THE DRAWINGS

FIGS. 3A-3C shows photographs of examples of three different diagnostic kits of the present disclosure. FIG. 3A depicts a Congo Red Simple Kit; FIG. 3B depicts a Congo Red Quant Kit; and FIG. 3C depicts a Congo Red Quant Array.

FIG. 4 show photographs of each step of an example of a Congo Red Quant Array analysis.

FIGS. 6A-6I show examples of spectral characteristics protein aggregation and congophilia in urine of women with severe preeclampsia (sPE).

FIGS. 15A-15F show an example of a comparative aggregation prediction of interferon-inducible protein 6-16 (G1P3) isoforms. Isoform A (SEQ ID NO: 1); Isoform B (SEQ ID NO: 2); and Isoform C (SEQ ID NO: 3).

FIG. 19C: C-terminus fragments of SERPINA1 (proteoforms)—SEQ ID NO: 5 (top) and SEQ ID NO: 6 (bottom).

FIGS. 23A-23B show a screen-by-screen workflow of an example of a Congo Red Dot test array smartphone application.

FIG. 25A shows the front of a trifold-configured kit. FIG. 25B shows the back of a trifold-configured kit.

FIG. 26A shows the front of a trifold-configured kit. FIG. 26B shows the back of a trifold-configured kit.

FIG. 27A shows examples of diffusion of control urine drops with increasing Congo Red/food dye ratio from left to right. FIG. 27B shows examples of diffusion of preeclamptic urine drops with increasing Congo Red/food dye ratio from left to right.

FIG. 28 shows an image containing samples of non-preeclamptic urine (lanes 1 and 3) and preeclamptic urine (lanes 4 and 5) applied to an agarose gel containing Congo red (e.g., adsorbed onto the surface of the gel). When the gel was subjected to isoelectric focusing, proteins in the urine were pushed through the gel and when they reach the adsorbed Congo Red dye, the proteins intercalate the dye. Congo Red associated with congophilic proteins (in preeclamptic urine) migrates through the gel at a rate (or to an extent) different from Congo Red not associated with congophilic protein.

DETAILED DESCRIPTION

Figure 1:
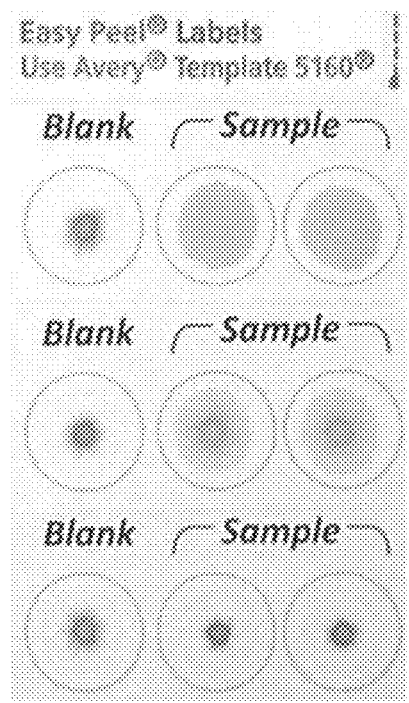
FIG. 1 shows a comparison of examples of methods of the present disclosure using "plain" paper with urine samples obtained from three different test subjects: a pregnant woman with severe preeclampsia (Case 1); a pregnant woman with preeclampsia (Case 2); and a pregnant woman without preeclampsia. "Blank" represents Congo Red dye mixed with water; "Sample" (two adjacent to each other) represents Congo Red dye mixed with the designated urine sample.

A significant challenge has been that the cornerstones of preeclampsia (PE) diagnosis, hypertension and proteinuria rely on quantitative measurements of blood pressure (BP) and urine proteins, which are symptomatic of, but not specific for, preeclampsia. Furthermore, these measurements are difficult to achieve in low-resource settings. Additionally, the diagnosis of preeclampsia continues to challenge Maternal Fetal Medicine specialists, even in high-resource settings, when preeclampsia coexists with chronic hypertension (crHTN) (e.g., instance known as spPE) or chronic kidney diseases. Other challenges are posed by "atypical" clinical manifestations such as isolated neurological symptoms, right upper quadrant pain, elevated liver enzymes, and oliguria which sometimes manifest with minimal or absent hypertension or proteinuria. In high-resource settings, these women are admitted to tertiary level hospitals and have extensive blood and urine lab work-up every 4-6 hours along with continuous blood pressure and fetal monitoring. In many low resource settings and underdeveloped countries, this is practically unachievable.

According to the United Nation's Children's Fund (UNICEF), in the developing world, 80% of women receive antenatal care (ANC) from a skilled health provider, at least once in pregnancy. However, the quality and number of ANC visits remains suboptimal for effective detection of preeclampsia. As antenatal care practice alone has proven ineffective at preventing eclampsia, failure to measure blood pressure and proteinuria at each antenatal care visit represents a missed opportunity. In fact, during antenatal care visits, more women seem to have their blood pressure measured than their urine screened for proteins. Evidently, without assessing for proteinuria, proper screening or differential diagnosis of preeclampsia from the more benign pregnancy-associated hypertensive conditions, such as crHTN and gestational hypertension (gestHT), cannot be attained. Improving upon the assessment of proteinuria for detection of preeclampsia in low-resource settings has potential to fill a gap.

To be meaningful for ruling-in or ruling-out preeclampsia in the clinical set-up, proteinuria may be assessed quantitatively. Physiological changes with hydration, posture and pregnancy itself change the amount of proteins present in urine. For these reasons, the "gold" standard for proteinuria assessment in pregnancy is from a timed (24 hour) urine collection. In the U.S. and Canada, most women with suspected preeclampsia are hospitalized during collection, although some may be managed as outpatients and instructed to collect the 24-hour urine sample at home. The burden of collecting a complete sample, and the requirement for refrigeration between each void, leads to noncompliance and test inaccuracy. A study in Canada testing completeness of 24 hour collections found that up to 60% of specimens of women evaluated for preeclampsia were volumetrically inadequate. For all the above reasons, and although known to be less accurate than 24-hour proteinuria, the urine dipstick remains a popular method for preeclampsia screening.

Several studies have shown that urine dipsticks are associated with substantial false positives and negatives to a point which makes them unreliable to detect or exclude proteinuria in pregnant women. A prospective study of more than 900 women showed that when applied in a low-risk population, the dipstick in the absence of hypertension is a poor predictor for development of preeclampsia (e.g., high false positive rate). Approximately 40% of women in the study had at least one result of +1 or more during pregnancy. Yet, only 4% developed preeclampsia. Urinary infections, contamination of urine with vaginal secretions, blood or semen are the most often causes of high false positive readings. Patient self-assessment of dipstick readings were further found to overestimate positivity when compared to nurse's readings. Dipsticks also require proper storage, handling and subjective visual reading which have been cited as important sources of error even among trained personnel. In addition, it is well-recognized that the colorimetric reagent used by dipsticks (e.g., tetrabromphenol blue) detects only a fraction of the proteins excreted in preeclampsia urine. For example, two types of proteins light chains of IgG analogous to Bence Jones protein and fragmented albumin, are pathogenically linked to preeclampsia and give zero dipstick reaction. This suggests that dipstick may underestimate the total amount, and lacks important qualitative data related to the type of proteins present in the urine at the time of screening.

Provided herein, in some embodiments, are methods and compositions (e.g., kits) that: (1) are amenable for first level antenatal care clinics; (2) are at least as easy to use as the dipstick, but more specific for proteinuria of preeclampsia; (3) are more reproducible in quantitative scale; and (4) have potential of predicting outcome.

In some embodiments, methods and compositions of the present disclosure are in agreement with the ASSURED criteria for ideal diagnostics (Affordable for those at risk for infection, Sensitive and Specific, User-Friendly, Rapid and robust, Equipment-free, and Delivered to those in need). Surprisingly, women having preeclampsia excrete in urine high levels of misfolded proteins. This increases in severity and precedes up to 10 weeks before the onset of clinical manifestations. In principle, this phenomenon categorizes preeclampsia as a protein conformational disorder similar to Alzheimer's and prion disease. Furthermore, the presence of misfolded proteins can be detected in urine and, in some instances, in blood obtained from women with preeclampsia using certain dyes (e.g., the azo-dye Congo Red). Congo Red, for example, has a self-assembling property and can initiate formation of large insoluble oligomers following binding to amyloid proteins that have an extensive β-sheet structure. Congo Red may intercalate with β-sheet structures if present in proteins in samples (e.g., urine samples). Described herein is a simple colorimetric urine diagnostic test for preeclampsia, referred to as the Congo Red Dot test. Detection of misfolded proteins in urine has diagnostic and prognostic value for preeclampsia, even if assessed in a sample that is a random single void. The reason for this, and in contrast to currently employed methods (e.g., dipstick and turbidimetry in 24-hour urine collections), is, as shown herein, that the presence of misfolded proteins is more closely linked to preeclampsia pathophysiology than is the presence of nonspecific proteinuria. Therefore, in some instances, when a diagnosis of preeclampsia is considered, a positive result for misfolded proteins in urine suggests that the proteins responsible for the clinically significant proteinuria are also misfolded. This qualitative finding of the presence of of misfolded proteinuria is a unique feature of preeclampsia that does not accompany other hypertensive conditions that occur during gestation.

Based, in part, on this assessment, provided herein are methods and compositions (e.g., kits) to, for example, establish a diagnosis of preeclampsia with a high degree of certainty on the basis of misfolded proteins in urine. The methods and compositions provide a significant clinical advantage for health care providers because they enable rapid diagnostic screening sufficiently reliable so that appropriate interventions can be employed.

Some aspects of the present disclosure relate to methods of determining that a urine sample obtained from a subject (e.g., a pregnant woman) contains or does not contain misfolded proteins. Other aspects of the present disclosure relate to methods of detecting misfolded proteins in a sample (e.g., urine sample) obtained from a subject (e.g., a pregnant woman). Protein folding is the process by which a protein assumes its minimal-energy configuration. Each protein exists as an unfolded polypeptide or random coil when translated from a sequence of mRNA to a linear chain of amino acids. During protein folding, a polypeptide folds into its characteristic and functional three-dimensional structure from random coil. Misfolded proteins may result when a protein follows the wrong folding pathway or energy-minimizing funnel, and misfolding can happen spontaneously. Misfolded proteins may also result from aberrant degradation, clearance mechanisms or protein crowding. Misfolded proteins are typically, but not always, insoluble, and tend to form long linear or fibrillar aggregates referred to as amyloid deposits (Dobson C. M. Nature 426, 884-890, 2003, incorporated by reference herein). Examples of misfolded proteins that may be detected individually, or as heterologous co-aggregates, include, without limitation, Serpina-1, albumin, IgG κ-free light chain (KFLC), ceruloplasmin, interferon-inducible protein 6-16 (IFI6 also known as G1P3), amyloid precursor protein (APP). In some embodiments, misfolded proteins are congophilic proteins or congophilic protein aggregates. Misfolded proteins, in some embodiments, may be amyloid proteins or beta-sheet aggregates. In some embodiments, misfolded proteins are aggregates of non-random cleavage fragments of Serpina-1 and albumin. In some embodiments, misfolded proteins are amyloidogenic proteins and may display epitopes, including, for example, prefibrillar oligomers and annular protofibrils.

A urine sample may be collected by any standard means, such as, for example but not limited to, using a clean catch method, which utilizes a cup (e.g., a sterile cup) with a lid. In some embodiments, a urine sample is collected when urine has been in a subject's bladder for 1 to 5 hours (e.g., 1, 2, 3, 4 or 5 hours). In some embodiments, a urine sample is collected when urine has been in a subject's bladder for less than an hour, or more than 5 hours. It should be understood that the entire urine sample collected from a subject is not necessarily used in the method of the present disclosure. In some embodiments, a "urine sample" for use in a method of the present disclosure (e.g., a sample that is combined with a dye) is 10 µl to 1 ml, or more. In some embodiments, a urine sample is 50 µl to 500 µl. In some embodiments, a urine sample is 10 µl, 20 µl, 30 µl, 40 µl, 50 µl, 60 µl, 70 µl, 80 µl, 90 µl, 100 µl, 110 µl, 120 µl, 130 µl, 140 µl, 150 µl, 160 µl, 170 µl, 180 µl, 190 µl or 200 µl. In some embodiments, a urine sample is 100 µl, 200 µl, 300 µl, 400 µl or 500 µl.

A subject may be any subject suspected of having misfolded proteins in his or her urine. In some embodiments, a subject is a woman, such as pregnant woman. In some embodiments, a subject is a pregnant woman suspected of having and/or at risk of developing preeclampsia. A urine sample of the present disclosure may be obtained from a woman who is at 1 to 20 weeks, 20 to 40 weeks, or 1 to 40 weeks, of gestation, or later. In some embodiments, a urine sample is obtained from a pregnant woman who is at 1 to 5, 1 to 10, 1 to 15, 5 to 10, 5 to 15, 5 to 20, 10 to 15, 10 to 20, or 15 to 20 weeks of gestation. In some embodiments, a urine sample is obtained from a pregnant woman who is at 15 to 20, 15 to 25, 15 to 30, 15 to 35, 15 to 40, 20 to 30, 20 to 35, 20 to 40, 25 to 25, or 25 to 40 weeks of gestation. In some embodiments, a urine sample may be from a pregnant woman who is at less than 1 week of gestation (e.g., 1, 2, 3, 4, 5 or 6 days of gestation). In some embodiments, a urine sample is obtained from a woman who is pregnant in the first trimester, second trimester, or third trimester. In some embodiments, a urine sample is obtained from a woman who is not pregnant and who is considering becoming pregnant (e.g., to assess a baseline level of congophilia). In some embodiments, a urine sample is obtained from a woman who is in postpartum.

In some embodiments, a urine sample is obtained from a pregnant woman at any or all prenatal and postpartum checkups with a healthcare provider. For example, a urine sample may be obtained at the first prenatal visit, every 4 weeks until week 28 of pregnancy; every 2 to 3 weeks through week 36 of pregnancy; at least every week during the final month of pregnancy; after delivery; at discharge from a healthcare facility and/or at any postpartum checkups. Urine may be obtained more frequently for women with a preexisting medical problem, women who that develop complications during pregnancy, or pregnant teens.

Various neurodegenerative and non-neurological diseases are caused by, or characterized by, the presence of misfolded proteins. For example, the most prevalent neurodegenerative disease caused by the accumulation of misfolded proteins is Alzheimer's disease. Parkinson's disease and Huntington's disease have similar amyloid origins. Yet another example is amyotrophic lateral sclerosis. Thus, in some embodiments, a subject is not a pregnant woman. In some embodiments, a subject is a one who is suspected of having and/or is at risk of developing a neurological (e.g., neurodegenerative) disorder. In some embodiments, a subject is a one who is suspected of having and/or is at risk of developing a non-neurological disorder.

Some aspects of the present disclosure include combining a urine sample from a subject (e.g., a pregnant woman) with a dye that binds misfolded proteins (e.g., binds preferentially) and also binds cellulose or any material that comprises free hydroxyl groups, thereby producing a solution of urine and dye. A urine sample and a dye (or more than one dye) are considered to be "combined" if they are in the same container (e.g., if the urine sample is added to a container containing the dye, or if the dye is added to a container containing the urine sample or if the urine sample and the dye are combined simultaneously. Thus, a "solution of urine and dye" refers to urine that contains dye. It should be understood that the solution may or may not contain additional components, such as, for example, water or buffer. In some embodiments, a urine sample from a subject is diluted (e.g., with water or buffer) before combining it with dye. In some embodiments, a urine sample remains undiluted.

A dye that binds misfolded proteins is one that has an affinity for (e.g., intercalates with) misfolded proteins. A non-limiting example of a dye that binds misfolded proteins is Congo Red. Congo Red is the sodium salt of 3,3'-([1,1'-biphenyl]-4,4'-diyl)bis(4-aminonaphthalene-1-sulfonic acid. It is a secondary diazo dye that is water soluble, yielding a red colloidal solution. It should be understood that other dyes that bind misfolded proteins can be used in accordance with the present disclosure including, without limitation, other substantive dyes (also known as direct dyes because they do not typically require a mordant and act through hydrogen bonding) such as, for example, those originally extracted from plants or developed to stain cotton and later found to stain amyloids. Examples of such substantive dyes for use as provided herein include, without limitation, sirius red F3B (CI 35780), benzo scarlet 4BNS (CI 29200), sirius scarlet GG (CI 40270), orange G and crystal violet. Additional examples of dyes for use as provided herein include, without limitation, fluorescent dyes such as Thioflavin T and Thioflavin S. In some embodiments, a dye for use as provided herein is Evans Blue, Trypan blue, Amino-8-napthalene sulfonate (ANS) or bis-azo ANS.

A dye that binds cellulose is one that has an affinity for (e.g., intercalates with) cellulose fibers. Examples of dyes that bind cellulose fibers that can be used in accordance with the present disclosure include, without limitation, Congo Red, sirius red F3B (CI 35780), benzo scarlet 4BNS (CI 29200), sirius scarlet GG (CI 40270), orange G, crystal violet, Thioflavin S, Thioflavin T, Evans Blue, Trypan blue, ANS and bis-azo ANS.

Some aspects of the present disclosure include applying a solution of urine and dye to a surface that comprises cellulose, thereby producing a spot on the surface. Cellulose is an organic compound with the formula $(C_6H_{10}O_5)_n$, a polysaccharide including a linear chain of several hundred to over ten thousand $\beta(1\rightarrow4)$ linked D-glucose units. The term "cellulose" excludes nitrocellulose. Thus, a surface comprising cellulose does not comprise nitrocellulose. That is, a surface comprising cellulose is without (is free of) nitrocellulose. In some embodiments, however, a surface comprising cellulose may further comprise nitrocellulose, depending on the type of surface and dye being used.

Dyes, such as, for example, Congo red, appear to have a non-covalent affinity for cellulose and, thus, bind to cellulose. With respect to cellulose, it is thought that Congo red is adsorbed by hydrogen bonding between hydroxyl groups of the polysaccharide chains and the amino groups of the dye. Examples of surfaces that comprise cellulose include paper surfaces (e.g., plain paper, paper labels with adhesive backing), though surfaces that comprise cellulose for use herein are not so limited. Other surfaces that comprise cellulose include cotton, linen, or surfaces containing elastin. Surfaces that comprise cellulose to which, for example, Congo Red binds may be referred to as dye-compatible surfaces or Congo Red-compatible surfaces. Surfaces used herein are considered "compatible" with a specific dye being used if the dye can bind to the surface in the absence of misfolded proteins. Surprisingly, the present disclosure demonstrates that not all surfaces containing cellulose (referred to as cellulosic surfaces) are suitable for use in the methods and compositions provided herein. Even within individual types of cellulosic surfaces, suitability varies. For example, among 50 different types of paper tested, results demonstrated that only select types of paper were suitable. Suitability of the cellulosic surface (e.g., paper) is based on several factors, including, for example, contact angle of the surface, porosity of the surface, fluorescence of the surface (which is a reflection of additive), and ambience (e.g., temperature and humidity of the environment in which a method of the present disclosure is being performed). Thus, conditions under which a dye binds misfolded proteins and cellulose and subsequently diffuses along a surface comprising cellulose (or the dye does not diffuse) depends on any one or more of the foregoing factors. A cellulosic surface is considered suitable for use as provided herein if, when applied to the surface, (1) a solution of urine comprising misfolded proteins and dye diffuses (e.g. radially diffuses) from a point of application of the solution to the cellulosic surface (e.g., as shown in FIG. 1, Case 1, "Sample"); and (2) a solution of urine comprising dye (and not misfolded proteins), the dye does not diffuse radially from a point of application of the solution to the cellulosic surface (e.g., as shown in FIG. 1, Case 1, "Blank"), or if a solution of urine comprising dye (and not misfolded proteins) the dye diffuses (e.g. radially diffuses) to a lesser extent relative to a solution comprising misfolded proteins and dye.

In some embodiments, a correlation coefficient, p, is used to distinguish between suitable paper and unsuitable paper. The exact cut-off of the correlation coefficient, $\rho$, between suitable paper and unsuitable paper is defined by determining the relationship of $\rho$ with the contact angle, $\theta$, on different types of "plain" paper. In some embodiments, a correlation coefficient, $\rho$, of 0.5 or less (e.g., 0.1 to 0.5) is indicative of suitable paper. For example, a $\rho$ of 0.1, 0.2, 0.3, 0.4 or 0.5 is indicative of suitable paper.

"A spot on a surface" refers to the detectable (e.g., observable, visible) spot formed on a surface following application of a solution, for example the solution of urine and dye (with or without misfolded proteins in the urine). Without being bound by theory, cellulose fibers in the surface and misfolded proteins in the urine "compete" for binding with dye. If a urine sample contains misfolded proteins, dye (e.g., Congo Red) binds to the misfolded proteins, and the amount of unbound dye (e.g., dye that is not bound to misfolded proteins) is proportionally reduced. When the solution with urine comprising misfolded proteins and dye is applied to a suitable cellulosic surface (e.g., plain paper), the solution with urine comprising misfolded proteins and dye diffuses (e.g., diffuses radially) from the visible application spot (referred to as the spot on the surface), and diffusion of dye is detectable. For example, when 100 μl of a solution of sample (e.g., urine) comprising misfolded proteins and dye is applied to a suitable cellulosic surface, the solution of sample comprising misfolded proteins and dye diffuses, for example, radially to a distance of 5-7 mm from the application spot, and diffusion of dye is detectable. This extent of diffusion of dye is one example of "diffusing to an appreciable extent" or "diffusing radially to an appreciable extent." Thus, when diffusing radially, the characteristic larger, homogeneous circle (as shown, e.g., in FIG. 1, Case 1, "Sample") formed by diffusion of the solution with urine comprising misfolded proteins and dye is indicative of presence of misfolded proteins in the urine sample. That is, the urine sample contains misfolded proteins.

By contrast, if a sample (e.g. a urine sample) does not contain misfolded proteins, dye (e.g., Congo Red) in the solution is free to bind to the cellulose fibers of the cellulosic surface. When the solution containing, for example, urine and dye, and not misfolded proteins) is applied to a suitable cellulosic surface (e.g., plain paper), the dye binds to the cellulose fibers of the surface in or near the application spot and while urine in the solution diffuses (e.g. radially) from the application spot, dye does not diffuse from the application spot, or dye diffuses to a lesser extent relative to dye in solution with urine comprising misfolded proteins. For example, when 100 μl of a solution with urine comprising dye (and not misfolded proteins) is applied to a suitable cellulosic surface, sample may diffuse (e.g. radially) to a distance of 5-7 mm from the application spot, while dye may diffuse (e.g. radially) to a distance of only 1-3 mm from the application spot. This extent of diffusion of dye is one example of "not diffusing to an appreciable extent" or "not diffusing radially to an appreciable extent." Thus, the characteristic smaller, heterogeneous circle (as shown, e.g., in FIG. 1, Case 1, "Blank") formed by lack of appreciable diffusion of dye is indicative of absence of misfolded proteins in the sample. That is, the sample (e.g., urine sample) does not contain misfolded proteins.

It should be understood that methods of detecting misfolded proteins of the present disclosure rely, in part, on principles of chromatography and, in some embodiments, on visual assessment of chromatographic results. One of ordinary skill in the art would understand what is meant by an "appreciable extent" of diffusion, particularly in light of the protein and dye chemistries described herein. A dye is considered to diffuse an appreciable extent from a central point of a surface if one can determine that dye has spread (e.g. radially) away from the central point. This spreading results because dye is bound to misfolded proteins and, thus, cannot bind to the surface. By comparison, a dye is considered not to diffuse to an appreciable extent if one can determine that dye has not spread (e.g., radially) from the central point (albeit, it may diffuse to a limited extent from the central point, such as of 1-3 mm). This limited spreading results because the dye is not bound to misfolded proteins and can bind to the surface and does so rapidly when it is applied to the surface.

In some embodiments, a sample (e.g. urine) may be "strongly positive" for misfolded protein (e.g., contains enough misfolded protein to bind all or most of the dye in solution). In such embodiments, a characteristic homogenous circle may result from the methods of the present disclosure, as shown, for example, in FIG. 1, Case 1, "Sample." In other embodiments, a sample may be "weakly positive" for misfolded protein (e.g., contains misfolded protein, but not enough to bind all or most of the dye in solution). In such embodiments, a characteristic central spot with a homogeneous "halo" may result from the methods of the present disclosure, as shown, for example, in FIG. 1, Case 2, "Sample." The halo typically results from diffusion of the portion of the dye that is bound to misfolded proteins and therefore does not bind to the cellulose in the central spot area.

Some aspects of the present disclosure include maintaining a spot on a surface that comprises, for example, cellulose under conditions under which diffusion of a solution of urine (or other sample) comprising misfolded proteins and dye occurs. One advantage of methods of the present disclosure, in some embodiments, is that the time needed to obtain a result is short. In some embodiments, a solution, or a spot, is maintained on a surface for 1 to 5 minutes, or more. For example, a spot may be maintained for 1 to 3 minutes, or 1 to 2 minutes. In some embodiments, a spot is maintained for 2 minutes. In some embodiments, a spot is maintained on a surface for less than 1 minute. It should be understood that maintenance also refers, in some embodiments, to maintaining ambience (e.g., temperature and humidity) for the period of time of assessment of a particular sample (e.g., 1 to 5 minutes) that support diffusion of a solution. It should also be understood that the period of time to complete a diagnostic test of the present disclosure may vary, depending on ambience and type of surface (e.g., cellulosic surface).

Some aspects of the present disclosure include determining that the urine sample contains misfolded proteins if solution that passes through the surface is colored, or determining that the urine sample does not contain misfolded proteins if solution that passes through the surface is colorless. For example, if the dye is Congo Red, solution passing through the surface will appear red, pink or purple in color (because the solution contains Congo Red) if misfolded proteins are present in the urine sample. Without being bound by theory, this is because Congo Red, which has bound to the misfolded proteins and which cannot bind to the surface (e.g., as a result of saturation by binding of the misfolded proteins), will pass through the surface. By contrast, solution passing through the surface will appear colorless (because the solution does not contain Congo Red) if misfolded proteins are not present in the urine sample. Without being bound by theory, this is because free Congo Red has bound to the surface, which acts as a filter, letting through only solution void of misfolded proteins and therefore void of Congo Red.

In some embodiments, a surface that comprises cellulose is a surface of plain paper. Plain paper includes paper that does not have a coating. Coated papers can be divided into matte, semi-matte or silk, and gloss (e.g., coated on one or both sides with a thin layer of calcium carbonate or china clay). Thus, paper without a matte, semi-matte or silk, or gloss coating is within the definition of "plain paper." Uncoated printer paper is one non-limiting example of plain paper. Also included within the definition of "plain paper" is paper without additives (e.g., chalk or china clay). Paper, in some instances, may be characterized by weight. Weight assigned to a paper is the weight of a ream (e.g., 500 sheets, wherein 1 sheet equals 17"×22") of paper. In some embodiments, plain paper has a weight of 20 lbs, 24 lbs or 32 lbs. Paper, in some instances, may be characterized by density. In some embodiments, plain paper has a density of 800 kg/m$^3$ (50 lb/ft$^3$).

In some embodiments, as surface comprising cellulose further comprises an adhesive backing. In some embodiments, as surface comprising cellulose with an adhesive backing is a label (e.g., a commercially-available self-adhesive label). Results provided herein show that, in some embodiments, an adhesive backing prevents wrinkling of a paper surface and, thus, provides more accurate results. Nonetheless, surfaces comprising cellulose do not require an adhesive backing.

In some embodiments, a concentration of dye (or a concentration of a combination of two or more dyes) in a solution (e.g., a solution comprising urine and dye) is 0.01% to 1.0%, or more. For example, a concentration of dye (or a concentration of a combination of two or more dyes) in a solution may be 0.01% to 0.1%, 0.01% to 0.2%, 0.01% to 0.3%, 0.01% to 0.4%, 0.05% to 0.1%, 0.05% to 0.2%, 0.05% to 0.3%, 0.05% to 0.4%, 0.05% to 0.5%, 0.05% to 0.6%, 0.05% to 0.7%, 0.05% to 0.8%, or 0.05% to 0.9%. In some embodiments, a concentration of dye (or a concentration of a combination of two or more dyes) in a solution is 0.01%, 0.05%, 0.1%, 0.15%, 0.2%, 0.25%, 0.3%, 0.35%, 0.4%, 0.45%, 0.5%, 0.55%, 0.6%, 0.65%, 0.7%, 0.75%, 0.8%, 0.85%, 0.9%, 0.95% or 1.0%. In some embodiments, a concentration of dye (or a concentration of a combination of two or more dyes) in a solution is 0.1%.

In some embodiments, a concentration of dye (or a concentration of a combination of two or more dyes) in an aqueous solution (e.g., water or an aqueous buffer comprising dye) is 0.2% to 1.0%, or more. For example, a concentration of dye (or a concentration of a combination of two or more dyes) in a solution may be 0.2%, 0.3%, 0.4%, 0.5%, 0.6%, 0.7%, 0.8%, 0.9% or 1.0%.

In some embodiments, a volume of an aqueous solution (e.g., water or an aqueous buffer comprising dye) is 1 µl to 10 µl, or more. For example, a volume of an aqueous solution may be 1 µl, 1.5 µl, 2 µl, 2.5 µl, 3 µl, 3.5 µl, 4 µl, 4.5 µl, 5 µl, 5.5 µl, 6 µl, 6.5 µl, 7 µl, 7.5 µl, 8 µl, 8.5 µl, 9 µl, 9.5 µl or 10 µl.

Positive controls of the present disclosure are produced from samples (e.g. urine samples) known to contain misfolded proteins. Likewise, negative controls of the present disclosure are obtained from samples (e.g. urine samples) known to not contain misfolded proteins or from water, saline, phosphate buffer saline (PBS) or other salt solution not containing misfolded proteins. The conditions under which a positive and/or negative control is produced are similar to the conditions under which a method of the present disclosure is performed for the particular urine sample being compared to the positive or negative control. For example, a test urine sample from a pregnant woman is compared to a urine sample with misfolded proteins from a pregnant woman (positive control) and/or to a urine sample without misfolded proteins from a pregnant woman (negative control). If results obtained with the test sample are comparable to results obtained with a positive control, then the test sample is determined to contain misfolded proteins. If results obtained with the test sample are comparable to results obtained with a negative control, then the test sample is determined to not contain misfolded proteins. Further, the type of surface comprising cellulose (e.g., plain paper) used in a method of producing a positive and/or negative control is the same as the type of surface comprising cellulose used in a method of assessing a test urine sample. It should also be understood that the volume of solution as well as the type (e.g., Congo Red) and concentration of dye (or dyes) used in a method of producing a positive and/or negative control is the same as the volume of solution as well as the type and concentration of dye (or dyes) used in a method of assessing a test urine sample.

In some embodiments, positive and negative results for comparison to the test sample results are provided as images in the test kit.

Some methods of the present disclosure include additional steps for confirming whether or not a sample (e.g. urine sample) from a subject (e.g., pregnant woman) contains misfolded proteins. For example, after a urine sample from a subject is identified as containing misfolded proteins, an additional, diluted urine sample may be similarly assessed. This can be done in at least two ways. In one instance, a first urine sample is obtained (e.g., using clean catch) obtained from a subject, and a first portion of that first urine sample is assessed for the presence of misfolded proteins. Then, a second portion of that first sample is similarly assessed for the presence of misfolded proteins. The second portion may be diluted then similarly assessed for the presence of misfolded proteins. A determination that both the first and second portions (diluted or undiluted) of urine from the first urine sample have misfolded proteins can serve as confirmation that the subject has urine with misfolded proteins. Alternatively, a first urine sample is obtained (e.g., using clean catch), and a portion of that first urine sample is assessed for the presence of misfolded proteins. Then, after a period of time (e.g., a couple of hours), a second urine sample is collected from the same subject, and a portion of that second urine sample is similarly assessed for the presence of misfolded proteins. The second portion may be diluted then similarly assessed for the presence of misfolded proteins A determination that both the first and second samples of urine (diluted or undiluted) from the same subject have misfolded proteins can serve as confirmation that the subject has urine with misfolded proteins.

Some aspects of the present disclosure include combining a sample (e.g. a urine sample) from a pregnant woman with a first dye that binds misfolded proteins and e.g., cellulose and a second dye that is a different color from the first dye and does not bind misfolded proteins and cellulose, thereby producing a solution of urine and two dyes. Typically, the color of one dye is visually distinct from the color of the other dye. For example, the first dye may be red and the second dye may be blue. In some embodiments, the first dye is Congo Red. In some embodiments, the second dye is a water soluble dye such as erioglaucine (also referred to as FD & C Blue No. 1, a food coloring). Other water soluble dyes (e.g., other FD & C colors) may be used as a second dye that does not bind misfolded proteins and cellulose, including, without limitation, FD & C Red No. 40, FD & C Yellow No. 5, FD & C Yellow No. 6, FD & C Blue No. 2, FD & C Red No. 3, or FD & C Green No. 3.

In some embodiments, a correlation coefficient, p, is used to distinguish between non-preeclampsia samples (e.g. urine samples) and preeclampsia samples (e.g. urine samples). The exact cut-off of the correlation coefficient, p, that best discriminates non-preeclampsia urine samples from preeclampsia urine samples is defined by testing a large set of urine samples from pregnant women without preeclampsia, pregnant women with preeclampsia, and pregnant women with other pregnancy conditions. In some embodiments, a correlation coefficient, $\rho$, of 0.5 or greater (e.g., 0.5 to 1.0) is indicative of preeclampsia. For example, a $\rho$ of 0.5, 0.6, 0.7, 0.8, 0.9 or 1.0 is indicative of suitable paper.

In some embodiments, correlation coefficient is calculated using an algorithm. The algorithm, in some embodiments, is programmed as a mobile telephone or tablet application. The algorithm, in some embodiments, compensates for illumination, subtracts the white background, and then calculates the correlation coefficient between the different color channels (e.g., red and blue channels) of the color image of the diffused spot. The correlation coefficient between channels is significantly different between non-preeclamptic sample (e.g. urine sample) and preeclamptic sample (e.g. urine sample). This information can be used, for example, in calibration and screening applications (e.g., software applications) as follows.

Calibration: The goal of calibration application is to help the user choose a surface, such as a cellulosic surface (e.g., paper), and choose the concentrations of dyes (e.g., Congo Red and blue food dye) for robust discrimination between normal and preeclamptic sample (e.g. urine sample). Two criteria may be used: (1) sufficient signal in both color channels so that camera noise does not influence the correlation calculation; and (2) fiber structure of the surface (e.g., paper), which should permit the second dye (e.g., the blue food dye) to spread uniformly, while allowing the first dye when not bound to misfolded proteins (e.g., the Congo Red dye) to bind. Thus, the appropriate surface (e.g., paper) and dye concentration choice should give a balanced signal in both color channels (e.g., red and blue channels) as well as a large difference in correlation coefficients between non-preeclamptic and preeclamptic samples (e.g. urine samples).

The calibration procedure works, in some embodiments, by carefully introducing different concentrations of the first dye (e.g., Congo Red) and the second dye (e.g., blue food dye) in non-preeclamptic and preeclamptic samples (e.g., urine samples), applying drops of the mixtures on different surfaces (e.g., papers), allowing the samples to diffuse, and taking photographs of the diffused samples (see FIGS. 27A and 27B). Calibration software measures the percentage difference of the signals of the two channels (e.g., red and blue channel) and the correlation coefficient between the two channels. A plot of the correlation coefficient and the percentage signal difference reveals which concentrations and surfaces (e.g., papers) are suitable for use. In FIGS. 27A and 27B, for example, different ratios of Congo Red/blue dye were used to test non-preeclamptic urine (a) and preeclampsia urine (b) and any of the Congo Red/blue dye results from sample 2 to sample 7 are acceptable because the signal difference between the red and blue channels is less than the signal difference for example in samples 8 and 9, and the red channel-blue channel correlation coefficients are sufficiently different for non-preeclamptic urine and preeclamptic urine.

Screening: Once the surface (e.g., paper) and dye concentrations are calibrated, the kit and optionally including the software application ("app") can be used for screening for misfolded proteins. After the urine is mixed with the first and second dye, for example, and a drop of the mixture is diffused on a cellulosic surface, a photo of the diffused sample (e.g., drop) is captured by, for example, a smartphone or tablet camera. The software application then uses the white background to estimate and compensate for illumination color. Next, the background is subtracted out from the image so that only the pixels corresponding to the sample survive. The correlation coefficient between the two color channels (e.g., red and blue channels) is then calculated and compared to a threshold to indicate the presence of misfolded proteins. In some embodiments, a correlation coefficient threshold of 0.5 to 1.0 (e.g., 0.85) distinguishes between normal and preeclamptic urine, as exemplified in FIGS. 27A and 27B.

Some aspects of the present disclosure provide compositions and kits for detecting misfolded proteins in samples (e.g. urine samples). Such compositions and kits, in some embodiments, may be used to diagnose preeclampsia. Non-limiting examples of kits of the present disclosure are shown in FIGS. 25A and 25B and in FIGS. 26A and 26B.

Figure 25A:
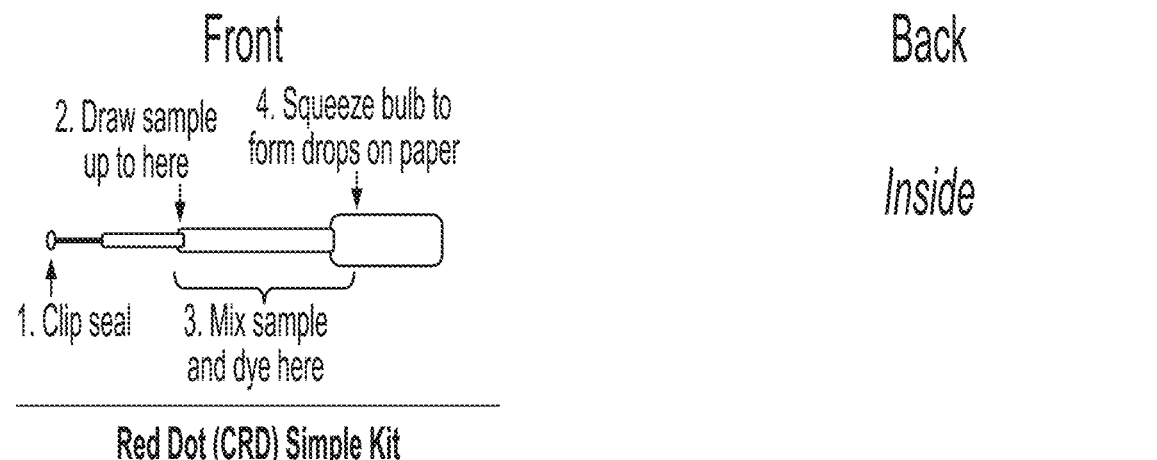
FIGS. 25A-25B depict an example of a Congo Red Dot Simple Kit of the present disclosure.
Figure 25B:
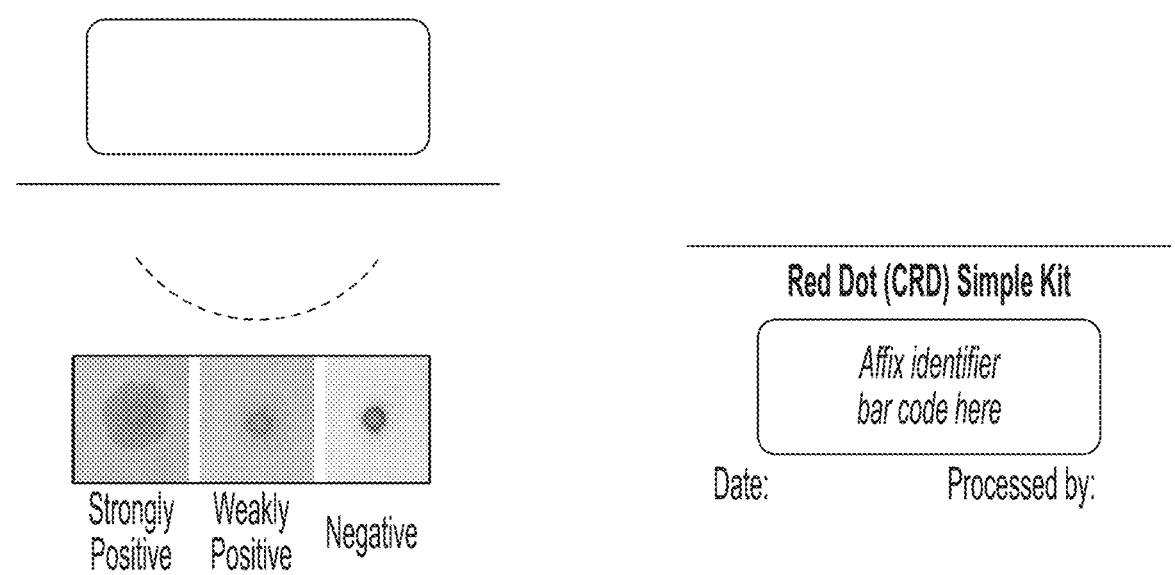

FIGS. 25A and 25A depict the interior of an example of a tri-fold configured Congo Red Dot Simple Kit and a Congo Red Dot Quant Kit, respectively, with a top panel, middle panel and bottom panel made from, for example, cardstock. When in the "folded" configuration, a pouch is formed with the middle panel covered by the top and bottom panels. A curved slit in the bottom panel (represented by a curved dotted line) is positioned and sized to receive the folded flap closing the pouch.

The top panel of FIG. 25A shows a disposable pipette that may be provided in the kit. The pipette may be preloaded with dye (e.g., 5 µl of a 0.5% solution of Congo Red, or 5 µl of a 5% solution of Congo Red+2.5 µl of a 0.1% solution of erioglaucine) and sealed. The pipette may then be secured in the middle panel by pre-formed slits (represented by two straight dotted lines). The slits are positioned such that the tip of the pipetted with the preloaded dye (or two dyes) remains inside the pouch and protected from light. Provided with the kit, in some instances, is a device for clipping the sealed end of the pipette (e.g., a nail clipper or small pair of scissors).

Below the pipette is an area to which a surface comprising cellulose is provided for sample testing. The surface by be affixed (e.g., a self-adhesive paper label) to the kit trifold. In some embodiments, the surface is provided with the kit. In other embodiments, the surface is provided separately. For each clinical site, the surface may require separate validation for suitability, accounting for, for example, differences in environmental conditions, such as humidity and temperature.

The bottom panel contains a series of images of controls for a strongly positive sample, a weakly positive sample and a negative sample. The test sample may be compared to any one or more of the controls to determine sample result.

Figure 26A:
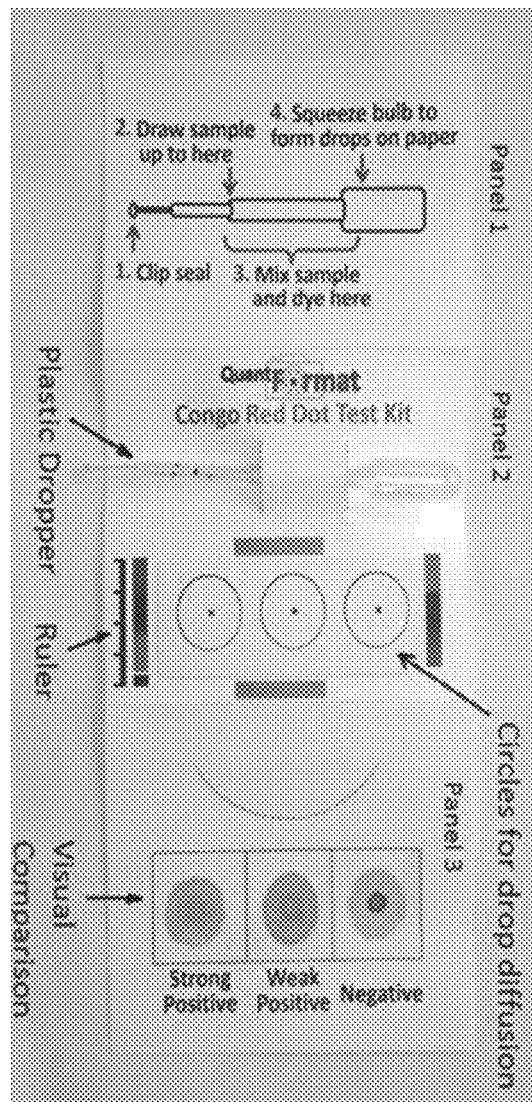
FIGS. 26A-26B depicts an example of a Congo Red Dot Quant Kit of the present disclosure.
Figure 26B:

The kit depicted in FIG. 26A further includes color calibration scales (represented by graded bars flanking at left and right of test surface designed to orient the picture and correct for any light gradient. Excess green (represented by bars flanking at top and bottom of test surface) compensates for any tendency of a camera to adjust color.

An example of an array kit is depicted in FIG. 3C and in FIG. 4(1). In some embodiments, a Congo Red Dot Quant Array Kit is an extension of the Congo Red Dot Quant Kit in that the kit is basically the same with the exception that it provides for the assessment of multiple test samples on a single surface (e.g., cellulosic surface).

Thus, various aspects and embodiments of the present disclosure provide diagnostic methods and kits that can be used for efficient and accurate detection of misfolded proteins in urine (or other sample), which, in some cases, is indicative of certain disorders (e.g., preeclampsia in cases where the test sample is urine obtained from a pregnant woman).

EXAMPLES

Example 1

The experiments presented in this example were directed to the development of simple diagnostic methods and compositions (e.g., kits) for rapid and accurate identification of misfolded proteins in e.g., urine. In pregnant women, the presence of misfolded proteins in urine can be used as an indication of preeclampsia. The existing Congo Red Dot test is an effective test that can be used as a diagnostic and prognostic tool for preeclampsia. Nonetheless, the Congo Red Dot test, which typically utilizes relatively expensive reagents such as nitrocellulose and alcohol washes, takes approximately 5 hours to complete. One of the objectives of this study was to produce simplified, low-cost and efficient diagnostic methods and compositions that can be implemented, for example, at the point of care, for example at a pregnancy checkup with a healthcare provider and is also suitable for low-resource setting. Toward this objective, provided herein, in some embodiments, are simplified, paper-based methods and compositions that provide low-cost, semi-quantitative results, for example, within 2 minutes, or quantitative results, for example, within 7 minutes.

As an initial step toward developing a simplified paper-method for diagnosing preeclampsia, the "suitability" of over fifty different types of paper was analyzed. Surprisingly, not all paper is suitable for use as a surface for detecting misfolded proteins bound by, for example, Congo Red. The analyses herein showed that cellulosic surfaces, such as, for example, plain paper, participate actively in the chemistry of the Congo Red Dot test. The chemistry behind this paper chromatography is complex. Congo Red binds to cellulose fibers through hydrogen bonds with the cellulosic free hydroxyl groups. Due to its planar molecular configuration, Congo Red then intercalates between the cellulose fibers. The same principle applies to misfolded proteins which, due to the abundance of β-sheets, have similar spatial arrangement with cellulose fibers. Nitrocellulose, in contrast, has hydroxyl groups that have been esterified through reaction with nitric acid. Being already occupied, the hydroxyl groups no longer bind Congo Red, and, thus, nitrocellulose does not bind Congo Red—it is largely inert. Without being bound by theory, a cellulosic surface (e.g., plain paper) competes with misfolded proteins of a urine sample for Congo Red binding. In urine samples that do not contain misfolded proteins, Congo Red is free in solution. When spotted on a porous, cellulosic surface, this free Congo Red forms hydrogen bonds with cellulose, thus slowing down its flow through the surface (referred to herein as "Congo Red retardation").

Paper suitability is based, at least in part, on contact angle of the paper, fluorescence of the paper, which is a reflection of additives, and porosity of paper, ambience (e.g., temperature and humidity of environment/region). As the flow of liquid over porous surfaces (e.g., paper) is a complex process governed by physical laws (e.g., Fick's law and Stokes-Einstein relation), a software routine was designed to determine paper "suitability" for Congo Red Dot testing based on a correlation coefficient (Rho, $\rho$) between suitable paper and unsuitable paper. The exact cut-off of the correlation coefficient, $\rho$, between suitable paper and unsuitable paper is defined by determining the relationship of $\rho$ with the contact angle, $\theta$, on different types of "plain" paper. Electrolyte and protein concentrations are varied in vitro. Contact angle, $\theta$, is likely a significant determinant of $\rho$ and is less affected by electrolyte and protein concentration. In some embodiments, a $\rho$ of 0.5 or less (e.g., 0.1 to 0.5) is indicative of suitable paper. For example, a $\rho$ of 0.1, 0.2, 0.3, 0.4 or 0.5 is indicative of suitable paper.

Congo Red Dot Simple Method and Kit

After analyzing fifty different types of paper, a particular type with an adhesive backing was chosen, in part because results obtained using the particular paper were more consistent relative to other types of paper tested, possibly due to lack of wrinkling when wet. Urine samples from a pregnant woman with severe preeclampsia (sPE) (FIG. 1, "Sample," Case 1), from a pregnant woman with preeclampsia (FIG. 1, "Sample," Case 2), and from a pregnant woman without preeclampsia (FIG. 1, "Sample," Case 3, control) were first mixed with Congo Red and then applied to plain paper. Water mixed with Congo Red was used as a control (FIG. 1, "Blank," Cases 1-3). In the sample of water (FIG. 1, "Blank," Case 3) and in the non-preeclampsia control samples (FIG. 1 "Sample," Case 3), Congo Red remained tightly centered around the application point, while clear fluid spread out slowly. In samples from the woman with preeclampsia (FIG. 1, "Sample," Case 2), Congo Red spread out along with the clear fluid, generating a pink enlarged halo encircling the visible application point in the center (FIG. 1, "Sample," Case 2). In samples from the woman with severe preeclampsia (e.g., "highly positive" samples) (FIG. 1, "Samples, Case 1), Congo Red and the sample formed a homogenous intensely pink enlarged spot extending beyond the initial sample application spot. In experiments (n=78), a significant correlation between Congo Red and a 3-level visual score (P<0.001) was noted. The results from this example showed marked differences in chemistries between Congo Red-treated preeclampsia urine and Congo Red-treated non-preeclampsia urine with respect to their interactions with the plain paper.

As all bonds are saturable, the size of the formed circle depends on many factors, including, for example, paper wettability (e.g., measured by the contact angle 0) and Congo Red concentration. Without being bound by theory, if the paper has a low contact angle (e.g., paper towel), there is not enough time for hydrogen bonding, and, thus, the sample spreads too fast and Congo Red retardation is not apparent (data not shown). In contrast, if the paper has a high contact angle (e.g., glossy coated paper), the sample does not spread and dries in the spot (data not shown). If the sample contains misfolded proteins (e.g., aggregates of misfolded protein), then Congo Red intercalates proportionally with the concentration of the misfolded proteins. When such sample is applied to a cellulosic surface, there is little or no Congo Red available for cellulose binding, as most of it has bound with misfolded proteins while in solution. The result is the formation of a characteristic wide pink circle, resulting from the spreading of the misfolded proteins (FIG. 1, "Sample," Case 1). A homogenously pink circle appears if all Congo Red is engaged in misfolded proteins (FIG. 1, "Sample," Case 1), and a tight central circle appears within a homogeneous pink halo if free Congo Red is available for bonding to cellulose (FIG. 1, "Sample," Case 2).

Based on the results provided herein, two simplified diagnostic kits for preeclampsia were designed. The first kit, referred to as the Congo Red Dot Simple Kit (for rapid (e.g., 1 to 3 minute)), may be used for subjective assessment of urine congophilia. The second kit, referred to as the Congo Red Dot Quant Kit, may be used for objective quantification of results and is enabled by a software algorithm that measures "spot homogeneity." Development of the Congo Red Dot Quant Method and Kit is described below.

Congo Red Dot Quant Method and Kit

Most of the urine samples from pregnant women without preeclampsia dry clear (or almost clear) when applied to a cellulosic surface such as plain paper, and, thus, there is no measure of how far a sample would have spread on such a surface. To address this issue, the Congo Red Dot Quant Kit was designed with a dual dye mix using red and blue dyes. The blue color was selected as complementary to the color of Congo Red in the RGB (Red Green Blue) color space. The RGB color model is related to the physiology of human eye and brain and not to colorimetrically defined colors. It is also the typical output of mobile telephone (e.g., smartphone) cameras. Out of several blue dyes tested, erioglaucine (FD&C blue 1, non-toxic dye, McCormick & Co.) was selected for quantification of Congo Red spreading/retardation by image analysis, and, thus, discrimination of preeclampsia cases from non-preeclampsia cases. The blue dye migrates with the water phase, marking the maximum spread area (see, e.g., FIG. 2, "Normal," top row). The optimal composition of the dual dye was determined to be a 2:1 mix of 5% Congo Red:10% erioglaucine, with 3 µl of the dual dye mix added per 100 µl volume of urine.

Figure 2:
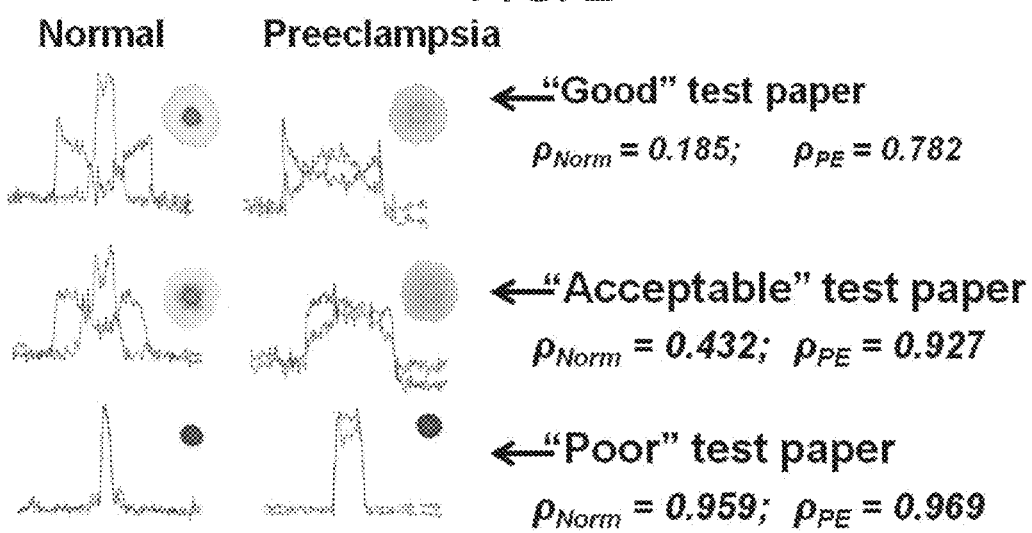
FIG. 2 shows a comparison of examples of a "Good" test paper, an "Acceptable" test paper, and a "Poor" test paper. The examples shown serve as a basis for an algorithm that assesses the correlation coefficient (p) between the signal in different color channels, in this particular case, the red and the blue channels, of pictures taken with a smartphone. The $\rho_{Norm}$ calculation is based on a sample from a pregnant woman without preeclampsia; the $\rho_{PE}$ calculation is based on a sample from a pregnant woman with preeclampsia.

Next, an image analysis algorithm was created (e.g., in MATLAB), which extracts the correlation coefficient (Rho, $\rho$) between the signal in the red and blue channels of a mobile telephone-acquired image or a tablet-acquired image (FIG. 2). The correlation coefficient is calculated after preprocessing to compensate for illuminant and paper color. The exact cut-off of the correlation coefficient, $\rho$, that best discriminates non-preeclampsia urine samples from preeclampsia urine samples is defined by testing a large set of urine samples from pregnant women without preeclampsia, pregnant women with preeclampsia, and pregnant women with other pregnancy conditions. To this end, stored urine samples retrieved from women with well-characterized diagnoses and pregnancy outcomes are used (e.g., 824 urine samples from 662 women are available, stored at −80° C.). A comparative accuracy analysis is conducted relative to P/C ratio (results for all samples were available) and the dipstick test, which is read both visually and objectively using the Siemens Clinitek Status reader. In addition, algorithms, such as machine-learning algorithms (e.g., support vector machines), variational analysis, and/or a non-parametric Bayesian technique, are used to determine if other image analysis parameters (e.g., aside from the correlation coefficient of red and blue pixels in the space of spread) can further improve patient classification. Further, the image processing may be carried out on a remote server instead of the mobile telephone or tablet and the results reported back to the user.

Example 2

Figure 5:
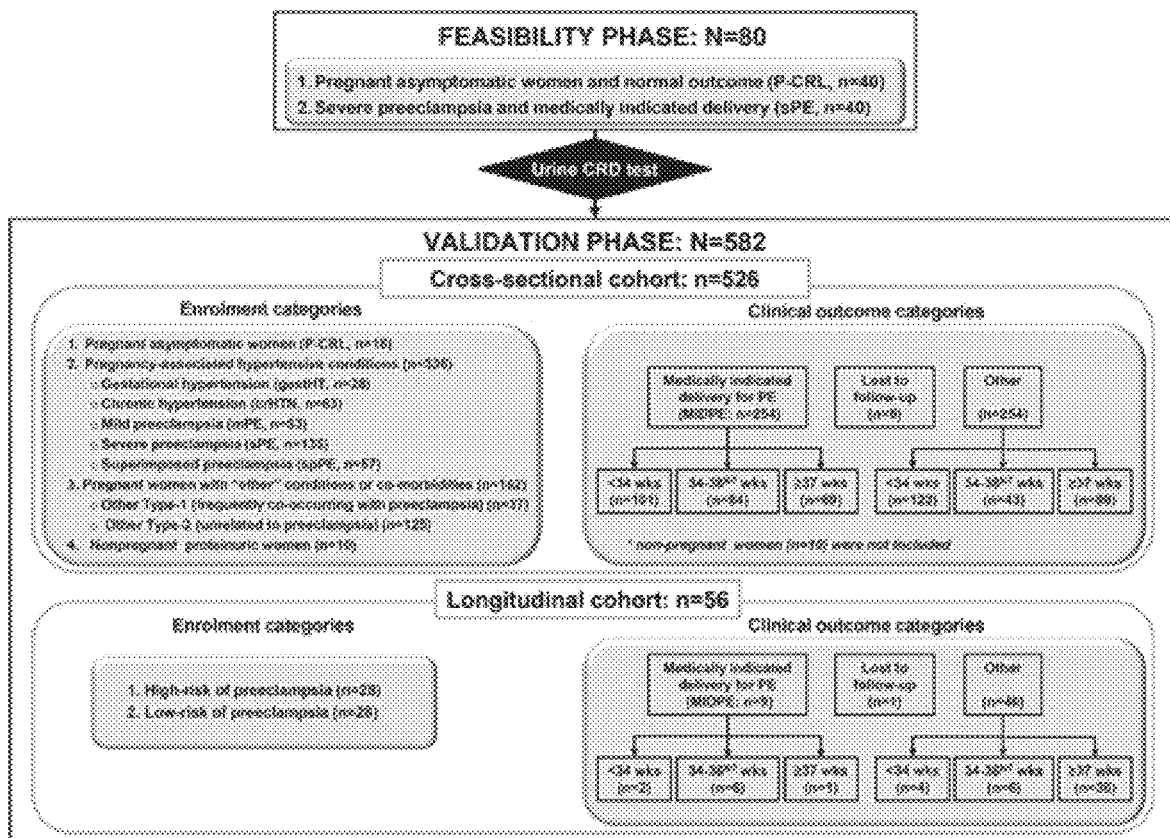
FIG. 5 shows a flow chart of the study design and women who donated urine samples for a Congo Red Dot test of Example 2.

Women with Severe Preeclampsia (sPE) Exhibit Urine Congophilia with Spectral Features of Amyloid-Like Aggregates A stringent study design was employed, which involved a feasibility and a validation phase (FIG. 5). As initial proof of principle (feasibility), urine samples from pregnant women (n=80) with precise clinical classifications and known outcomes were tested: 40 severe preeclampsia (sPE) women required medically-indicated delivery for preeclampsia (MIDPE) and 40 healthy pregnant control (P-CRL) women who had an uncomplicated gestation and delivered at term. Their clinical characteristics are included in Table 1.

TABLE 1

Demographic, clinical and outcome characteristics of women whose urine samples were used in the feasibility phase (n = 80).

| Variable | Severe Preeclampsia (sPE, n = 40) | Pregnant Control (P-CRL, n = 40) | P value |
|---|---|---|---|
| Maternal characteristics at enrollment | | | |
| Age, years † | 28 ± 1 | 27 ± 1 | 0.373 |
| Non-Caucasian race, n (%) § | 20 (50) | 24 (55) | 0.500 |
| Weight, kg † | 89 ± 3 | 84 ± 4 | 0.380 |
| Nulliparity, n (%) § | 25 (63) | 19 (48) | 0.261 |
| Gestational age, weeks † | 30 ± 1 | 30 ± 1 | 0.817 |
| Systolic blood pressure, mmHg ‡ | 165 ± 3 | 113 ± 3 | <0.001 |
| Diastolic blood pressure, mmHg ‡ | 99 ± 2 | 66 ± 1 | <0.001 |
| Neurological manifestations, n (%) § | 21 (53) | 0 (0) | <0.001 |
| Proteinuria, urinary dipstick ‡ | 3 [2-4] | 0 [0-0] | <0.001 |
| 24 h-protein completed, n (%) | 27 (68) | NA | NA |
| 24 h-protein excretion, grams/24 h ‡ | 2.6 [1.5-3.6] | NA | NA |
| Outcome characteristics | | | |
| HELLP, n (%) § | 8 (20) | 0 (0) | 0.005 |
| IUGR, n (%) § | 11 (28) | 0 (0) | <0.001 |
| Gestational age at delivery, weeks † | 30 ± 1 | 39 ± 1 | <0.001 |

TABLE 1-continued

Demographic, clinical and outcome characteristics of women whose urine samples were used in the feasibility phase (n = 80).

| Variable | Severe Preeclampsia (sPE, n = 40) | Pregnant Control (P-CRL, n = 40) | P value |
|---|---|---|---|
| Delivery <34 weeks, n (%) § | 39 (98) | 0 (0) | <0.001 |
| Indicated delivery for PE, n (%) § | 40 (100) | 0 (0) | <0.001 |
| Birthweight, grams, n (%) § | 1,217 ± 78 | 3,318 ± 80 | <0.001 |
| Cesarean delivery, n (%) § | 37 (93) | 16 (40) | <0.001 |

† Data presented as mean ± standard error and analyzed by Student t-tests.
‡ Data presented as median [interquartile range] and analyzed by Mann-Whitney tests.
§ Data presented as n (%) and analyzed by Fisher's exact tests.

Urine that had been mixed with Congo Red (CR) was spotted on an unsupported nitrocellulose membrane, and then washed with increasing concentrations of methanol (FIG. 6A). The rationale of this experiment was based on the self-assembling property of CR and its ability to initiate formation of large insoluble oligomers following binding to amyloid proteins that have an extensive β-sheet structure. As shown, spots of sPE but not P-CRL women remained red after the methanol wash, indicating that women with PE display urinary congophilia. A standardized protocol was further designed to allow an objective quantification of each urine sample propensity to retain CR, while minimizing variations due to differences in proteinuria and hydration status (the Congo Red Dot [CRD] test). Two indices were obtained through image analysis: CR Retention (CRR, measure of congophilia) and CR Incorporation (CRI, internal reference). Compared to P-CRL, CRR was significantly increased in sPE urine (P<0.001, FIG. 6B). No differences in CRI were noted between the two groups (FIG. 6C). In receiver operating curve characteristic (ROC) analysis, a CRR cut-off value of 15% had 100% [95% CI: 92-100] sensitivity and 100% [95% CI: 92-100] specificity to discriminate sPE cases from P-CRLs. In the feasibility cohort, all sPE patients had CRR values >15%. Based on this result, CRR≥15% was considered "non-reassuring" (NR-CRR).

Figure 6D:
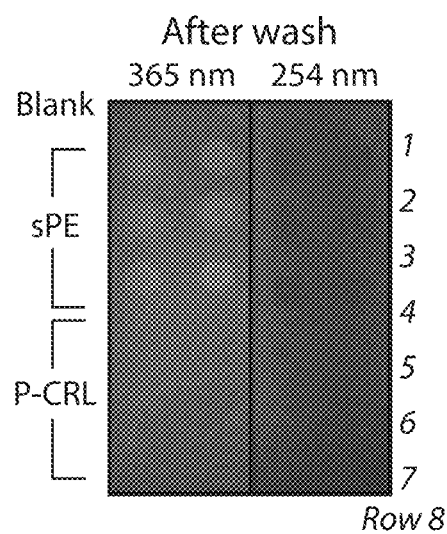
Figure 6E:
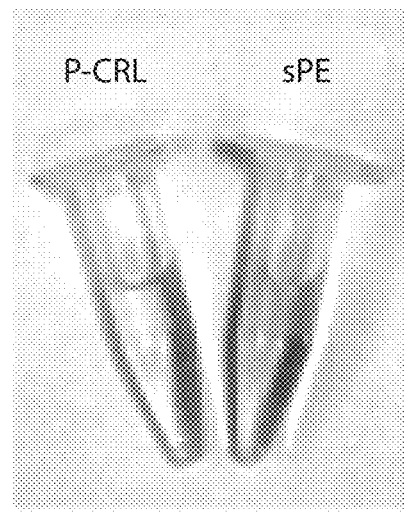
Figure 6F:
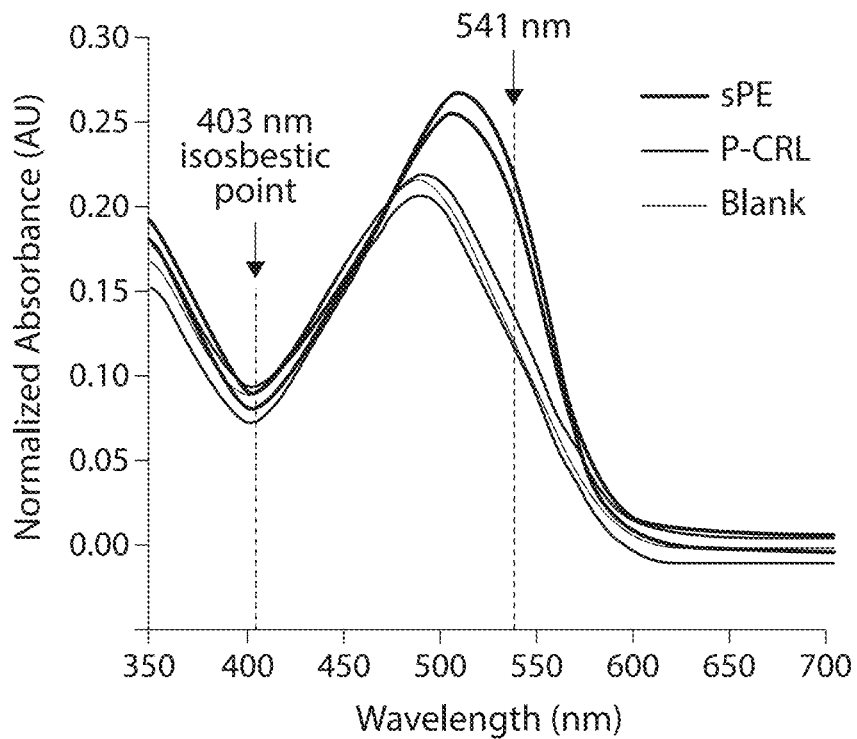
Figure 6G:
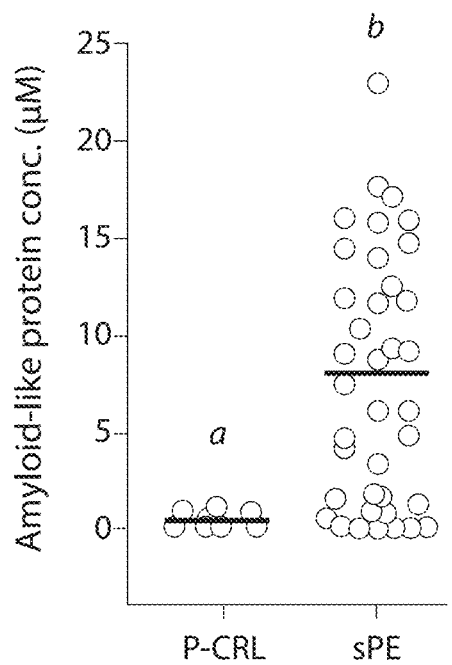
Figure 6H:
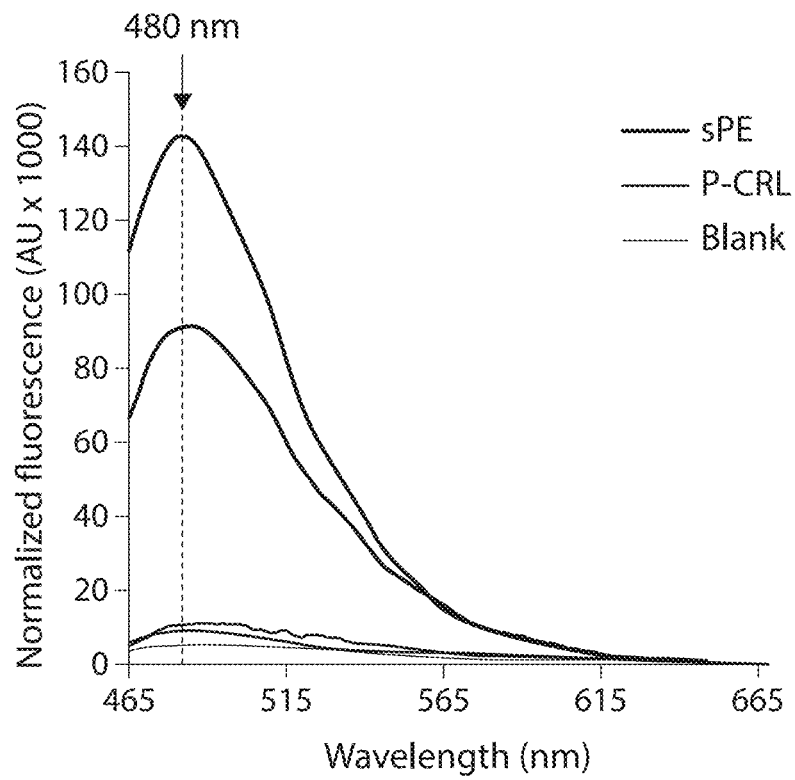
Figure 6I:
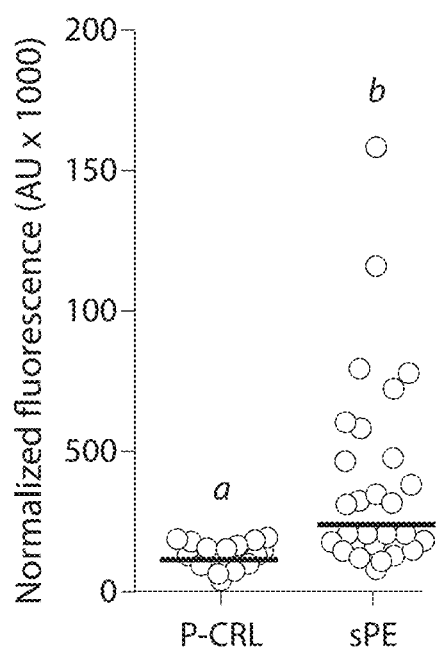

CR-bound amyloids exhibit bright red fluorescence when illuminated with UV light, along with a shift in absorbance from about 490 to 540 nm. Upon illumination of the nitrocellulose membrane with long- but not short-wavelength UV, the characteristic red fluorescence of amyloid-bound CR was observed (FIG. 6D). Immediately upon addition of CR stock solution, 30% (12/40) of sPE urine samples (but no P-CRLs) changed visibly in color from orange-red to magenta (FIG. 6E), consistent with the bathochromic spectral shift described for β-amyloid oligomerization (aggregation), in vitro. Spectrophotometric determination of absorbencies at 403 nm (isobestic point) and 541 nm (point of maximal shift) confirmed presence of amyloid-like aggregates in sPE urine (FIG. 6F). Among sPE women, the degree of spectral shift correlated with the CRR index (r=0.664, P<0.001). Although, as a group, sPE women had higher concentration of amyloid-like aggregates, 20% (8/40) of sPE urines did not exhibit a detectable (visual and/or spectrophotometric) spectral shift despite NR-CRR at the CRD test (FIG. 6G). A spectrophotometrically detectable shift occurred only for samples with CRR>50%, implying that compared to CRD test (CRR cut-off 15%), direct spectrophotometry has a lower sensitivity (80% [95% CI:64-91]) in identifying PE (P=0.007, feasibility cohort). In addition, sPE women exhibited increased urine Thioflavin T-induced (ThT) fluorescence (FIG. 6H), P<0.001. This is yet another indicator of amyloid-like structures present in the urine of women with PE. Similar to direct spectrophotometry, only a subgroup of sPE specimens (42%) showed a significant increase in fluorescence at 485 nm upon ThT binding (FIG. 6I). Compared to the CRD test, urine ThT binding had a lower sensitivity (82% [95% CI:65-92]) in identifying PE (P<0.001, feasibility cohort).

Urine Congophilia Differs Among Hypertensive Pregnancy Disorders and Increases with PE Severity To further understand the clinical significance of urine congophilia during pregnancy, urine samples from an additional 582 women were tested, this time unselected with respect to enrollment category (FIG. 5, validation phase). A cross-sectional (n=526), and a longitudinal (n=56) cohort were designed. Women in the cross-sectional cohort participated with a single urine sample. The results were grouped and analyzed based on clinical classification at sample collection and pregnancy outcome (MIDPE or Other). The clinical characteristics of the women included in the cross-sectional cohort are presented in Table 2. Women in the longitudinal cohort were asymptomatic for PE at study entry, and were followed longitudinally throughout gestation.

TABLE 2

Demographic, clinical and outcome characteristics of pregnant women whose urine samples were used in the cross-sectional validation phase (n = 516)

| | | Other | | | | | | | | |
|---|---|---|---|---|---|---|---|---|---|---|
| Variable | P-CRL n = 18 | Type-1 n = 37 | Type-2 n = 125 | gestHT n = 28 | crHTN n = 63 | mPE n = 53 | sPE n = 135 | spPE n = 57 | P value |

Demographic and clinical characteristics at sample collection

| Age, years ‡ | 29 [25-32] | 26 [22-32] | 28 [23-32] | 30 [22-36] | 34 [30-37]°° | 27 [21-32] | 26 [21-33] | 31 [26-35]° | <0.001 |
| Non-Caucasian race, n (%)§ | 10 (56) | 18 (49) | 64 (51) | 18 (64) | 47 (75) | 26 (49) | 86 (64) | 41 (72) | 0.009 |
| Weight, kg ‡ | 85 [59-91] | 73 [58-131] | 82 [70-86] | 92 [70-116] | 107 [84-117] | 85 [73-124] | 81 [69-100] | 94 [78-115] | 0.059 |
| Nulliparity, n (%)‡ | 7 (39) | 24 (65)° | 52 (42) | 16 (57) | 15 (24)° | 33 (62)° | 84 (62)° | 20 (35)° | <0.001 |
| Multiple gestation, n (%)§ | 0 (0) | 4 (11) | 15 (12) | 3 (10) | 4 (6) | 4 (8) | 9 (7) | 1 (2) | 0.270 |
| Gestational age, weeks ‡ | 30 [12-37] | 27 [25-32]° | 29 [25-32]° | 37 [35-38]° | 32 [25-35] | 36 [34-38]° | 34 [30-37] | 33 [27-36] | <0.001 |
| Gestational age intervals, n (%) | | | | | | | | | |
| <20 weeks | 5 (28) | 1 (3) | 2 (2) | 0 (0) | 5 (8) | 0 (0) | 0 (0) | 0 (0) | <0.001 |
| 20-34⁶⁄⁷ weeks | 5 (28) | 28 (76) | 118 (94) | 6 (21) | 37 (59) | 9 (17) | 59 (44) | 29 (51) | |
| 34-36⁶⁄⁷ weeks | 4 (22) | 6 (16) | 2 (2) | 7 (25) | 12 (19) | 21 (19) | 38 (28) | 22 (39) | |
| ≥37 weeks | 4 (22) | 2 (5) | 3 (2) | 15 (54) | 9 (14) | 9 (14) | 38 (28) | 6 (10) | |
| Systolic blood pressure, mmHg ‡ | 110 [99-120]° | 113 [109-131]° | 113 [109-122]° | 150 [143-159]° | 150 [132-168]° | 148 [140-158]° | 160 [150-170]° | 162 [150-176]° | <0.001 |
| Diastolic blood pressure, mmHg ‡ | 65 [60-70]° | 72 [65-81]° | 64 [60-71]° | 95 [89-101]° | 90 [78-100]° | 90 [87-98]° | 98 [90-104]° | 99 [92-104]° | <0.001 |
| Neurological manifestations, n (%) | 0 (0)° | 2 (5)° | 1 (1)° | 11 (39)° | 13 (21)°° | 8 (15)° | 21 (53)° | 63 (47)° | <0.001 |
| Proteinuria, urinary dipstick ‡ | 0 [0-0]° | 0 [0-1]° | 0 [0-0]° | 0 [0-0]° | 0 [0-1]° | 2 [1-2]° | 3 [1-3]° | 2 [1-3]° | <0.001 |
| 24 h-protein excretion, grams/24 h ‡ | NA | 0.32 [0.08-1.97]° | NA | 0.16 [0.10-0.19]° | 0.25 [0.14-0.45]° | 0.72 [0.34-1.61] | 2.01 [0.39-5.14] | 1.49 [0.55-3.57] | <0.001 |

Clinical course and pregnancy outcome

| Known pregnancy outcome, n (%)§ | 18 (100) | 36 (97) | 123 (98) | 28 (100) | 58 (92)° | 53 (100) | 135 (100) | 57 (100) | 0.023 |
| HELLP, n (%)§ | 0 (0)° | 2 (6)° | 0 (0)° | 0 (0)° | 1 (2)° | 0 (0)° | 28 (21)° | 6 (11) | <0.001 |
| IUGR, n (%)§ | 0 (0)° | 19 (54) | 0 (0)° | 0 (0)° | 4 (7) | 0 (0)° | 18 (13) | 9 (16) | <0.001 |
| IUFD, n (%)§ | 0 (0) | 1 (3) | 5 (4) | 0 (0) | 4 (7) | 0 (0) | 4 (3) | 1 (2) | 0.432 |
| Gestational age at delivery, weeks ‡ | 37 [36-39] | 31 [27-37]° | 33 [28-36]° | 37 [36-38]° | 35 [30-38] | 37 [36-39]° | 35 [30-37] | 33 [28-36]° | <0.001 |
| Delivery <34 weeks, n (%)§ | 3 (19) | 21 (58)° | 80 (66)° | 4 (14) | 21 (36) | 6 (11)° | 57 (42) | 29 (51) | <0.001 |
| Indicated delivery for PE, n (%)§ | 1 (6)° | 3 (9)° | 0 (0)° | 4 (14) | 17 (29)° | 41 (77)° | 132 (98)° | 56 (98)° | <0.001 |
| Birthweight, | 2,799 [1,321- | 1,150 [673- | 1,833 [963- | 2,280 [1,815- | 2,040 [1,240- | 2,891° [1,800- | 1,908 [1,050- | 1,395 [894- | 0.011 |

TABLE 2-continued

Demographic, clinical and outcome characteristics of pregnant women whose urine samples were used in the cross-sectional validation phase (n = 516)

| | | Other | | | | | | |
|---|---|---|---|---|---|---|---|---|
| Variable | P-CRL n = 18 | Type-1 n = 37 | Type-2 n = 125 | gestHT n = 28 | crHTN n = 63 | mPE n = 53 | sPE n = 135 | spPE n = 57 | P value |
| grams ‡ | 4,205] | 2,695] | 2,533] | 3,200] | 2,644] | 3,440] | 2,493] | 2,548] | <0.001 |
| Cesarean delivery, n (%)§ | 7 (39) | 22 (60) | 28 (22)ᵃ | 12 (43) | 24 (41) | 20 (38) | 808 (59) | 35 (61) | |

Figure 7A:
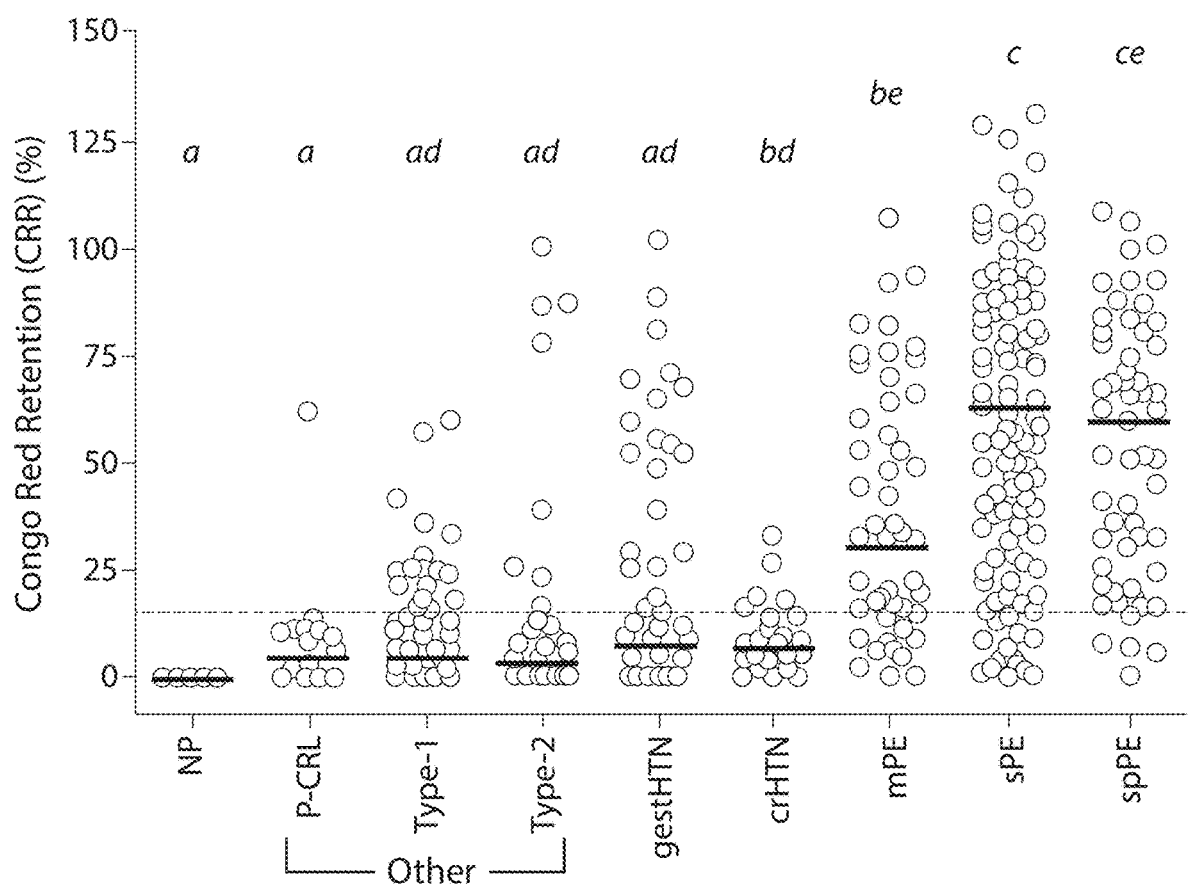
FIGS. 7A-7F show examples of diagnostic and prognostic features of urine congophilia.
Figure 7B:
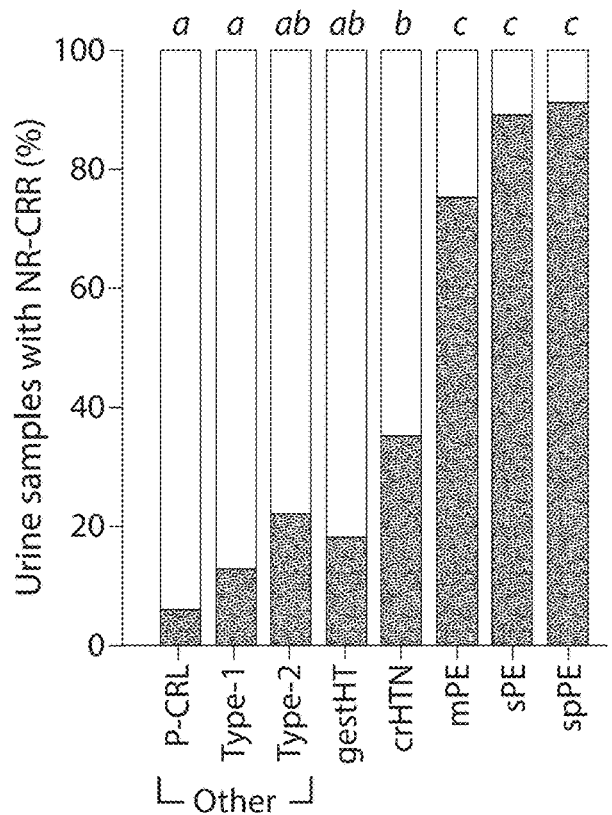
Figure 7C:
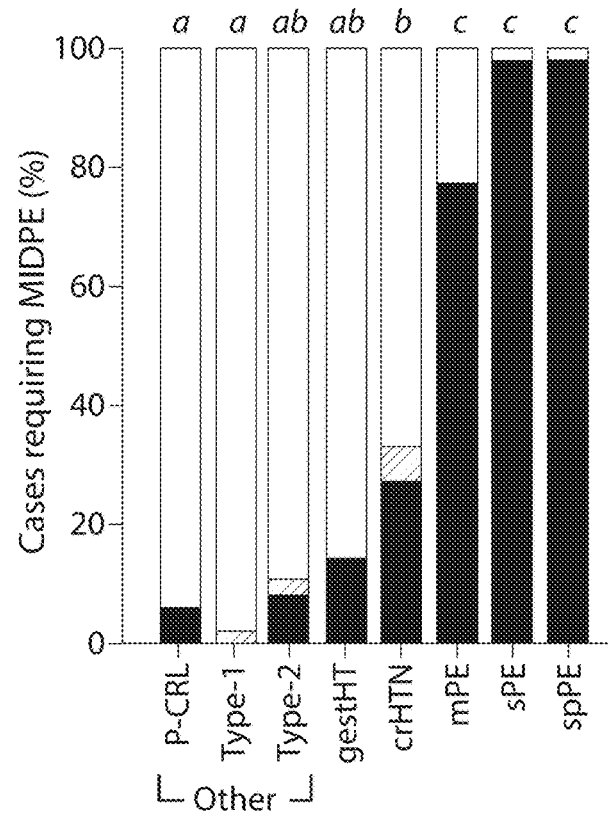
Figure 7D:
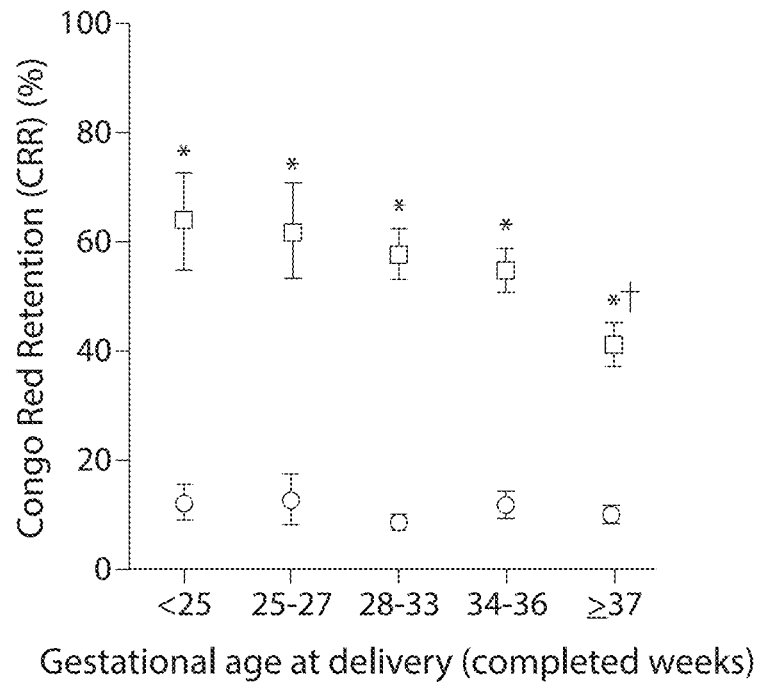

‡ Data presented as median [interquartile range] and analyzed by Kruskal-Wallis ANOVA followed by post-hoc comparisons using Dunn's test
§Data presented as n (%) and analyzed by Chi Square test exact tests
ᵃ $p < 0.05$ vs. P-CRL group; ᵇ $p < 0.05$ vs. sPE group
Abbreviations: P-CRL, pregnant control; gestHT, gestational hypertension; crHTN, chronic hypertension; mPE, mild preeclampsia; sPE, severe preeclampsia; spPE, superimposed preeclampsia; IUGR, intrauterine growth restriction; IUFD, intrauterine fetal death; HELLP, hemolytic, elevated liver enzymes, low platelets;

When cases enrolled in the cross-sectional cohort were grouped by clinical diagnosis at the time of sample collection, both sPE and superimposed PE (spPE) women had higher CRR levels compared to all other groups (FIG. 7A, P<0.001). Next, we analyzed the proportion of women displaying urine NR-CRR values was analyzed. We found that 75% (40/53), 89% (120/135), and 91% (52/57) of women admitted with a diagnosis of mild PE (mPE), sPE, and spPE, respectively had NR-CRR values (FIG. 7B). These proportions were significantly higher than in all the other groups (P<0.05). Of the chronic hypertension (crHTN) women ruled out for spPE based on clinical and laboratory criteria at the time of enrollment, 35% (22/63) displayed NR-CRR levels. This was significantly higher compared to P-CRLs (6%, 1/18, P=0.017) or women with pathologies unrelated to PE (Type-1: 13%, 16/125, P<0.001). Consistent with the progressing nature of PE, 27% (17/63) of women classified as crHTN at enrollment had their diagnosis revised to spPE and ultimately required MIDPE (FIG. 7C). Of these, 53% (9/17) had urine congophilia at the initial evaluation, implying that the CRD test may be useful for rapidly predicting spPE when this condition cannot be diagnosed based on the current clinical criteria alone. The relationship between the CRR index and MIDPE in the longitudinal cohort based on GA at delivery is presented in FIG. 7D. Women who required MIDPE had significantly higher CRR at all GA periods (MIDPE: P<0.001, GA: P=0.008). The CRR levels in preterm PE were significantly higher compared to term PE accompanied by a significant interaction between GA and MIDPE (2-way ANOVA, P<0.018). This observation may be explained by the higher proportion of women presenting with term mPE which by standard of care is managed by MIDPE without delay. Additionally, cases with high CRR values (CRR>60%) were less represented in women with term MIDPE compared to those requiring MIDPE at <34 weeks (29% vs 58%, P=0.003).

Figure 7E:
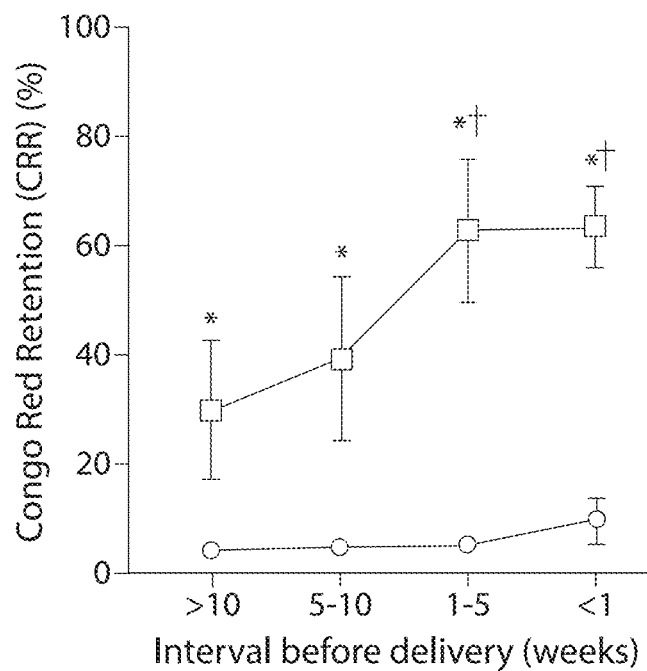

In the longitudinal cohort (FIG. 7E) women who developed PE requiring MIDPE (n=9, all from the high-risk enrollment group) had significantly higher CRR levels before clinical manifestation of the disease (P<0.001 for both MIDPE and interval-to-delivery). Interestingly, 78% (7/9) of these women had NR-CRR values at study entry that was over 10 weeks prior to clinically overt PE. This suggests that the underlying mechanism of urine congophilia likely occurs early in the asymptomatic phase and worsens progressively. Overall, 4 high-risk women displayed urine congophilia at <20 weeks GA and all had MIDPE. All the low-risk women (n=28) had a pregnancy course uncomplicated by PE, term delivery and all but one remained non-congophilic throughout pregnancy. This one case became congophilic in the third trimester and underwent indicated delivery for gestational hypertension (gestHT) at term.

Among low and high-risk women who did not develop PE there was no statistical difference in CRR levels at study entry (low risk: 3.2±0.6% vs. high risk: 7.0±2.8%, P=0.397). The Congo Red Dot (CRD) Test is a Simple Modality to Diagnose sPE and Predict MIDPE ROC analysis of enrollment urine samples (n=563) from the pregnant women included in the validation cohort who had known pregnancy outcomes (cross-sectional cohort subjects not lost to follow-up: n=508+longitudinal cohort subjects not lost to follow-up: n=55) determined that CRR alone (cut-off of >15%) had a sensitivity of 85.9% [95% CI: 81.1-89.9], specificity of 85.0% [95% CI: 80.4-88.8], positive likelihood ratio (LR) of 5.7 [95% CI: 4.4-7.5] and negative LR of 0.17 [95% CI: 0.1-0.2] in predicting PE requiring MIDPE (Table 3).

TABLE 3

Comparative prognostic accuracy for prediction of medically-indicated delivery for preeclampsia (MIDPE) among subjects in the validation phase with known pregnancy outcomes (n = 563)

| Characteristic | AUC [95% CI] | P value | Sens. (%) [95% CI] | Spec. (%) [95% CI] | +LR [95% CI] | −LR [95% CI] | PPV (%) [95% CI] | NPV (%) [95% CI] |
|---|---|---|---|---|---|---|---|---|
| CRR ≥ 15% | 0.894 [0.866-0.918] | <0.0001 | 85.93 [81.1-89.9] | 85.00 [80.4-88.8] | 5.73 [4.4-7.5] | 0.17 [0.1-0.2] | 83.4 [78.4-87.6] | 87.3 [83.0-90.9] |
| Dipstick † ≥ +1 | 0.825* [0.789-0.856] | <0.0001 | 81.89 [76.6-86.4] | 83.09 [7.1-87.3] | 4.84 [3.7-6.3] | 0.22 [0.2-0.3] | 81.9 [76.6-86.4] | 83.1 [78.1-87.3] |
| SBP ≥ 140 | 0.810* [0.775-0.842] | <0.0001 | 87.83 [83.3-91.5] | 74.33 [69.0-79.2] | 3.42 [2.8-4.2] | 0.16 [0.1-0.2] | 75.0 [69.8-79.7] | 87.5 [82.7-91.3] |
| DBP ≥ 90 | 0.782* [0.746-0.816] | <0.0001 | 77.19 [71.6-82.1] | 79.33 [74.3-83.8] | 3.73 [3.0-4.7] | 0.29 [0.2-0.4] | 76.6 [71.0-81.6] | 79.9 [74.9-84.3] |
| SBP ≥ 140 and CRR ≥ 15 | 0.859* [0.828-0.887] | <0.0001 | 77.19 [71.6-82.1] | 94.67 [91.5-96.9] | 14.47 [8.9-23.4] | 0.24 [0.2-0.3] | 92.7 [88.4-95.8] | 82.6 [78.1-86.4] |
| DBP ≥ 90 and CRR ≥ 15 | 0.831* [0.797-0.861] | <0.0001 | 69.58 [63.6-75.1] | 96.67 [94.0-98.4] | 20.87 [11.3-38.6] | 0.31 [0.3-0.4] | 94.8 [90.7-97.5] | 78.4 [73.8-82.5] |
| Hypertension & Proteinuria (ACOG criteria) ‡ | 0.850* [0.818-0.879] | <0.0001 | 77.22 [71.6-82.2] | 92.93 [89.4-95.6] | 10.92 [7.2-16.6] | 0.25 [0.2-0.3] | 90.5 [85.8-94.0] | 82.4 [77.9-86.3] |
| Hypertension & Proteinuria (WHO criteria)§ | 0.772* [0.773-0.807] | <0.0001 | 55.51 [49.2-61.7] | 98.90 [96.8-99.8] | 50.33 [16.2-100] | 0.45 [0.4-0.5] | 97.9 [94.0-19.6] | 70.4 [65.6-75.0] |

Clinical dipstick results (Siemens 8SG Multistix) obtained with an electronic reader
Abbreviations: CRR: Congo Red Retention, SBP: systolic blood pressure, DBP: diastolic blood pressure
*P < 0.05 vs CRR ≥ 15%
‡ Diagnostic criteria for preeclampsia recommended by the American College of Obstetricians and Gynecologists (ACOG): Hypertension was defined as SBP ≥ 140 or DBP ≥ 90. Proteinuria was defined as ≥300 mg/24 h or a dipstick ≥+ 1 (for cases who did not have an indicated 24 h proteinuria measurement or who did not complete 24 h collection) (3). Diagnostic criteria for preeclampsia recommended by World Health Organization (WHO): Hypertension was defined as DBP ≥ 90. Proteinuria was defined as dipstick ≥+ 2 (23).

This was significantly better compared to the currently recognized clinical screening criteria for diagnosis of PE (CRR vs. blood pressure P<0.001; CRR vs. protein dipstick P<0.001). CRR had additive value to both systolic and diastolic blood pressures (P<0.001). CRR alone performed significantly better than the combination of blood pressure and proteinuria based the recommended cut-offs of both ACOG (P=0.004) (3) and WHO (P<0.001) (23). The association of CRR with MIDPE remained significant after controlling for GA and maternal demographic characteristics in multiple logistic regression (NRCRR odds ratio [95% CI]: 30.6 [18.9-49.6]; GA odds ratio: 3.3 [2.0-5.4]). Maternal age, race and parity were excluded from the model based on P>0.1.

Figure 13:
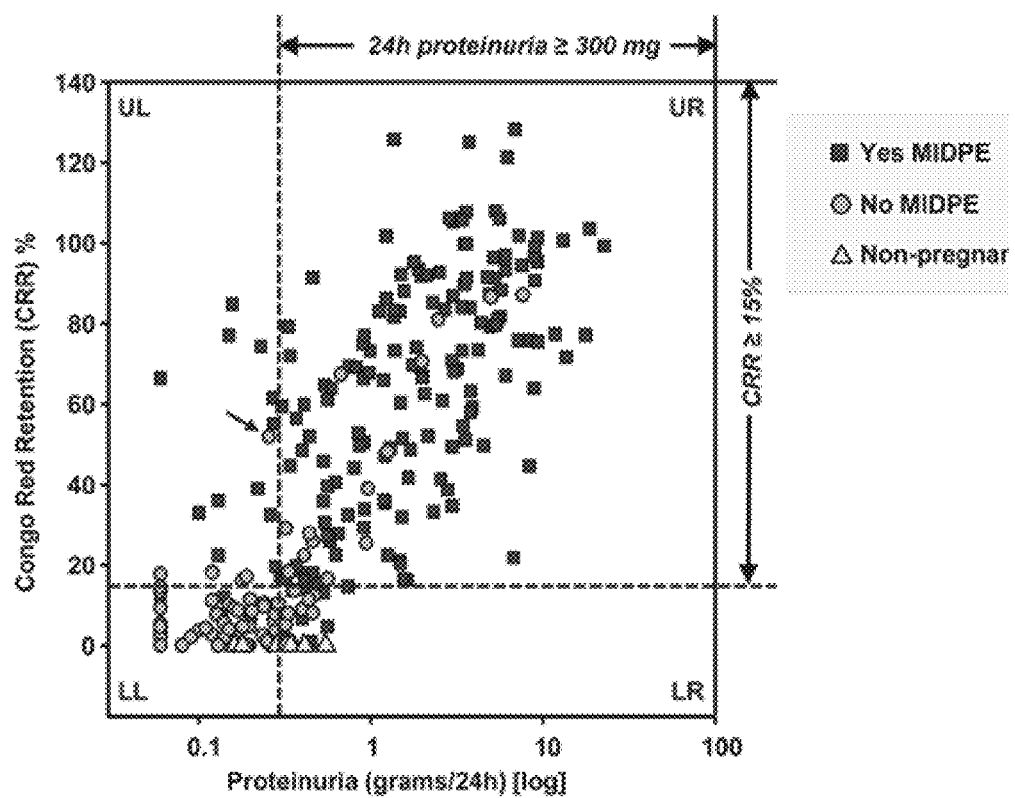
FIG. 13 shows examples of quantitative relationships of urine congophilia with 24 hour urine proteinuria.

Next, the group of women who completed 24-hour protein collections (considered the current gold standard for proteinuria of PE, n=250) was analyzed. There was a significant correlation between CRR and 24 h-proteinuria (r=0.788, P<0.001). Of the women with 24 h-proteinuria ≥300 mg/24 h that required MIDPE, 94% (148/158) had CRR≥15% and 82% (129/158) had CRR≥30% (FIG. 13). A number of PE cases deemed "atypical" based on absence of either proteinuria or hypertension displayed urine congophilia. Of the non-proteinuric "atypical" cases, 58% (23/40) were congophilic at the time of first evaluation, suggesting the potential clinical usefulness of the CRD test in such clinical circumstances. All 23 congophilic women with "atypical PE" had a medically indicated delivery. In 21 cases the delivery indication was sPE with atypical presentation. In the remaining 2 cases the indication for delivery was abnormal fetal heart rate tracing.

Figure 7F:
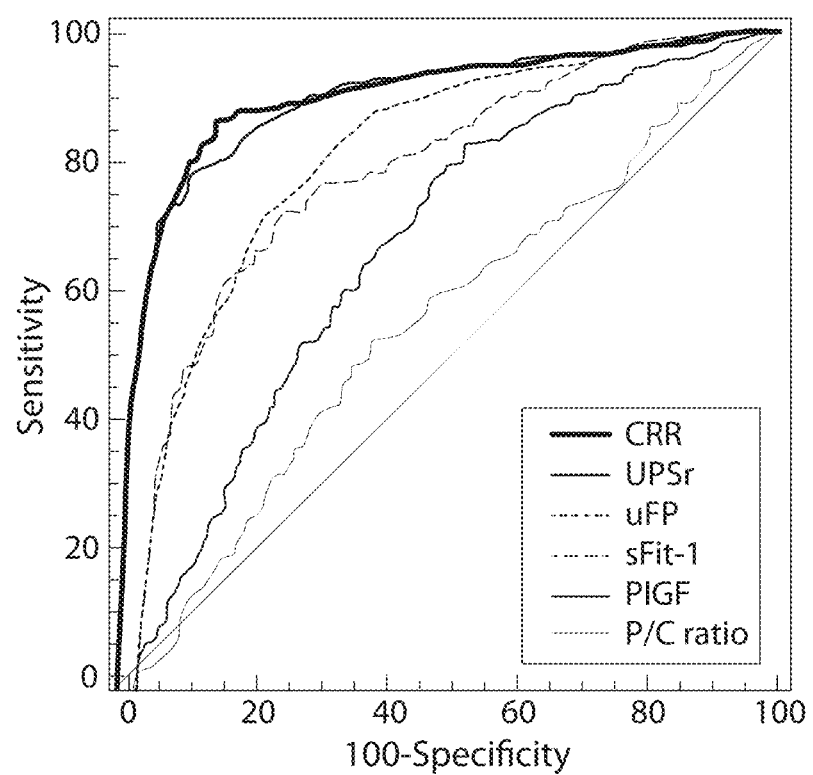

CRR performed significantly better than urine soluble fms-like tyrosine kinase-1 (sFlt-1)/placental growth factor (PlGF) ratio [uFP, z-statistic=4.5, P<0.001], creatinine-normalized urine sFlt-1 concentration (z-statistic=6.8, P<0.001), creatinine-normalized urine PlGF concentration (z-statistic=9.2, P<0.001) and protein-to-creatinine (P:C) ratio (z-statistic=13.9, P<0.001) (FIG. 7F). CRR had similar performance in predicting MIDPE with our previously described urine proteomics score (UPS, z-statistic=0.4, P=0.695). The UPS was the strongest predictor of urine congophilia among women who required MIDPE, independent of GA or total proteinuria or albuminuria (P<0.001). This finding concurred with the prior observation that several peptide fragment biomarkers of the UPS score have a high misfolding potential.

Figures 8A, 8B, 8C, 8D:
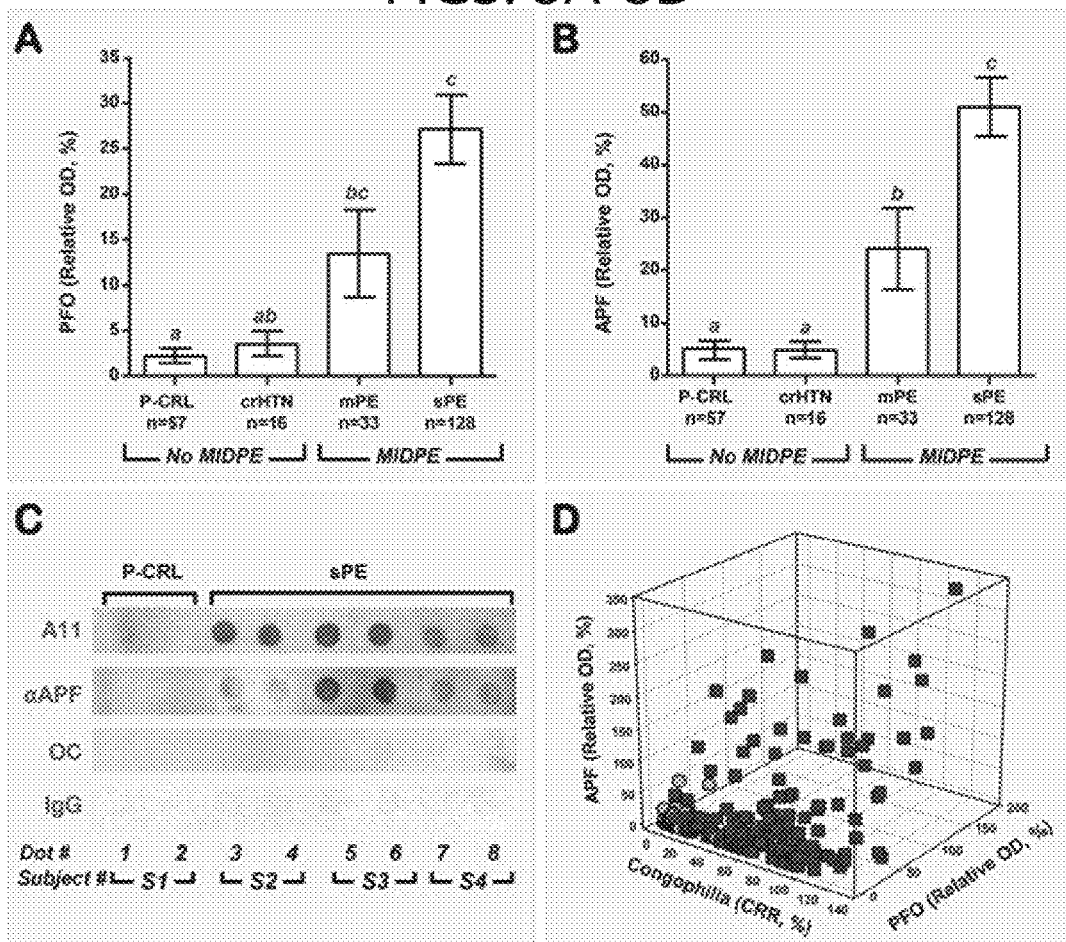
FIGS. 8A-8D show examples of urine oligomeric immunoreactivity and relationships with preeclampsia severity.

Urine Congophilia Associates with Immunoreactivity for Oligomeric Epitopes of Prototype Misfolded Proteins Three quaternary structure antibodies, previously validated, were used to identify mutually exclusive epitopes of known amyloidogenic proteins. The A11 polyclonal antibody detects generic, sequence independent conformational epitopes on cytotoxic prefibrillar oligomers (PFOs) that appear to be antiparallel β-sheet structures, including β-barrels and β-cylindrins. The aAPF polyclonal antibody recognizes generic, sequence independent epitopes on annular protofibril (APFs) conformations that appear to be β-barrels and are more mature and thus less cytotoxic than generic PFOs. The OC antibody detects parallel, in-register fibril conformations of mature fibrils and soluble fibrillar oligomers. Protein-normalized dot-blots were performed on a subset of 234 consecutive urine specimens from P-CRL (n=57), crHTN (n=16), mPE (n=33), and sPE (n=128) women. There was higher A11 immunoreactivity in sPE compared to P-CRLs and crHTN women (P<0.001, FIG. 8A). Compared to P-CRL and crHTN, both sPE and mPE women had significantly elevated urine immunoreactivity levels for αAPF at enrolment (FIG. 8B). As shown in FIG. 8C, there was significant heterogeneity in A11 and αAPF immunoreactivity with some specimens reacting equally to both antibodies (S3) while others predominantly with one (S2). These results can be explained in view of recent results suggesting a role for PFOs as precursors for APF formation. Significant reactivity was not found with the OC antibody. Collectively, these results indicated presence of both PFOs and APFs, but not fibrillar oligomers or mature fibrils in the urine of women with PE. However, not all sPE women with urine congophilia displayed detectable APF or PFO immunoreactivity. FIG. 8D displays a 3D plot of the A11 and αAPF immunoreactivity along with congophilia level for each urine specimen included in our analysis. While most non-MIDPE samples (n=73, green circles) clustered together close to the graph's origin, the MIDPE specimens (n=161, red squares) scattered substantially along the three axes, illustrating the large heterogeneity among urine PFO, APFs and congophilia. Within the MIDPE group, CRR correlated significantly with the PFO (r=0.268, P<0.001), but not APF immuno-reactivity (r=0.128, P=0.106). Remarkably, compared to women with absent urine PFO immunoreactivity, patients who tested positive had significantly higher systolic (P=0.002) and diastolic (P=0.020) blood pressures, and more severe clinical manifestations of the hypertensive syndrome (P<0.001). All analyses remained significant after correction for GA and total proteinuria (urine P/C ratio).

Figure 9A:
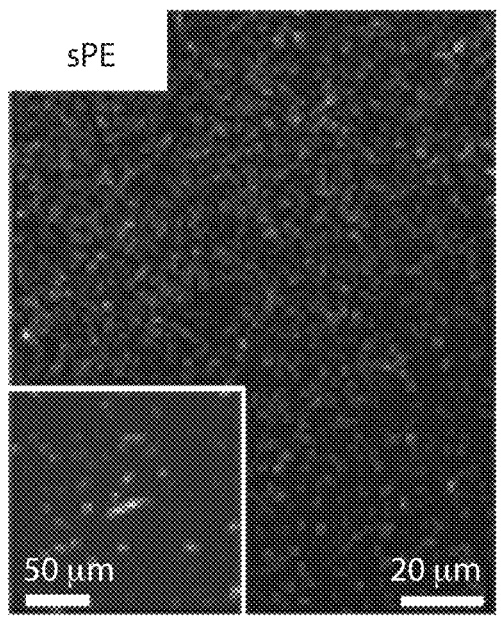
FIGS. 9A-9K show examples of microscopic and immunoreactive features of congophilic aggregates isolated from urine of women with severe preeclampsia (sPE).
Figure 9B:
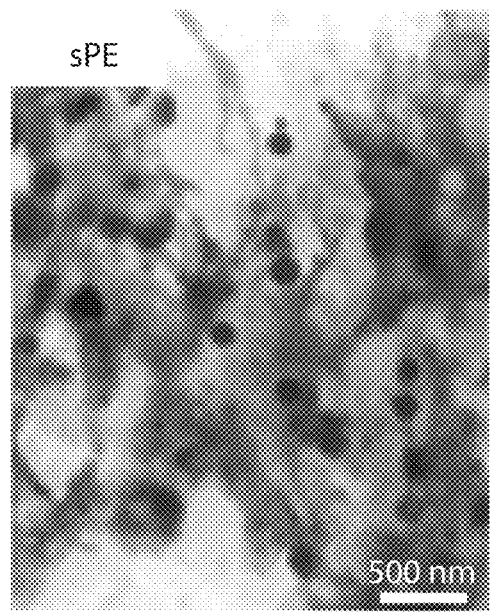
Figure 9C:
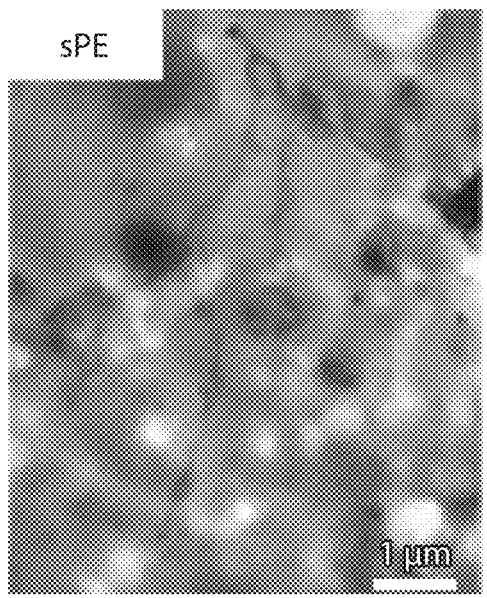
Figure 9D:
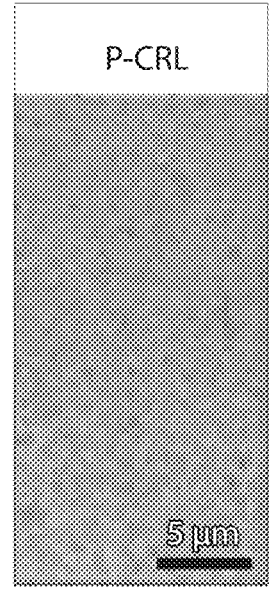
Figure 9E:
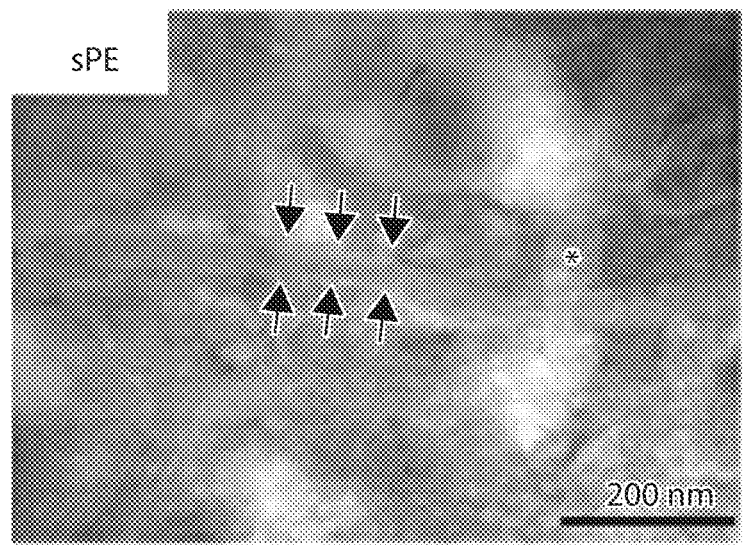
Figure 9F:
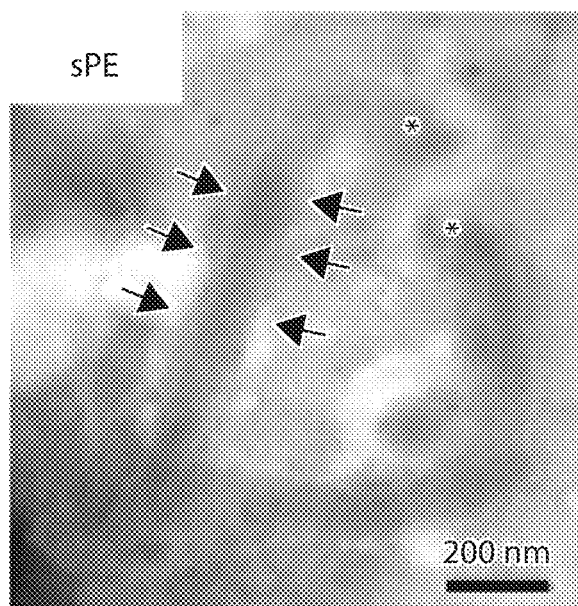

Congophilic Material Isolated from PE Urine Contains Round and Fibrillar Nano-Scale Structures with Amyloid-Like Microscopic Features A protocol for CR-assisted precipitation of urine samples was developed to further characterize the congophilia of PE. When the sPE precipitate was visualized by polarized microscopy (FIG. 9A), green birefringent round or elongated particles (see insert) were observed. At transmission electron microscopy (TEM, FIGS. 9B, 9C) the round structures varied in size from 30-300 nm while the fibrillar conformations were longer, arborescent, and tangled together in larger electrodense novel structures. These structures were absent in P-CRL specimens processed and imaged in parallel (FIG. 9D). Negative stain TEM (FIGS. 9E, 9F) showed the monofibrils as elongated filaments of ~50-60 nm diameters with smooth, rounded ends (asterisk). Except for the thicker diameter, this overall microscopic appearance of the congophilic precipitate from sPE urine was in close resemblance with that classically reported for fibrils extracted from amyloid-laden tissues stained with CR.

Figure 9G:
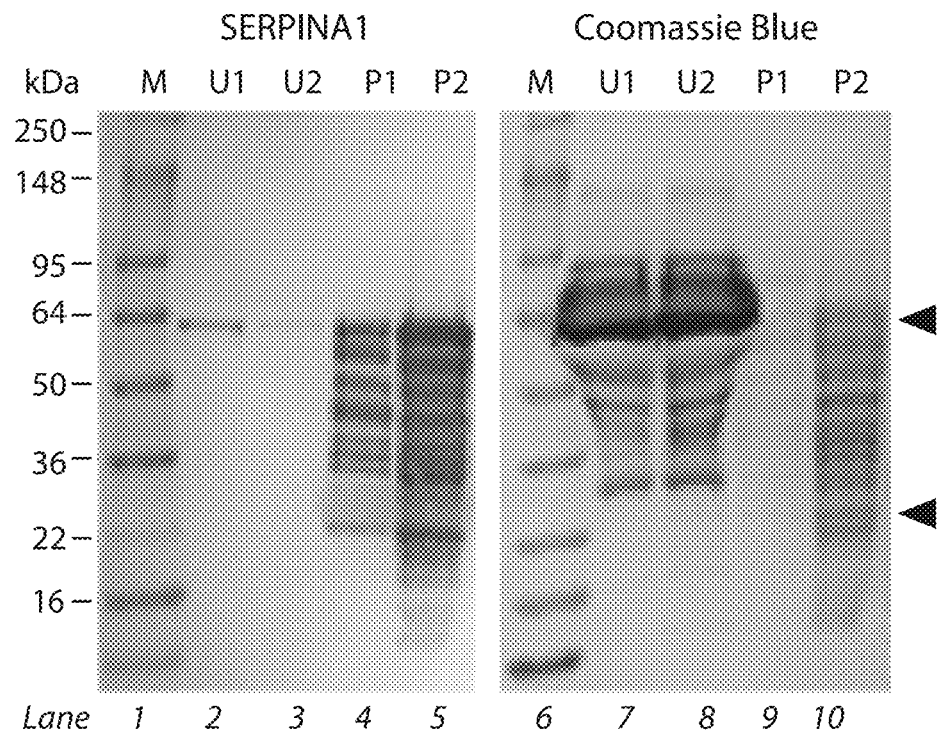
Figure 9H:
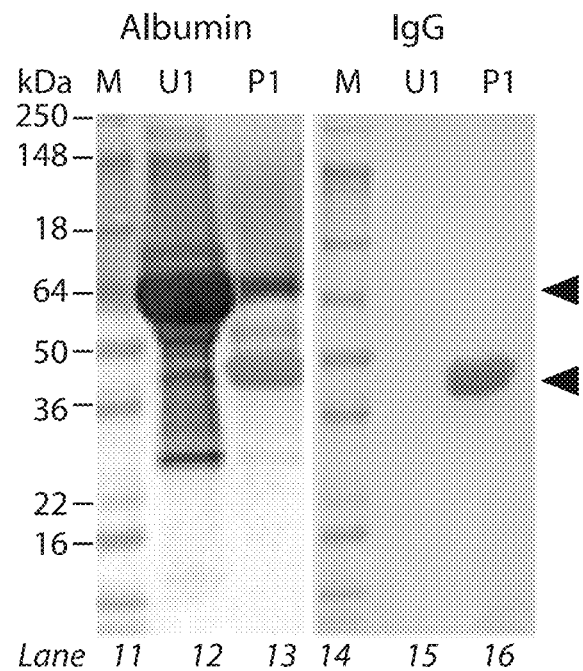
Figure 9I:
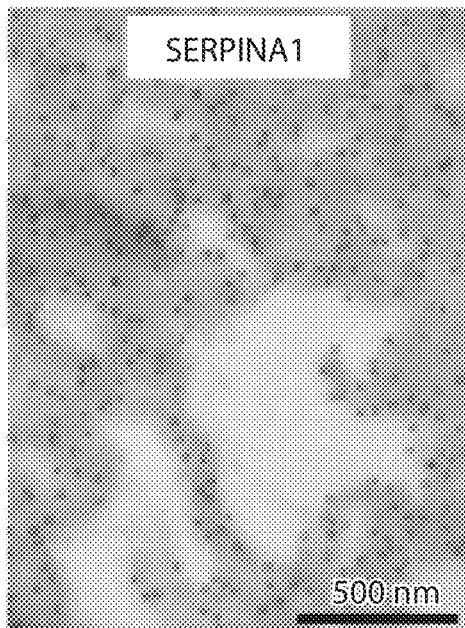
Figure 9J:
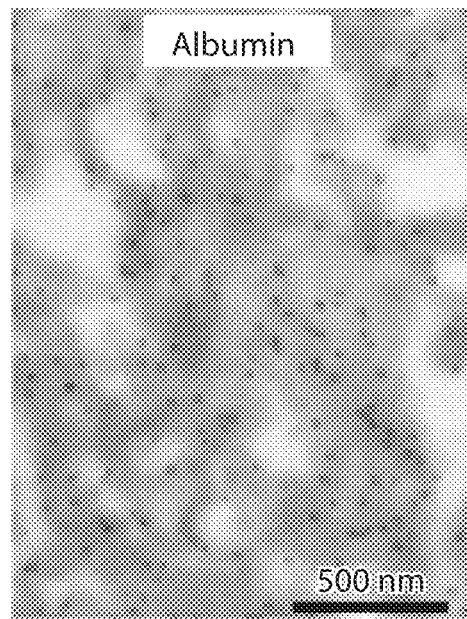
Figure 9K:
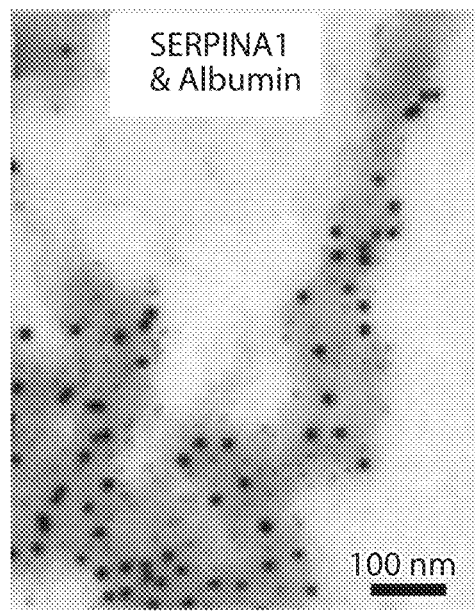

Mining the PE Misfoldome: Immunologic and Proteomic Analysis of Congophilic Material in PE Urine Reveals a Heterogeneous Protein Component The term "misfoldome" describes any collection of misfolded proteins. Discriminatory biomarkers of the UPS score represents non-random cleavage fragments of SERPINA1 and albumin. Based on SERPINA1's propensity to aggregate and protein misfolding in PE, the next step was to search for footprints of SERPINA1 and albumin in urine congophilic material. FIG. 9G (left panel) shows a representative SERPINA1 Western blot of two sPE urine samples (lanes U1-U2) and their corresponding CR precipitate (lanes P1-P2). As shown, the CR pellet was remarkably enriched in SERPINA1 immunoreactivity with the ladder pattern indicative of the predominance of SERPINA1 fragments over that of the intact precursor (~57 kDa, black arrow). A non-specific Coomassie stain of the same samples (FIG. 9G right panel) illustrated that the process of CR-assisted precipitation results in a change in banding pattern, implying that only some peptides in sPE urine have CR affinity and SERPINA1 fragments are part of this family. FIG. 9H (left panel) is a representative Western blot for albumin which illustrates a sPE urine sample before (U1) and after (P1) CR-assisted precipitation. As shown, the intact albumin precursor (~66 kDa, black arrow) and higher molecular weight aggregates appeared predominant relative to albumin fragments. The position of the CR dye migrating freely in the gel following reduction is marked by the red arrow. These experiments confirmed that CR precipitates from sPE urine have a protein component which, although heterogeneous, does not appear random. The protein component was further validated by TEM immuno-labeling with anti-albumin (FIG. 9I) and anti-SERPINA1 (FIG. 9J) antibodies. The pattern observed at double immuno-TEM indicated that SERPINA1 co-exists and albumin in the CR precipitates which supports the idea of heterologous co-aggregation.

Figure 14:
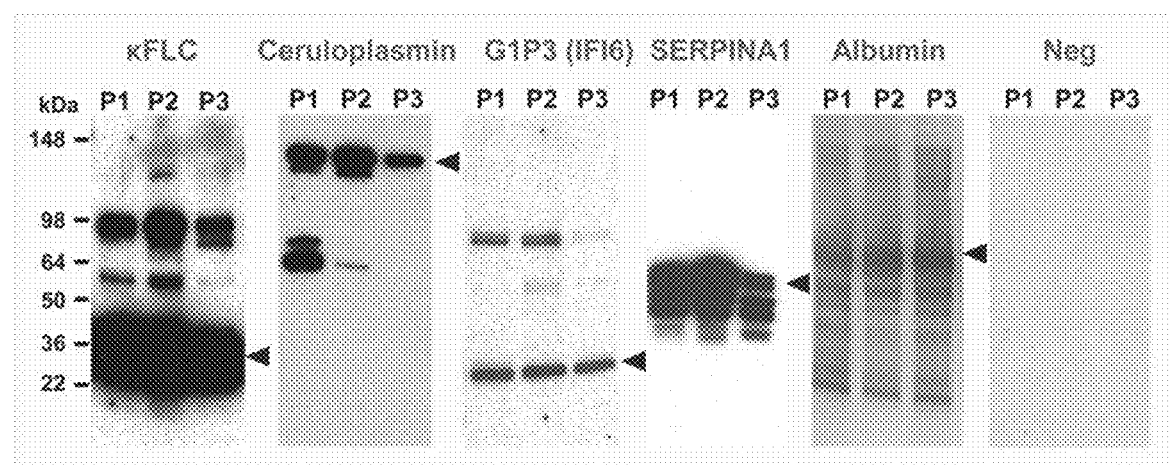
FIG. 14 shows an example of a Western blot validation of protein identities associated with the preeclampsia misfoldome.
Figure 15A:
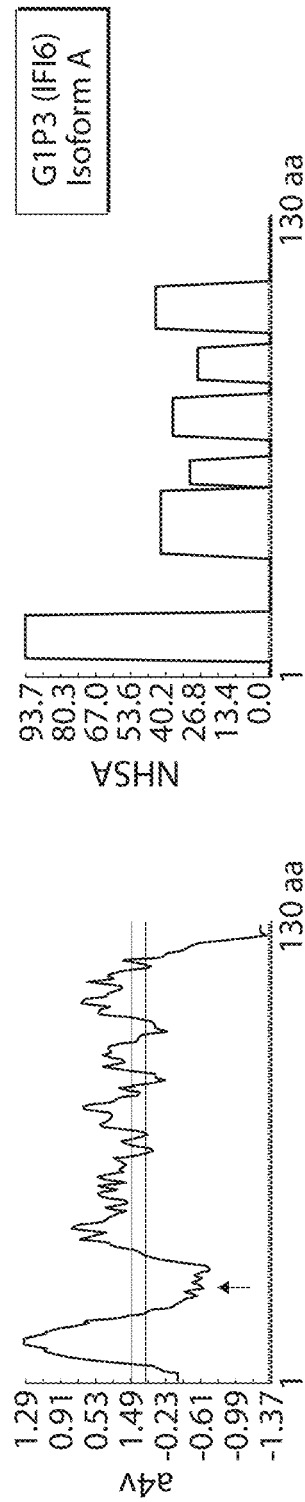
Figure 15B:
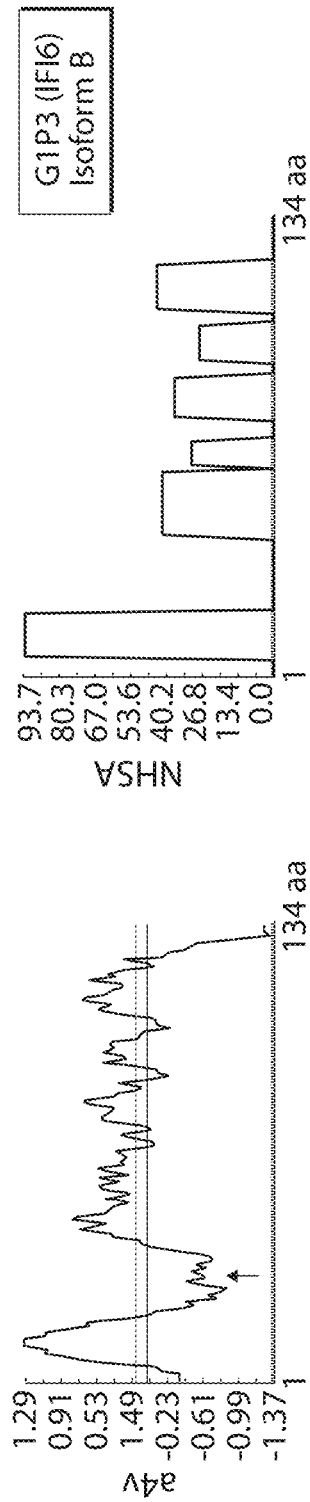
Figure 15C:
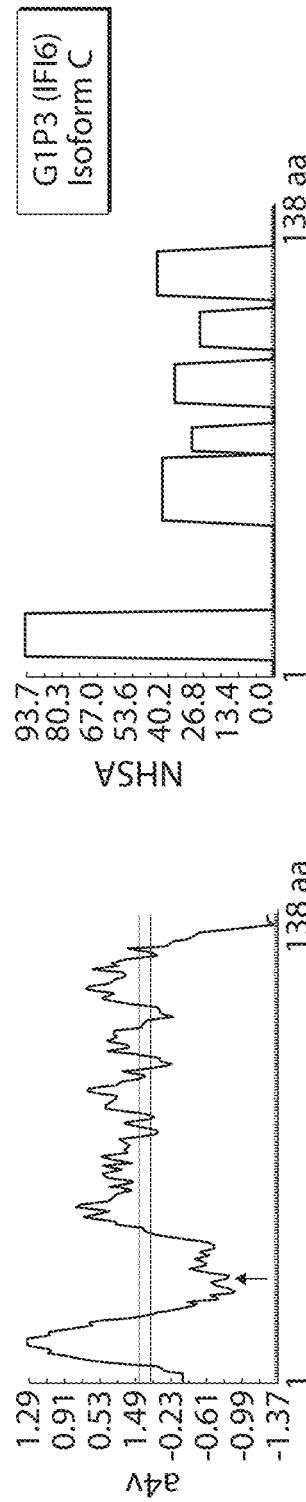
Figure 15D:
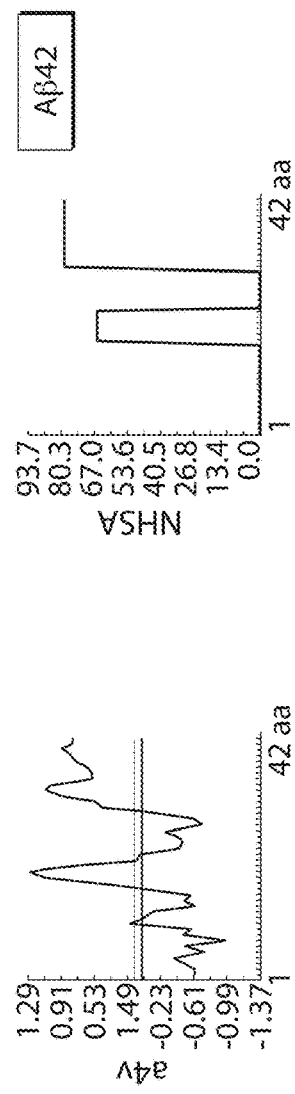
Figure 15E:
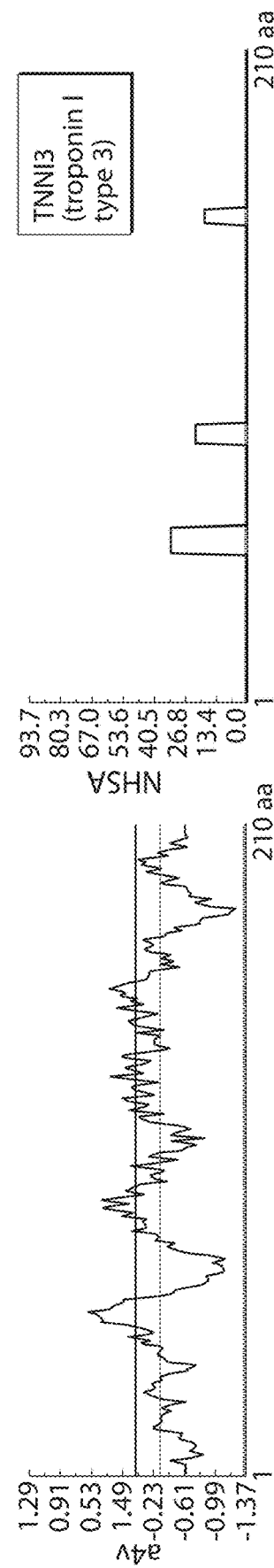

To determine what other proteins may be represented in CR precipitate, proteomics techniques were applied on specimens from well-characterized sPE cases. Aside from SERPINA1 and albumin, which were confirmed by tandem mass spectrometry, other represented identities were IgG κ-free light chain (KFLC), ceruloplasmin, and interferon-inducible protein 6-16 (IFI6 also known as G1P3). Interestingly, many of the peptides identified by mass spectrometry were found to contain oxidized methionine residues, a result which concurred with our prior finding of Met$^{365}$-oxidized C-terminus fragments of SERPINA1 as urine biomarkers of sPE. The above identities were validated by Western blotting of CR precipitates isolated from 60 different urine samples. Representative Western blots for KFLC (~25-30 kDa), ceruloplasmin (~150 kDa), G1P3 (~30 kDa), SERPINA1 (~57 kDa) and albumin (~66 kDa) in urine CR precipitates from 4 women with preterm sPE are shown in FIG. 14. Collectively, these results suggest that the congophilic material of sPE women contains proteoforms derived from fragments and/or aggregates of multiple proteins. Moreover, sPE patients share in their congophilic aggregates a non-random pattern of immunoreactive proteoforms from at least 5 different proteins. Because KFLC, ceruloplasmin and G1P3 had their most predominant immunoreactive band at the expected molecular size of the intact protein, this supports their intrinsic aggregation propensity even in non-fragmented state.

Unlike KFLC and ceruloplasmin, which have been previously reported to undergo pathologic aggregation with relevance for several human conformational disorders, G1P3 has not been previously investigated for participation in amyloid structures. We performed an in silico analysis of the amyloidogenic potential for the three G1P3 isoforms resulting from alternative splicing. Within the G1P3 sequence, we noted an unusually high number of aggregation-prone segments ("hot spots"). The AGGRESCAN algorithm predicted that G1P3 should have an aggregation propensity at least if not in excess of Aβ42 with the shortest isoform (G1P3a) being the most amyloidogenic (Na4vSS: G1P3a: 13.6 vs. Aβ42: 6.4, FIG. 15 and Table 4).

PE Urine Contains Aggregated APP Proteoforms

Fibrillar amyloid proteins are resistant to proteolysis by trypsin. This led us to consider the possibility that a proteomics approach, which relies on fingerprinting of tryptic cleavage peptides, might have missed important protein identities in the urine congophilic material. One candidate was APP. Cellular processing of APP is a well-recognized pathophysiologic phenomenon linked to Alzheimer's disease.

TABLE 4

Aggregation parameters for interferon-inducible protein 6-16 (G1P3) isoforms and for two prototype sequences with low and high propensity for aggregation

| AGGRESCAN | | G1P3 (IF16) | | | Prototype sequences | |
|---|---|---|---|---|---|---|
| | | [P19429] isoform | | | TNNI3 | Aβ42 |
| parameters | Definition | A | B | C | [P00912]† | [P05067] ‡ |
| a3vSA | aggregation propensity per aminoacid (a3v) sequence average | 0.13 | 0.10 | 0.08 | −0.31 | 0.06 |
| nHS | number of "hot spots" | 6 | 6 | 6 | 3 | 2 |
| NnHS | normalized number of "hot spots" | 4.62 | 4.48 | 4.35 | 1.43 | 4.76 |
| AAT | area of the aggregation profile above the "hot spots" threshold | 37.50 | 37.50 | 37.50 | 7.10 | 13.85 |
| THSA | total "hot spots" area | 36.80 | 36.80 | 36.80 | 5.24 | 13.73 |
| TA | total area of the aggregation profile | 20.80 | 17.59 | 14.34 | −62.99 | 3.43 |
| AATr | normalized area of the aggregation profile above the "hot spots threshold" | 0.29 | 0.28 | 0.27 | 0.03 | 0.33 |
| THSAr | normalized total "hot spots" area | 0.28 | 0.28 | 0.27 | 0.03 | 0.33 |
| Na4vSS | normalized a3v window average (a4v) sequence sum | 13.4 | 10.5 | 7.8 | −32.3 | 6.4 |

Figure 10A:
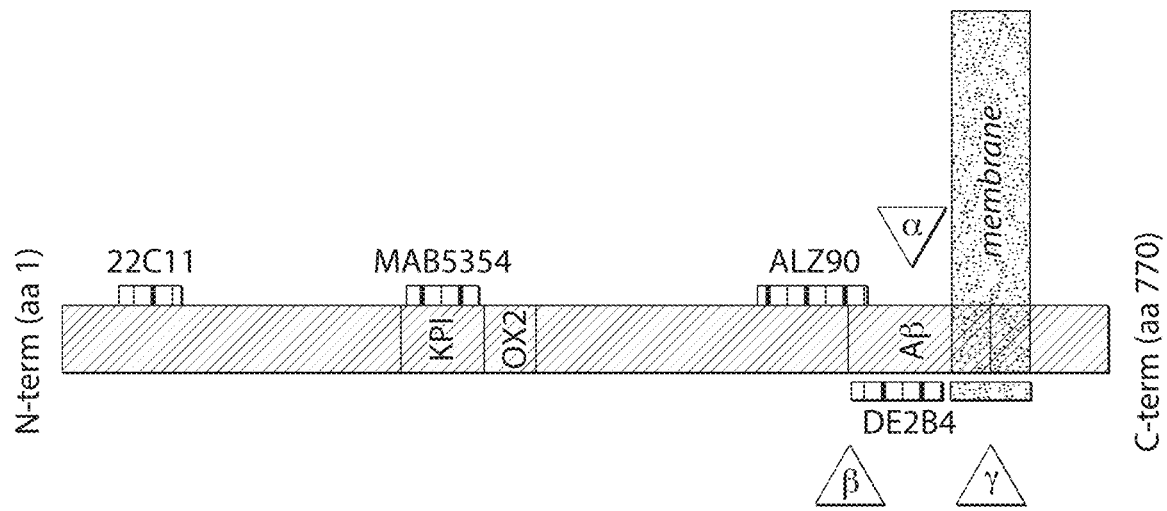
FIGS. 10A-10F show examples of amyloid precursor protein (APP) proteoforms in urine of women with severe preeclampsia.

† TNNI3 (troponin I type 3) is a natively unfolded inherently stable protein
‡ Aβ42 (amyloid beta 42) is an inherently unstable amyloidogenic peptide
Higher AGGRESCAN parameter values denote higher aggregation propensity while negative values imply very low aggregation propensity. Note the resemblance of G1P3's aggregation parameters with Aβ42's and the difference from TNNI3's. Moreover, the AGGRESCAN algorithm was able to determine that shorter G1P3 isoforms have higher theoretical aggregation potentials APP is a ubiquitously expressed protein with 3 main isoforms (APP770, APP751, APP695) generated through alternative splicing of the APP gene. In the normal metabolic pathway, APP is first cleaved by α-secretase rather than β-secretases to release a soluble N-terminal fragment (sAPPα). sAPPα is non-amylogenic and functions as a growth factor promoting cell survival, proliferation and migration. However, cleavage of APP by β-secretase and subsequently by λ-secretase (FIG. 10A) releases a short amyloid-β peptide (Aβ), which is a major constituent of congophilic senile plaques. Due to its high propensity for oligomerization and self-assembly, Aβ has direct pathological roles in inducing oxidative stress and neurodegeneration linked to Alzheimer's disease.

Figure 10B:
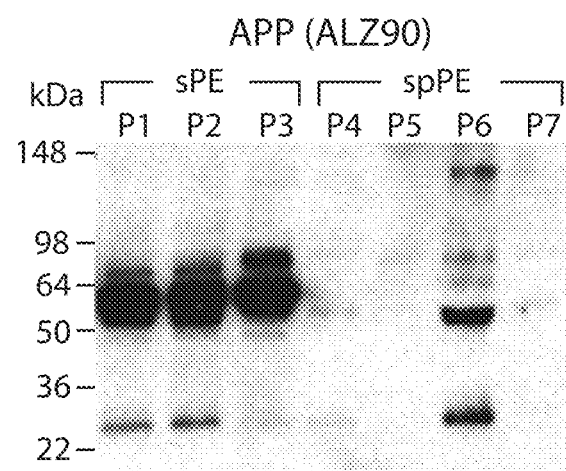

Based on the above knowledge, the presence of APP fragments was analyzed in the CR precipitate of urine samples retrieved from women with sPE. Using the ALZ90 monoclonal antibody that recognizes residues 511-608 in a domain specific to APP, the presence of APP fragments was demonstrated by Western blotting (FIG. 10B, lanes P1-P3) in these samples. The most conspicuous bands migrated between 60-90 kDa with a consistent banding pattern among sPE cases. This pattern was either absent or modified in spPE cases (P4-P7), an observation which supports the pathogenic difference between these two clinically overlapping syndromes associated with pregnancy. Because all samples shown in FIG. 10B had NR-CRR levels, it is likely that urine congophilia sums a collection of misfolded proteins that also includes APP fragments.

Figure 10C:
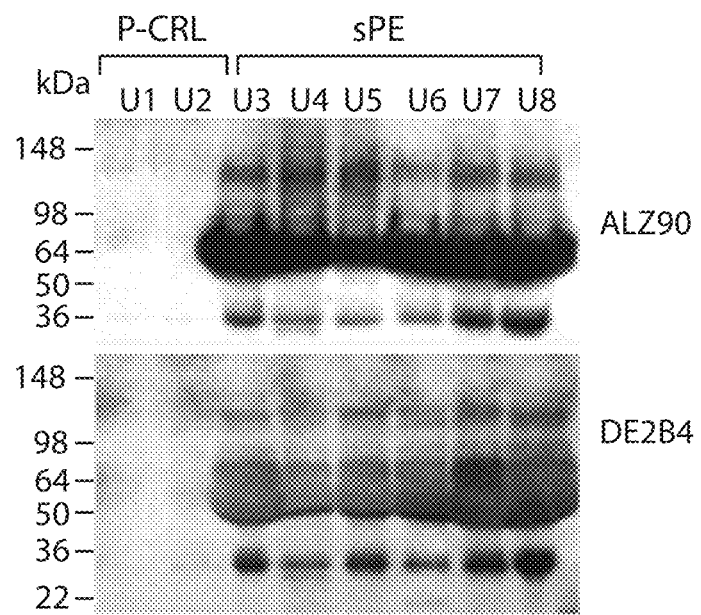
Figure 10D:
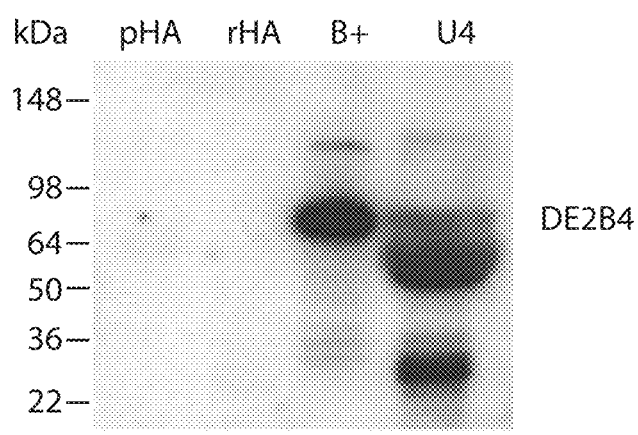
Figure 10E:
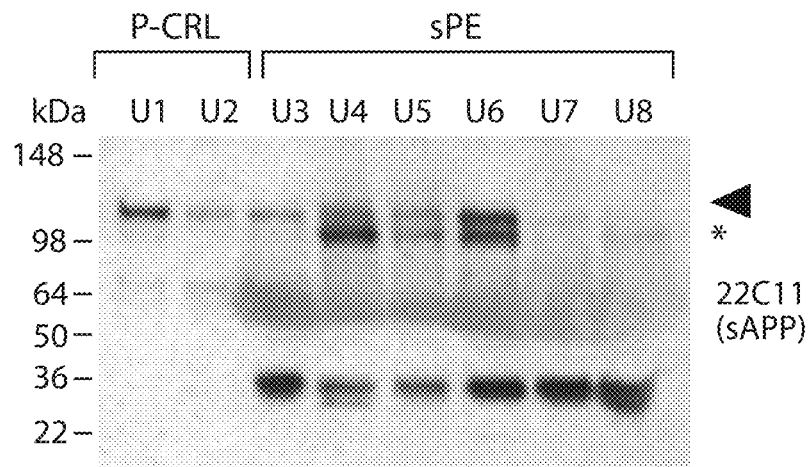
Figure 10F:
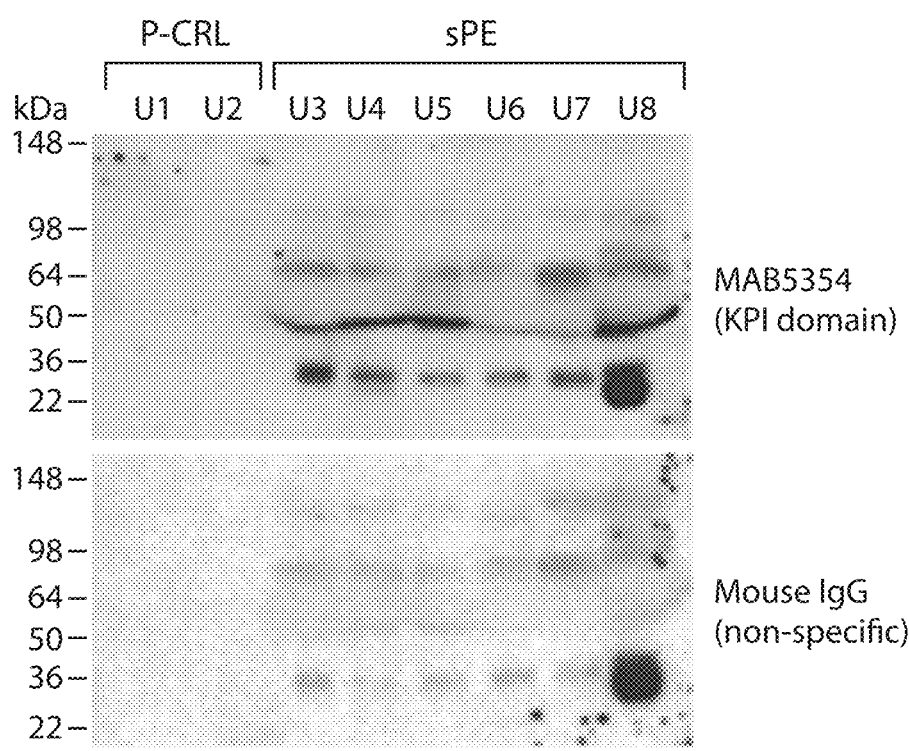
Figures 16A, 16B, 16C, 16D:
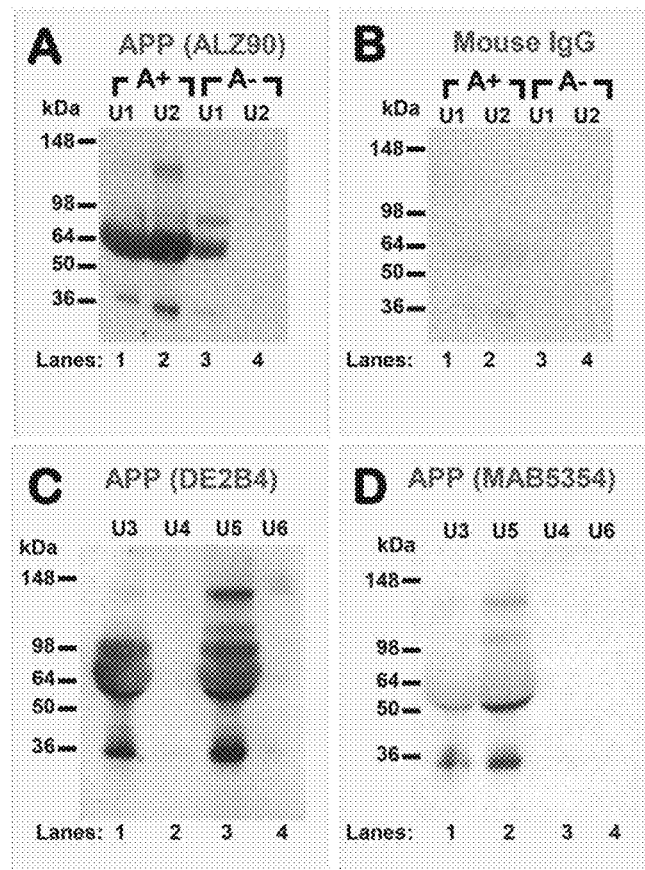
FIGS. 16A-16D show examples of patterns of amyloid precursor protein immunoreactivity in urine from a pregnant woman with preeclampsia: effect of albumin depletion (FIG. 16A, 16B) and patterns of APP immunoreactivity (FIG. 16C, 16D).
Figures 17A, 17B, 17C, 17D:
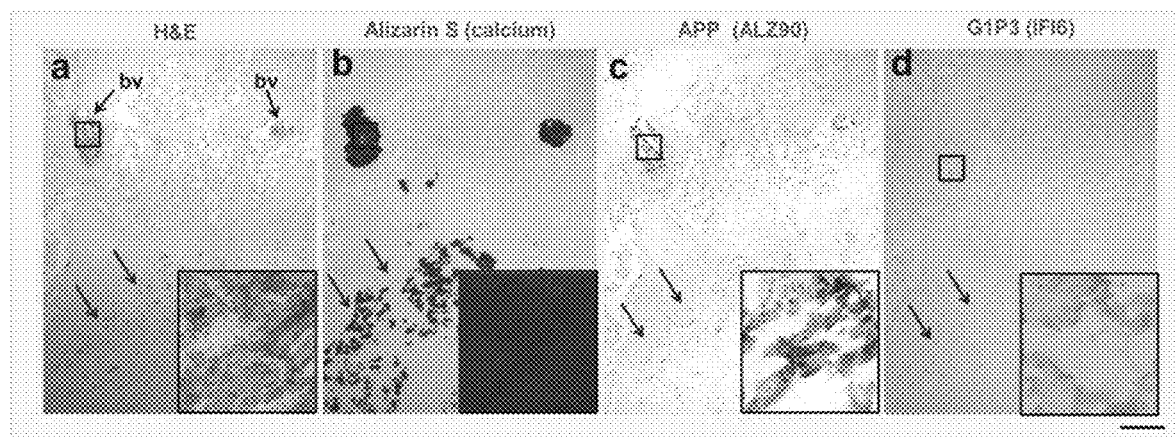
FIGS. 17A-17D show examples of immunolocalizations of ALZ90 and G1P3 epitopes in calcified Alzheimer's disease-like plaques in preeclamptic placenta.
Figures 18A, 18B, 18C, 18D, 18E, 18F, 18G, 18H, 18I, 18J:
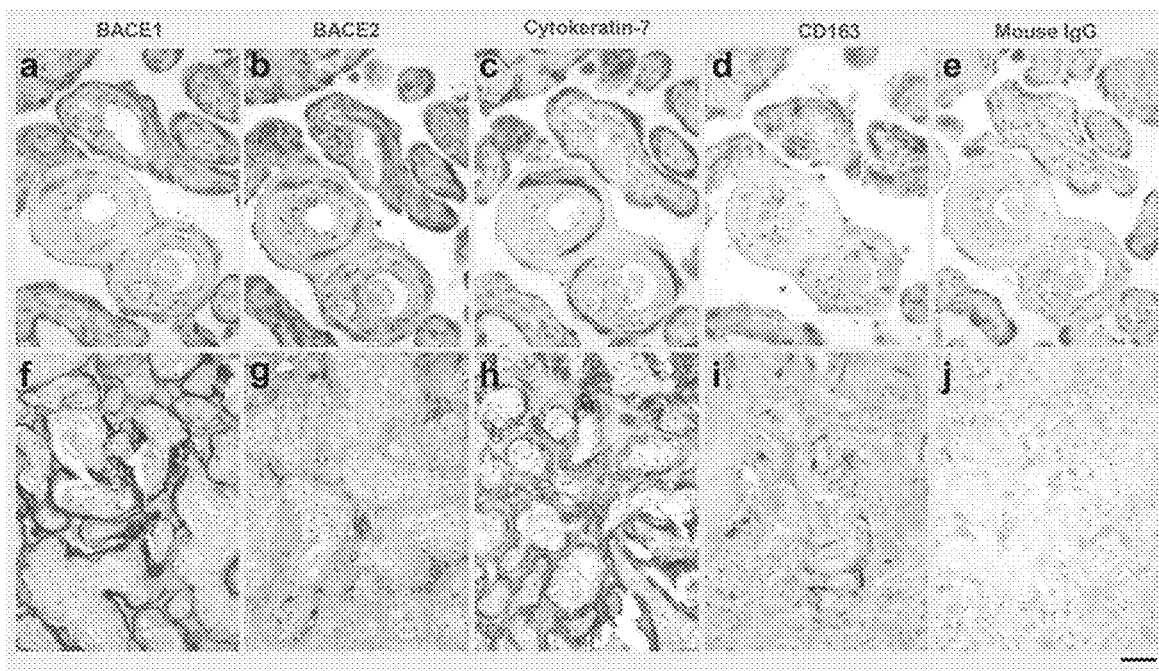
FIGS. 18A-18J show examples of patterns of immunoreactivity for β-secretases BACE1 and BACE2 in placenta from a woman with preeclampsia.
Figure 19A:
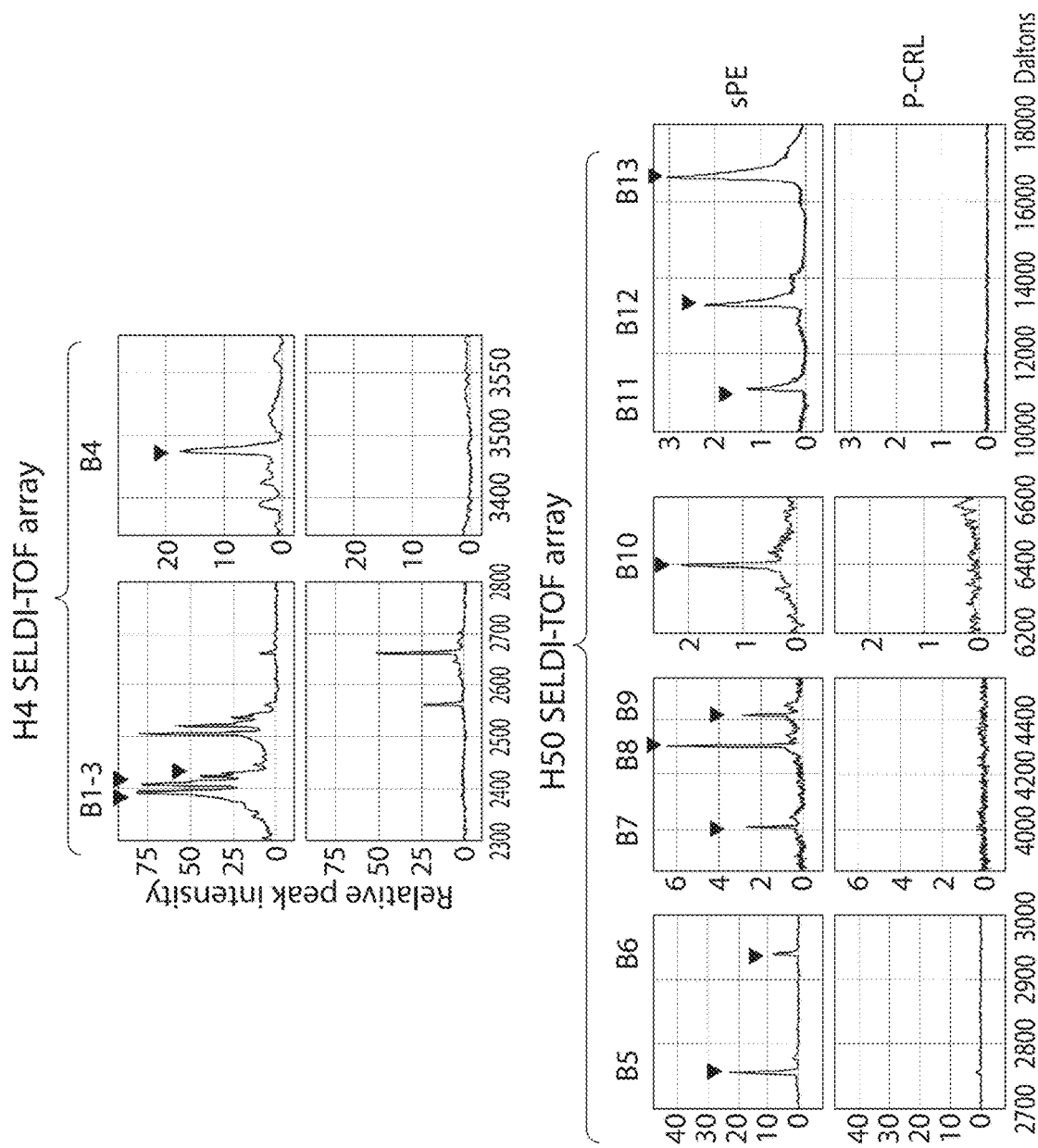
FIGS. 19A-19C show an example of a urine proteomics profile of preeclampsia (PE) with biomarker components mapping to a SERPINA1 sequence (SEQ ID NO: 4).
Figure 19B:
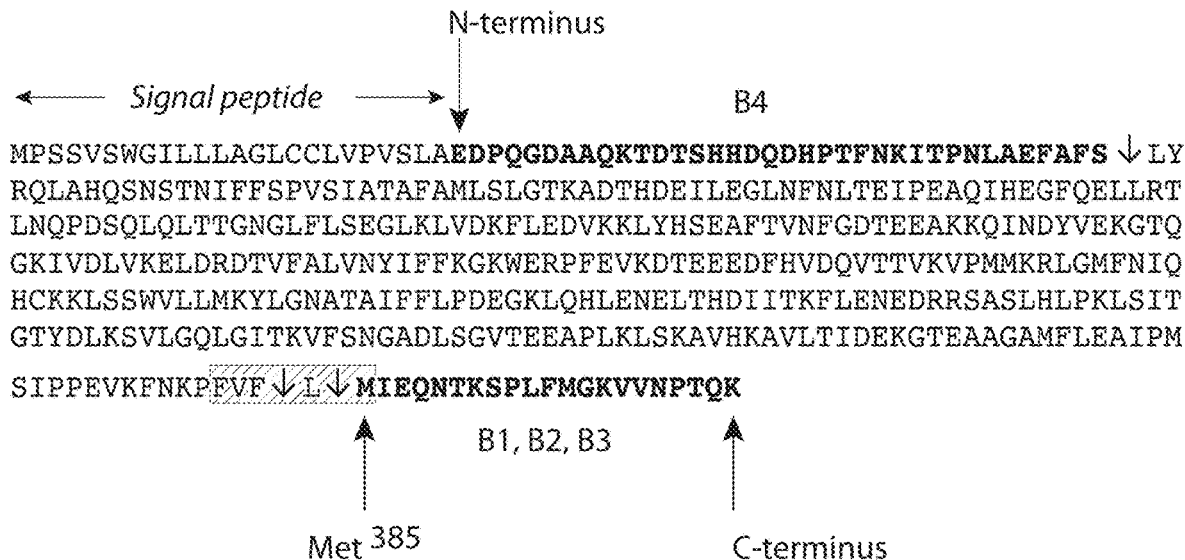
Figure 19C:
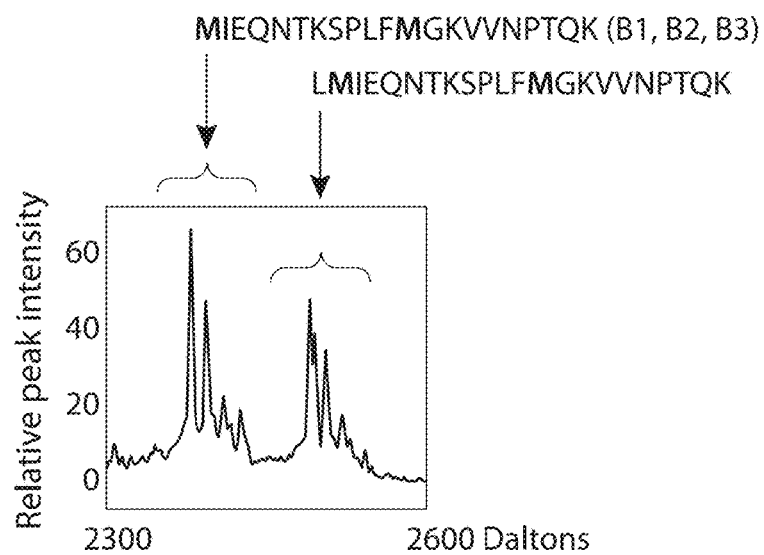

The presence of APP fragments in crude urine specimens of healthy P-CRL (n=8) and sPE (n=16) women was next investigated by Western blot using well-characterized monoclonal antibodies raised against an array of epitopes on the APP sequence: ALZ90, DE2B4 (reactive with an epitope within residues 1-17 of the Aβ region), 22C11 (reactive with an N-terminal epitope of APP, sAPP and the structurally related protein APLP-2) (47) and MAB5354 antibody (reactive with an epitope in the Kunitz protease inhibitor [KPI] domain) (43-45). FIG. 10C shows that, similar to the CR precipitate, crude sPE urine specimens (U3-U8) exhibited intense ALZ90 immunoreactivity. DE2B4 detected a similar immunoreactivity pattern with ALZ90 albeit of lower intensity. As the non-specific cross-reactivity of human albumin with the two anti-APP monoclonal antibodies was ruled out (FIG. 10D, shown for DE2B4) the only possible explanation for the banding pattern revealed by ALZ90 and DE2B4 in sPE urine was APP fragmentation and/or co-aggregation of APP fragments with other proteins. The latter possibility was substantiated by the decrease in intensity of the prominent 64 kDa band upon treatment of sPE urine with Cibacron blue, FIGS. 16A, 16B. The 22C11 antibody detected immunoreactive urine proteins in both P-CRL (U1-U2) and sPE (U3-U8) at the expected molecular weight for mature sAPP (~130 kDa) (FIG. 10E). Yet, sPE urine contained an additional band (~110 kDa) likely representing immature sAPP (lanes U4-U6). Notably, some sPE women with intense ALZ90 and DE2B4 immunoreactivity (lanes U3, U7, U8) had less prominent 22C11 sAPP bands. Interpreted together, the lack of significant staining for 22C11 with positive ALZ90 and DE2B4 immuno-reactivity suggests sPE women excrete significant amounts of APP fragments that are both N-truncated and α-secretase cleaved. Using an ELISA that detects total sAPP (sAPPα and sAPPβ), it was determined that sPE women (n=66) have higher fractional excretion of sAPP compared to P-CRLs (n=44) (sPE: 0.27% [0.05-0.90] vs. P-CRL: 0.09% [0.01-0.42], P=0.032).

sAPP isoforms containing the KPI domain (e.g., APP770 and APP 751) function as anti-proteases and are generically referred to as protease nexin-II (APP-KPI/PN2). Similar to SERPINA1, APP-KPI/PN2 potently inhibits serine proteases including trypsin and coagulation factors acting as suicide substrates. Fragments of APP-KPI/PN2 that include the KPI domain are known to be highly amyloidogenic (50, 51). FIG. 10F demonstrates that urine specimens of sPE women contain an APP fragment (~47 kDa) specifically detected by the MAB5354 (KPI domain) antibody. However, compared to DE2B4, MAB5354 immunoreactivity and hence the contribution of APP751 isoform appeared to be small (FIGS. 16C, 16D). In summary, mature sAPP proteoforms are normal urine constituents in healthy pregnancies. The relatively low serum sAPP, high fractional excretion of sAPP, and especially the high levels of fragmented APP proteoforms in sPE urine point to a possible derangement in the APP proteolytic processing pathway in sPE.

Figures 11A, 11B, 11C:
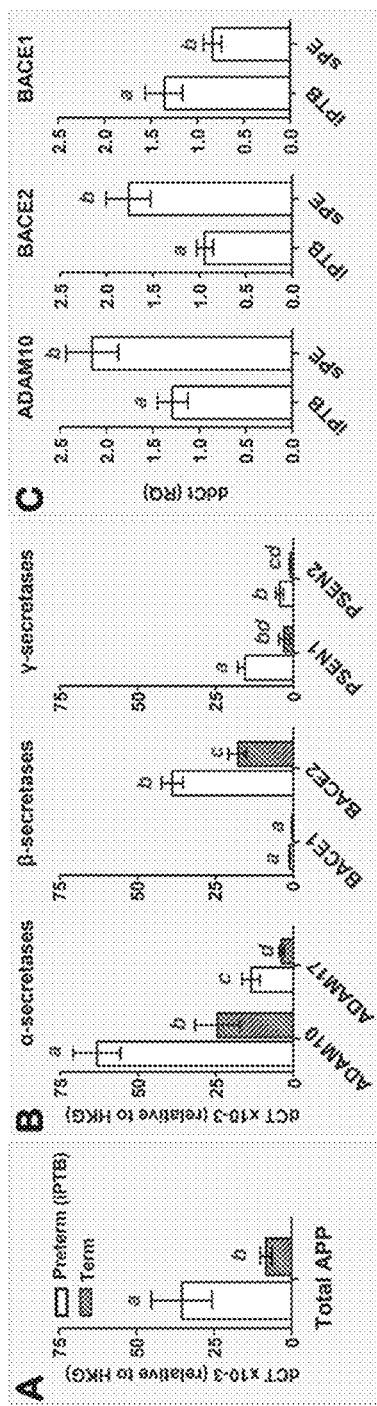
FIGS. 11A-11C show examples of mRNA expression of amyloid precursor protein and prototype amyloid precursor protein-processing enzymes in human placenta.
Figure 11D:
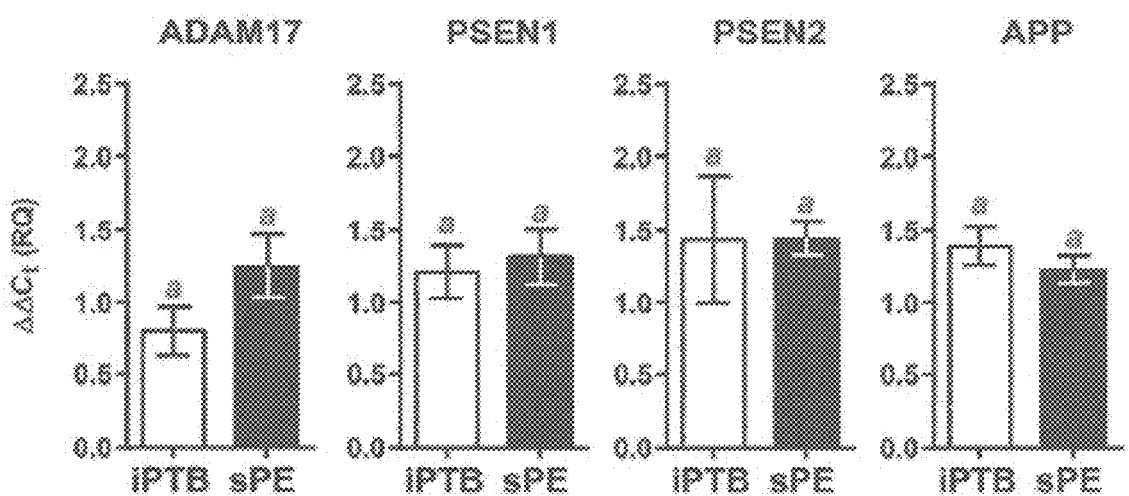
FIG. 11D shows relative quantitation of transcripts found statistically unchanged.

Human Placenta Expresses mRNA for APP and for Prototype α, β and γ-Secretases of which ADAM10 and BACE2 are Increased in PE The placenta is central to the pathophysiology of PE. As cellular processing of APP is a well-characterized sequence of enzymatic cleavages, we investigated the placental mRNA expression of total APP and of prototype APP processing enzymes: α-secretases (ADAM10, ADAM17), β-secretases (BACE1, BACE2) and γ-secretases (PSEN1, PSEN2). By quantitative real time RT-PCR we determined that the human placenta expresses mRNA for APP and for α, β and γ-secretases, with higher expression preterm versus term for APP, ADAM10, ADAM17, BACE2, PSEN1 and PSEN2 (FIGS. 11A, 11B). The relative abundance of the α-secretase ADAM10 was significantly higher than that of ADAM17 both preterm (P=0.001) and term (P=0.009). The amplification signal for the β-secretase BACE1 was only weakly detected in both preterm and term placenta. This was in contrast to BACE2 which was expressed at significantly higher levels especially in preterm placenta (P<0.001 vs. term). Compared to α- and β-secretases, γ-secretases had overall lower mRNA levels. The mRNA for PSEN1 was significantly higher compared to that of PSEN2 in preterm (P<0.001), but not in term placentas (P=0.209) where both γ-secretases were expressed at low levels. The villous trophoblast mRNA levels of ADAM10 (P<0.001) and BACE2 (P<0.001) were significantly higher in sPE compared to GA-matched placental tissues of women with idiopathic preterm birth (iPTB) (FIG. 11C). A comparison among the same groups showed decreased BACE1 mRNA levels in sPE (P=0.021, FIG. 11C). No significant changes in the mRNA expression were noted for ADAM17, PSEN1, PSEN2 or APP (P>0.05 for all).

Figures 12A, 12P:
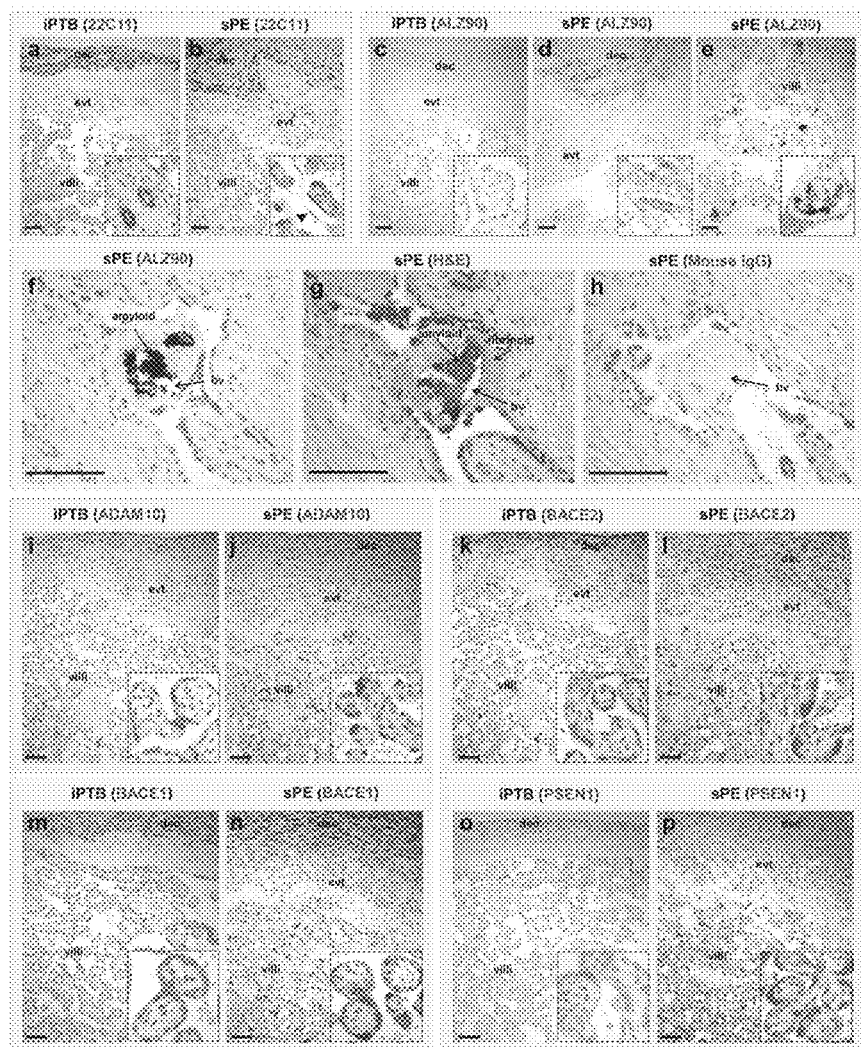
FIG. 12A-12P shows examples of immunolocalization of amyloid precursor protein and prototype amyloid precursor protein-processing enzymes in human placenta.

Severe Preeclampsia Associates with Deposition of Extracellular ALZ90 Positive Aggregates in the Placenta Resembling Amyloid Plaques Intense 22C11 (N-terminus) APP immunoreactivity was identified in the basal plate and chorionic villi of iPTB placentas (FIG. 12A). Decidual cells stained more intensely than extravillous trophoblasts, while in the placental villi, endothelial cells and cytothrophoblasts stained more conspicuously compared to the surrounding stroma (FIG. 12A, insert). There were notable differences in 22C11 staining patterns between sPE and iPTB placentas. In sPE, decidual cells stained positive at almost the same intensity compared to iPTB, but the distribution of the 22C11 decidual cells was more scattered and had a distorted morphology (FIG. 12B). Intense staining of acellular filamentous aggregates was observed in the maternal inter-villous spaces, with a significantly increased number on sPE sections FIG. 12B insert, arrowhead).

The pattern of ALZ90 antibody staining (specific for Aβ amyloid plaques) was different from that observed with 22C11. ALZ90 positive areas were scarce in preterm iPTB tissues and, when present, they localized more often to the decidua (FIG. 12C) rather than to placental villi where histological immunoreactivity was virtually absent (FIG. 12C, insert). Conversely, in sPE placentas, ALZ90 staining was more prominent both in the basal plate (FIG. 12D) and villous areas (FIG. 12E) giving an overall piecemeal appearance of the placenta. Notably, ALZ90 positivity localized to punctuated (FIG. 12E, insert) or flaky acellular material aggregated into plaques (FIG. 12F). ALZ90 positive plaques were more frequently observed in areas affected by fibrinoid-like degeneration. Still, not all fibrinoid-like material was ALZ90-positive. At H&E staining, the ALZ90-positive material had a characteristic purple proteinaceous appearance different from the surrounding eosinophilic fibrinoid (FIG. 12G). Incubation with mouse IgG confirmed staining specificity (FIG. 12H). The ALZ90-positive endovascular material was immunoreactive for G1P3, and frequently noted in areas traditionally described morphologically as placental calcifications, which we confirmed by Alizarin S staining (FIGS. 17A-17D).

Human Placenta Expresses Immunoreactivity for Prototype α, β and γ-Secretases of which ADAM10, BACE1, BACE2 and PSEN1 are Increased in PE Placentas in Cell-Specific Manner Compared to iPTB placentas, sPE placentas expressed more ADAM10 (P=0.017, FIGS. 12I, 12J) and BACE2 (P=0.007, FIGS. 12K, 12L). In sPE, villous ADAM10 immunoreactivity localized predominantly to cytotrophoblasts (FIG. 8J), while the β-secretase BACE2 was more ubiquitously expressed among the placental cell populations including villous cytotrophoblasts, syncytiotrophoblast and villous stromal cells (FIG. 8L). Human placenta was found to display positive immunostaining for BACE1. In iPTB placentas decidual cells and cytotrophoblasts showed most of the positive staining (FIG. 8M). A change in BACE1 expression pattern was observed in sPE villi with prominent BACE1 presence in the syncytiotrophoblast layer that appeared to surround the edge of the villi (FIG. 8N). Of note sPE placentas showed regional differences in BACE1 staining intensity (FIGS. 18A-18J). Areas in proximity of placental infarcts were observed to have the most marked syncytiotrophoblast staining. With respect to the γ-secretase PSEN1, iPTB placenta had virtually absent staining in villous cytotrophoblasts or syncytiotrophoblast (FIG. 12O, insert). Conversely, sPE syncytiotrophoblast showed notable PSEN1 staining (P=0.038, FIG. 12P, insert), which together with BACE1 represent two key enzymes involved in APP processing via the amyloidogenic pathway.

Study Design

Pregnant women were enrolled from March 2004 to December 2010 at Yale-New Haven Hospital (New Haven, Conn.). Non-pregnant proteinuric women were enrolled at Fletcher Allen Health Care Hospital (Burlington, Vt.). The research protocols were approved by both Yale University and University of Vermont Human Research Protection Program Committees. All women provided written informed consent. 824 urine samples from 662 women (FIG. 5) were investigated. For investigation of urine congophilia, a feasibility phase was conducted in 80 urine samples collected from 40 patients with sPE and MIDPE, and 40 healthy pregnant asymptomatic women who delivered at term in the absence of any complications. The clinical characteristics of the feasibility phase patients are presented in Supplementary Materials (Table 1). In a second phase of the study urine congophilia was subjected to further validation in a prospective cohort study consisting of 526 consecutive patients stratified based on their diagnosis at the time of enrollment in the following groups: (a) pregnant asymptomatic controls (P-CRL, n=18); (b) gestational hypertension (gHTN, n=28); (c) chronic hypertension (crHTN, n=63); (d) mild PE (mPE, n=53); (e) sPE (n=135); (f) superimposed PE (spPE, n=57); (g) pregnancy-associated medical conditions that did not necessitate laboratory work-up for PE (Other Type-1, n=125) (h) pregnancy-associated medical conditions or co-morbidities that associate frequently with PE and laboratory work-up was conducted to confirm or exclude PE (Other Type-2, n=37) and (i) non-pregnant proteinuric women (n=10). The clinical characteristics of the validation phase patients are presented in Supplementary Materials (Table 2).

The longitudinal cohort consisted of women who were asymptomatic at study entry and contributed with multiple samples throughout gestation (n=56). These patients were recruited consecutively based on investigator availability and appreciated as either high (n=28) or low (n=28) risk for PE.

Clinical and Surrogate Endpoints

PE is a syndrome characterized by heterogeneous clinical manifestations with different pathogenesis and various risk factors. The definition of PE and hypertensive disorders during pregnancy is often arbitrary. In the absence of data to support the validity of various definitions, diagnosing PE is not as easy as one might believe. There is significant difficulty in identification of patients who are at risk for adverse pregnancy outcomes, in particular in women with PE or various imitators of PE. As a result, in addition to clinical diagnostic categories, which can vary with both the disease course and physician, an intervention-based near-miss event was chosen, that is MIDPE, as a better reflection of true illness. This approach was successfully applied during our prior urine proteomics discovery study. Briefly, it was reasoned that an indication for MIDPE belongs to a clinical team, is the last management resort when all other therapeutic strategies have failed, its resulting outcome is final, cannot be revoked, and thus less subject to bias. Because clinical management of patients with PE (expectant vs. immediate delivery) may vary based on gestational age (GA) at the time of diagnosis, the results were analyzed in accordance to GA at delivery. <34, 34-366/7 and >37 weeks GA cut-offs were used. The number of patients delivered for MIDPE or other causes based on the above GA distribution, for both cross-sectional and longitudinal cohorts are presented in FIG. 5 and Tables 1 and 2.

Biological Samples

Urine samples were collected. Briefly, a random urine sample (5-10 mL) was collected by standard use of sterile containers using "straight cath" or "clean catch" sterile techniques. sPE women had a Foley catheter placed to allow for accurate monitoring of urinary output. Seventy percent of preterm PE women were enrolled before seizure prophylaxis (magnesium sulfate) and steroids. Women enrolled in the longitudinal cohort provided serial samples in a time sequential manner. Blood samples were collected by venipuncture in a subset of women from the cross-sectional cohort (n=141) at the time of urine collection. Blood was allowed to clot. Serum and urine samples were spun at 3,000 g at 4° C. for 20 minutes and either analyzed or stored in aliquots at −80° C. Placental tissues were collected immediately after delivery from women with sPE (n=8, GA: 31±1 weeks; growth percentile: 24±7%). GA matched spontaneous idiopathic preterm birth (n=8, diagnosis based on absent intra-amniotic infection by amniocentesis, absent histological chorioamnionitis, GA: 31±1 weeks; growth percentile: 31%±7%) and healthy women who delivered by scheduled Cesarean at term in the absence of labor (n=5, GA: 39±1 weeks, growth percentile: 36±10%) were used as controls. Tissues were either frozen in liquid nitrogen or fixed in formalin.

Evaluation of Urine Congophilia on Nitrocellulose Membrane Arrays and the Principle of the Congo Red Dot (CRD) Test Evaluation for urine congophilia was achieved based on a protocol by Halimi et al., who investigated this property in urine of patients affected by Creutzfeldt-Jakob (prion) disease. This protocol was optimized for PE urine in a membrane array format with the final result being the CRD test. Technical details are presented below. Briefly, 100 μl of urine supernatant were mixed with 2 μl of 5 mg/mL solution of CR. After 1-hour, 5 μl supernatant was spotted in duplicate onto a nitrocellulose membrane and left to air-dry. The membrane was sequentially washed in water followed by increasing concentrations of methanol. After wash, the CR-stained aggregates are retained in the membrane while the free CR (MW~700 g/mol) is removed. Because urine samples of PE women have wide variations in protein concentration standardization of the total protein/CR ratio was performed in this initial part of the study. The test output was expressed as % CR Retention [(CRR), measured the dye retained post-wash relative to the amount of dye added], and % CR Incorporation [(CRI), measured the dye added to each sample and served as internal control].

Evaluation of Urine Congophilia by Direct Spectrophotometry

Binding of CR to amyloids results in a change of the dye's absorbance spectrum in visible light (from orange-red to rose-magenta), and this bathochromic shift has been previously used to assess the level of β-amyloid oligomerization (aggregation) in-vitro (22, 100). All sPE and P-CRL urine samples used in the feasibility phase were processed as for the CRD test. The urine-CR mixture was diluted 10-fold and examined spectrophotometrically for CR-induced spectral shift (see below). A theoretical concentration of amyloid-like proteins in each urine sample was derived from absorbance values at 403, 504 and 541-nm using Klunk's formula. Normalization for intrinsic absorbance and light scattering was achieved by subtraction of values obtained in samples without CR. The spectral shift determined concentration of amyloid-like proteins was correlated with the subject's CRR test result.

Evaluation of ThT-Induced Fluorescence in Urine.

ThT fluorescence was measured after a protocol originally described for serum. Briefly, spun urine samples (30 μl) were mixed with 80 μM ThT in 100 mM phosphate buffered saline (PBS) pH 7.4. Fluorescence measurements were obtained in a spectrofluorometer (Clariostar, BMG Labtech, Cary N.C.) with excitation/emission wavelengths set at 444/485 nm, respectively. Normalization for intrinsic urine fluorescence was achieved by subtracting values in the absence of ThT.

Testing for Oligomeric State Immunoreactivity

Soluble amyloid oligomers are cytotoxic and potent inducers of cell death. Several immunologically distinct structural variants have been described: prefibrillar oligomers (PFOs), fibrillar oligomers (FOs), and annular protofibrils (APF). Presence of soluble amyloid oligomers in urine of four groups of women (P-CRL, n=57; crHTN, n=16; mPE, n=33, sPE, n=128) using a dot blot technique with the following primary antibodies: A11, OC, and anti-APF that recognize PFO, FO and APF, respectively (14-16). Technical details are provided in Supplementary Methods.

CR-Assisted Precipitation

Urine samples from 91 pregnant women in different clinical categories (P-CRL, n=13; crHTN, n=5; mPE, n=5; sPE, n=51; spPE: n=9; non-PE proteinuric conditions, n=8) were processed for CR-assisted precipitation as described in Supplementary Methods. CR-precipitates were visibly identified at the bottom of the microfuge in 90% of PE samples but not in any of the P-CRL, crHTN or non-PE proteinuric subjects (CR-precipitate negative).

Polarized Microscopy and Transmission Electron Microscopy (TEM)

CR precipitates from sPE urine (n=5) was re-suspended in water, dried on a microscope slide and visualized by polarized light microscopy for the characteristic green CR birefringence as described below. Alternatively, the suspension was placed onto 200 mesh formvar/carbon-coated nickel grids after positive or negative staining with 2% uranyl acetate. Specimens from tubes attempting to prepare CR precipitates P-CRL women (n=4) were also examined.

Identification, Validation and Aggregation Modeling of Proteins in Urine Congophilic Material CR precipitates were isolated from women with sPE (n=4, GA: 28±2 weeks), resuspended in reducing Laemelli buffer (BioRad) and boiled for 10 min. Samples were loaded onto 10% SDS-PAGE gels which were stained with Coommassie blue. Visible bands were excised and processed for tryptic digestion and tandem mass spectrometry (see below). Protein identity was established based on MOWSE scores >53 (matrixscience.com). SERPINA1, albumin, KFLC, ceruloplasmin and interferon-inducible protein 6-16 (G1P3) were found represented and selected for validation by Western blotting in CR precipitates isolated from 60 other cases. G1P3's aggregation propensity was determined using the AGGRESCAN algorithm ran on the web-based server at http://bioinf.uab.es/aggrescan/(details below).

Determination of APP and ADAM-10 Immunoreactivity in Urine, Urine Congophilic Material and/or Maternal Serum Western blotting was employed on representative congophilic material (n=38) and urine (n=16) of sPE cases. P-CRL urine (n=8) of GA matched cases was used for reference. Immunoreactivity for soluble APP (sAPP) and ADAM-10 immunoreactivity in serum and urine was investigated by ELISA (protocols described below).

Investigation of α, β and γ-Secretases by Quantitative Real-Time PCR and ImmunoHistochemistry Real-time PCR was performed on placental and amniochorion mRNA using the TaqMan chemistry (Applied Biosystems) and validated primer/probes for APP and the following APP-cleaving enzymes: α-secretases (ADAM10, ADAM17), β-secretases (BACE1, BACE2) and γ-secretases [Presenilin-1 (PSEN1), Presenilin-2 (PSEN2)]. Staining intensity in placental villi was assessed semiquantitatively on a scale from 0 (absent) to +5 (intense). Antibodies against Cytokeratin-7 and CD163 were used as cellular markers for trophoblasts and macrophages, respectively. Technical details are provided below.

Localization of Amyloid Plaques in Placenta by Immunohistochemistry

Aberrant deposition of amyloid is a feature of Alzheimer, a prototype protein misfolding disorder. Pathological evidence showed that fibrils of the peptide Aβ are a basic component of amyloid. Paraffin-embedded slides were processed for detection of Aβ epitopes known to be present in plaques in brains of patients with Alzheimer's. Two well characterized monoclonals (anti-ALZ90 and DE2B4) were used. Co-deposited calcium was identified by Alizarin S staining. Technical details are provided below.

Methodological Details on Other Biochemical, Immunological and Molecular Estimates All urine samples were analyzed for PE surrogate markers (used or proposed) such as protein-to-creatinine (P:C ratio), ratio of soluble fms-like tyrosine kinase-1 (sFlt-1) to placental growth factor (PlGF) (uFP) and urine proteomics scores (UPSb and UPSr). Technical details are provided below.

Statistical Analysis

Data was reported as either mean with standard error mean (SEM) (for normally distributed data) or as median with inter-quartile range (for non-normally distributed data). Data sets were compared with Student's t test, Mann- Whitney test, 1-way, 2-way or Kruskal Wallis ANOVA as appropriate. Correlation analysis was performed using Pearson's or Spearman's rank order correlation. Proportions were compared with Fisher's exact tests or Chi-square tests. Together, the urine samples of pregnant women enrolled in the feasibility and cross-sectional cohorts along with the first sample of the longitudinal cohort were representative for a consecutive cohort of women unbiased with respect to enrollment thus suitable for receiver operating curve characteristic (ROC). Test accuracy (cases correctly classified/total number of cases), sensitivity, specificity, positive and negative predictive values and likelihood ratios (LR) were measured on receiver operator characteristic ROC plots using MedCalc (Broekstraat, Belgium) statistical software. Confidence intervals (CI) were calculated using the bootstrapping method. Comparison of ROC curves was performed using the De Long method which uses a non-parametric method to determine statistical significance of the difference between the areas under dependent ROC curves (derived from the same cases).

Clinical Definitions

Gestational age (GA) was established using well established ultrasonographic criteria correlated with the day of the last menstrual period, in all instances.

Severe preeclampsia (sPE) was defined as systolic blood pressure of >160 mm Hg or diastolic >110 mm Hg on at least 2 occasions 6 hours apart, >5 grams protein excretion/24 h urine collection, and/or persistent+3 proteinuria on dipstick testing. Intra-uterine fetal growth restriction (IUGR)<10th percentile, persistent neurological symptoms (headache, visual disturbances), epigastric pain, oliguria (less than 500 mL/24 h), serum creatinine >1.0 mg/dL or any elements of HELLP syndrome: hemolysis, elevated liver enzymes (>2 times the normal), low platelet count (<100,000 cells/μL) were used as part of the definition for sPE per the American College of Obstetricians and Gynecologists (ACOG).

Mild PE (mPE) was defined as a diastolic blood pressure of at least 140/90 mmHg and urinary protein excretion of at least 300 mg/24 hours urine collection (or at least 1+ or greater on dipstick testing), each on two occasions 4-6 hours apart in the absence of signs or symptoms consistent with a diagnosis of either sPE or spPE per ACOG.

The World Health Organization (WHO) definition of PE diastolic ≥90 mm Hg and dipstick proteinuria 2+ or greater) was used for specified select statistical analyses.

Gestational hypertension was defined as elevated blood pressures consistent with PE on two occasions 4 hours to 1 week apart presenting de novo after 20 weeks without proteinuria or markers of sPE.

"Atypical PE" was diagnosed in the setting of:
  Gestational hypertension absent proteinuria, plus one or more of the following items: symptoms of preeclampsia (epigastric pain, severe headache, oliguria, pulmonary edema), hemolysis, thrombocytopenia (<100,000/mm$^3$), elevated liver enzymes (2 times the upper limit of the normal value for aspartate aminotransferase or alanine aminotransferase).
  Gestational proteinuria absent gestational hypertension, plus one or more of the following items: symptoms of preeclampsia, hemolysis, thrombocytopenia, elevated liver enzymes.

Superimposed preeclampsia (spPE) was defined as "new-onset proteinuria" in a woman with chronic hypertension before 20 weeks of gestation, a sudden increase in proteinuria if already present in early gestation, a sudden increase in hypertension, or the development of HELLP syndrome Chronic hypertension (crHTN) was defined as a sustained elevation in blood pressure prior to pregnancy or before 20 weeks gestational age.

Chronic nephropathy was diagnosed following consultation with a nephrologist if patients had a known pre-pregnancy kidney disease or persistent proteinuria (>0.5 grams/24-hours on at least two occasions) detected before 20 weeks GA.

Proteinuria in non-pregnant women was judged based on a cut-off of 150 mg/24-hours urine collection.

Other Type-1 (conditions not frequently associated with PE, which did not require PE work-up). We further tested urine congophilia in a group of pregnant patients who based on the clinical presentation did not necessitate PE work-up (n=125). Their clinical diagnoses at enrollment were: preterm premature rupture of membranes (PPROM, n=25), short cervix and/or preterm labor with intact membranes (n=76), placenta previa (n=6), intra-uterine fetal demise (IUFD) of unknown etiology in normotensive, non-proteinuric women (n=5), abruption in normotensive, non-proteinuric women (n=2), trombophilia (n=3) and pyelonephritis (n=8).

Other Type-2 (conditions frequently associated with high risk for PE, which required laboratory work-up to confirm or exclude PE). For clinical relevance and to test for the robustness of urine congophilia to discriminate among patients with and without PE, a clinically heterogeneous group of patients that required laboratory work-up for differential diagnosis with PE (n=37) was included in the analysis. This group consisted of cases that presented with IUGR (n=20), preexisting nephropathy (n=9), liver and/or kidney failure of unknown etiology (n=4), anti-phospholipid syndrome (n=4).

Protocol for the Congo Red Dot (CRD) Test and Calculation of CRR in Research Setting Sample preparation: Urine was spun at 15,000 g for 15 min. at 4° C. Total protein/concentration was measured using the Pierce BCA kit (Thermo Scientific, Rockford, Ill.) with albumin as standard. All urine samples were normalized with distilled water to measure 6.6-mg/mL total protein/concentration in the BCA assay. This value was chosen based on preliminary experiments investigating the linearity of the BCA assay as a function of CR and protein/concentration. For practical relevance, samples that measured >6.6-mg/mL in the BCA assay were diluted with water while samples measuring <6.6-mg/mL were concentrated to dryness in a SpeedVac (Thermo Scientific) and resuspended with water to the above concentration.

Preparation of the CRD nitrocellulose membrane array: 100 μl of normalized urine was mixed with 2 μl of stock aqueous solution of Congo Red (5 mg/mL, Sigma Cat #C6277, St Louis Mo.). A blank sample (BLK) was prepared by adding 2 μl of CR stock solution to 100-μl phosphate buffered saline (PBS). After 1-hour of vortex-mixing at room temperature, 5 μl of mixture was spotted in duplicate onto an unsupported nitrocellulose membrane (0.22 μm, BioRad, LaJolla Calif.) and left to air-dry (~15 min). The membrane was then rinsed with water for 3-min. and then photographed using a digital camera (CoolPix 4500, Nikon, Tokyo, Japan) to acquire the first picture (PIX1: before wash). Next, the membrane was washed with increasing concentrations of methanol [50% methanol: 3-min., 70% methanol: 1-min., 90% methanol until the red in the BLK samples disappears completely (~10-min). During this time, the red color of non-PE samples disappeared as free CR dye washed away. If urine contained misfolded proteins, the CR was retained by the immobilized misfolded proteins and the spots remained visibly red. A second picture was taken thereafter (PIX2: after wash).

Image processing: PIX1 and PIX2 were processed in Adobe Photoshop (Adobe, San Jose, Calif.). Specifically, each image was manually converted to grayscale, cropped, split in lanes and adjusted so that the same spots in PIX1 line up horizontally with those in PIX2. Optical density (OD) of each spot was determined using ImageJ software (http://imagej.nih.gov/ij/). The baseline was manually subtracted and area under the profile curve extracted. OD results were exported to Excel and the ratio PIX2/PIX1×100 calculated for each spot and averaged between duplicate spots per patient. This test result (CR Retention: CRR) was used throughout the current study as quantitative measure of urine congophilia and analyzed against clinical variables relevant to diagnosis and prognosis of PE. A second variable, CR Incorporation (CRI) was calculated only from PIX1 as the ratio of average sample OD/average BLK OD×100 and served as internal control.

Evaluation of Urine Congophilia by Direct Spectrophotometry

Spectrophotometrical analysis for CR-induced spectral shift in solution was performed as previously described for Aβ binding. Urine samples were normalized and mixed with CR as described for CRD test. 200 μl of 10 fold diluted CR-urine mixtures were applied in duplicate on 96-well plates along with same dilution of urine without CR. Blank samples were PBS with and without CR. Plates were read in a Spectramax plate reader (Molecular Devices, Sunnyvale, Calif.) equipped with SOFTmax Pro 4.0 software. Measurements were first taken in the wavelength-scanning mode (300-700 nm) followed by endpoint readings at 403 nm (isobestic point), 504 nm (point of maximal absorbance of free CR) and 541 nm (point of maximal difference between free and amyloid-bound CR). Correction for inherent light scattering was achieved by subtraction of OD readings from the same urine sample without CR. A theoretical concentration of amyloid-like proteins in each urine sample was derived from absorbance values using Klunk's formula and the result correlated with the subject's CRD test result.

Other Biochemical, Immunological and Molecular Estimates

Urine protein/concentration was measured with the bicinchoninic acid/cupric sulphate reagent (BCA kit, Pierce, Rockford, Ill.) against albumin standards. A 12-fold dilution factor was used for most urine samples. Repeat measurements on undiluted or 50-fold diluted samples were done on samples that measured below or above the standard curve, respectively.

Urine creatinine was measured colorimetrically (Stanbio Laboratory, Boerne, Tex.) against standard curves derived from known concentrations.

Urine unbound soluble fms-like tyrosine kinase (sFlt-1) and placental growth factor (PlGF) were measured by ELISA according to manufacturer's instructions (R&D Systems, Minneapolis, Minn.), as previously described (24). Urine samples were assayed in duplicate in a 96-well plate precoated with a capture antibody directed against free sFlt-1 and PlGF. Incubation and washing protocols were performed followed by reading at 450 nm. Minimal detectable concentrations in the assays for sFlt-1 and PlGF were 5 and 7 pg/mL, respectively. Data were reported and plotted using the Softmax software Pro 3.1.1 (Molecular Devices, Sunnyvale, Calif.). The inter-assay and intra-assay coefficients of variation varied from 3 to 10%. Urinary levels of sFlt-1 PlGF, and proteins were normalized to urinary creatinine concentrations. As previously reported, uFP (log [sFlt/PlGF×100]) was calculated as a better indicator of PE than either analyte alone.

Urine Proteomics Scores (UPS) were derived from surface-enhanced laser desorption ionization time-of-flight (SELDI-TOF) tracings as previously published. We assayed individually each urine sample using reverse phase hydrophobic surfaces H4 and H50 chips (BioRad, La Jolla, Calif.). Thirteen biomarkers peaks (P1-P13) in the 2.3-17.5 kDa mass region compose the urine proteomic profile characteristic for PE. For each peak designated as biomarker, the experimental mass (indicator of identity) and its signal-to-noise ratio (indicator of relative abundance) were calculated. Two objective urine proteomic scores were calculated: UPSb (Boolean score) representing the sum of Boolean indicators (1: present; 0: absent) assigned to each biomarker and UPSr (ranked score) with merged semi-quantitative information of present biomarkers calculated as UPSr=Σx(S/N)/10+1, where "x" includes the biomarkers with Boolean indicators of 1.

Testing for Oligomeric State Immunoreactivity

The primary antibodies employed for immunodetection of soluble oligomers have been developed and characterized in prior publications by members or our team. The following primary polyclonal antibodies were used: A11, OC, and anti-APF that recognize specific quaternary structure epitopes formed by amyloidogenic proteins.

A11 recognizes prefibrillar oligomers (PFOs)

OC detects mature fibrils anti-APF reacts with annular protofibrils (αAPF).

A dot blot technique was used to optimized to minimize nonspecific binding of the secondary antibody to the FLC component of the aggregates. Duplicate samples of urine normalized to contain 40 μg protein/spot were applied to nitrocellulose membranes, allowed to dry at room temperature, then blocked with 10% nonfat milk in Tris-buffered saline (TBS) at room temperature for 2 h. Primary antibodies were diluted in 5% milk at either 1:1,000 (A11) or 1:5,000 (OC and αAPF) dilution. After overnight incubation at 4° C., the membranes were washed 4 times with TBS-T and then incubated 1-hour at room temperature with biotinylated goat anti-rabbit IgG (H+L) (Fab'2) (Jackson Immunoresearch, West Grove, Pa.) diluted 1:5,000 in 5% milk/TBS-T. Membranes were washed again and then incubated with streptavidin-horseradish peroxidase (HRP) in TBS-T without milk (1:8,000, GE Healthcare, Kings Park, N.Y.). Finally, membranes were washed three times with TBS-T and developed with ECL chemiluminescence (GE Healthcare).

Protocol for CR-Assisted Precipitation

Given its self-assembling properties and affinity for metastable polypeptide associations, CR is known to induce amyloid oligomer growth and nucleation in aqueous solutions. As the CR-bound aggregates grow, they precipitate out of solution and can be isolated by centrifugation. Based on these principles, we developed a protocol for CR-assisted precipitation of urine samples to further characterize the congophilia and the misfoldome of PE. 10 mL volumes of urine were first spun at 15,000 g for 15 min and 4° C. The supernatant was mixed with 200 µl CR stock solution, vortexed for 1-hour as for the CRD test and spun again thereafter to pellet congophilic aggregated protein. The pellet was resuspended in water and recollected 3 times through centrifugation to remove all unbound CR. The final CR precipitate was resuspended in 50 µl water and either imaged immediately or stored frozen at −80° C. for subsequent analyses. If no pellet was visible, the specimen was deemed CR precipitate-negative but the microfuge was processed identically as for the CR precipitate-positive samples.

Polarized Microscopy, Transmission Electron Microscopy (TEM) and Cryo-TEM

CR-precipitates were resuspended in water, dried on a microscope slide, and imaged under polarized light using an Olympus U-STP microscope equipped with an Olympus OLY-200 digital camera (Olympus, Melville, N.Y.). Alternatively, the suspension was placed onto 200 mesh formvar/carbon-coated nickel grids after positive or negative staining with 2% uranyl acetate. Specimens from tubes attempting to prepare CR precipitates P-CRL women were also examined. For cryo-TEM CR precipitates were fixed 4% paraformaldehyde/0.1% gluteraldehyde in 10 mM HEPES (pH7.4) with 0.9% sodium chloride for 30 min, then rinsed, spun and re-suspended in 10% gelatin. Samples were then processed as for ultracryotomy as previously described. Ultrathin cryo-sections were single labeled with either rabbit anti-SERPINA1 (1:500, LabVision, Freemont, Calif.) or goat anti-human albumin (1:500, Bethyl Laboratories, Montgomery, Tex.) bridged using rabbit anti-goat antibody (1:200, Jackson Immunoresearch) and protein A coupled to 10 nm gold (Cell Microscopy Center, Utrecht, Netherlands). Double-labeled grids used the primary goat anti-albumin 1: 500 and 5 nm protein A-gold followed by rabbit anti-SERPINA1 and 10 nm protein A-gold. All samples were viewed in a Tecnai 12 BioTWIN electron microscope (FEI/Phillips, Hillsboro, Oreg.) equipped with a Morada digital camera and Olympus imaging software. FEI Tencai Biotwin TEM at 80 Kv. Images were taken using Morada CCD and iTEM (Olympus) software.

Techniques for Protein Identification and Validation by Western Blotting

CR precipitates were resuspended in reducing Laemelli buffer (BioRad) and boiled for 10 min. Samples were loaded onto 10% SDS-PAGE gels and stained with Commassie blue. Visible bands were excised and processed for tryptic digestion on the Ettan TA Digester (GE Healthcare). Automated MALDI-MS/MS spectra were acquired on the 4800 TOF/TOF proteomics analyzer (Applied Biosystems, Foster City, Calif.). The resulting peptide sequences were uploaded in the web-accessible Yale Protein Expression Database (YPED http://medicine.yale.edu/keck/proteomics/yped/index.aspx). Probability Mow se scores >53 were considered indicative of extensive homology. The following proteins were found represented: SERPINA1, albumin, ceruloplasmin, IgG KFLC and interferon-inducible protein 6-16 (IFI6-16 also known as G1P3). These identities were validated by Western blotting in precipitates isolated from urine of other 60 cases. Precipitates were reduced with Laemelli buffer and electrophoresed on 4-20% SDS-PAGE gels which were transferred to PVDF membranes. The following primary antibodies were used: rabbit anti-SERPINA1 (1:1,000, LabVision), goat anti-albumin (1:1,000, Bethyl Laboratories), mouse anti-ceruloplasmin (clone 3B11, 1:1,000 Thermo Scientific, Rockford, Ill.), mouse anti-KFLC (clone MEN09, 1:1,000 Novus Biologicals, Littleton, Colo.), rabbit anti-G1P3 (1:300, Proteintech, Chicago, Ill.). Blots were detected with appropriate biotinylated secondary antibodies (1:5,000, Jackson Immunoresearch) followed by streptavidin-HRP (1:8,000, GE Healthcare) and ECL chemiluminescence (GE Healthcare).

Analysis for Aggregation Propensity of G1P3

Sequences were analyzed using AGGRESCAN, a web-based algorithm for calculation and visualization of aggregation propensity. This algorithm has been shown to anticipate aggregation of protein segments involved in several conformational disorders. It has also been shown to differentiate various classes of proteins by their aggregation and solubility properties. Natively unfolded proteins were predicted to have the lowest aggregation propensity. In the AGGRESCAN output the sequence stretches with the highest predicted aggregation propensity appear as peaks in the profile plots. A polypeptide sequence is considered a "hot spot" if there are 5 or more sequentially continuous residues with an average aggregation propensity value (a4v) per amino acid larger than the hot spot threshold (HST). The AGGRESCAN parameters are listed in Table 4.

Western Blotting for APP and Aβ Epitopes

Urine or CR precipitate samples were reduced with Laemelli buffer and electrophoresed on 4-20% SDS-PAGE gels, which were transferred to PVDF membranes. The following primary antibodies were used: mouse monoclonal anti-APP (1:1,000, MAB348, clone 22C11; against N-terminal epitope amino acids 66-81 of APP, Millipore); mouse monoclonal anti-APP (1:259MAB5354, raised against the KPI domain of APP, Millipore), mouse monoclonal anti-Alz90 (1:250, MAB349, raised against a synthetic peptide corresponding to amino acids 511-608 of APP, Millipore, Billerica, Mass.) and mouse monoclonal DE2B4 (1:1,000 raised against residues 1-17 of human Aβ, Novus, Littleton, Colo.). A different blot was exposed for each antibody (blots were not stripped and reprobed). Human albumin (purified from plasma) or recombinant expressed in rice (Sigma) was used to rule out possible non-specific cross-reactivity of anti-APP antibodies. Alzheimer's brain tissue lysate (Novus, Littleton, Colo.) was used a positive control. Blots were detected with biotinylated goat anti-mouse secondary antibody (1:5,000, Jackson Immunoresearch) followed by streptavidin-HRP (1:8,000, GE Healthcare) and ECL chemiluminescence (GE Healthcare).

Immunoassays for Total Soluble APP (sAPP) and ADAM10 sAPP was measured in urine and paired serum samples by ELISA (sAPP: IBL International, Hamburg, Germany). Appropriately diluted samples (urine 2-fold, serum 50-fold) were placed in 96-well plates precoated with a capture antibody directed against an epitope common to both sAPPα (cleavage product of α-secretase) and sAPPβ (cleavage product of β-secretase). For the ADAM10 ELISA (Cosmo-Bio USA, Carlsbad, Calif.) maternal serum was diluted 3-fold. Incubation and washing protocols were performed as instructed by the manufacturers followed by reading at 450 nm with wavelength correction. Data were reported and plotted using the Softmax software Pro 3.1.1 (Molecular Devices, Sunnyvale, Calif.).

Quantitative Real-Time RT-PCR

RNA was extracted and reverse transcribed into cDNA with random hexamer primers using standard procedures. RT-PCR was performed using TaqMan (Applied Biosystems, Carlsbad, Calif.) chemistry in 20 µL reactions composed of 10 µL mastermix (TaqMan® Fast Universal PCR 2× Master Mix), 8 µL water, 1 µL cDNA template normalized at and 1 µL PCR probe set (TaqMan® Gene Expression Assays on Demand). The probes (Applied Biosystems) used for analysis were as follows: amyloid precursor protein/protease nexin-II (APP, Hs01552282 ml), A-Disintegrin and Metalloprotease-10 (ADAM10, Hs00153853_m1), ADAM17 (Hs01041915_m1), BACE-1 (Hs00201573 ml), BACE-2 (Hs00273238_m1), Presenilin-1 (PSEN1, Hs00240518_m1) and Presenilin-2 (PSEN2, Hs00240982_m1). Beta-2 microglobulin (B2M; Hs99999907_m1) and ribosomal protein L30 (RPL30, Hs00265497_m1) were used as endogenous controls. The combination of these two endogenous control mRNAs (B2M and RPL30) was validated in preliminary experiments using pools of cDNA from either PEs or CRLs tissues (placenta or amniochorion) amplified in the TaqMan® Human Endogenous Control Plate (Applied Biosystems). Selection of the two reference genes was based on low cycle threshold (Ct) values that were not different among the six cDNA pools. For each target, amplification was performed in duplicate reactions in a 2-step cycle (denaturation, 95° C. for 15 seconds, annealing/extension at 62° C. for 60 seconds) for 40 cycles. Post-processing calculations were performed using the StepOne Software (v2.1). The values obtained were normalized to the geometric mean of the endogenous control RNAs using calculations of dCt (deltaCt: Ct of the target−Ct mean of endogenous controls). A dCt of 0 indicates a ratio of 1 between the target and housekeeping genes and can be used as an indication of relative abundance between different targets and among different tissues. Calculation of ddCt (dCt of individual sample−dCt of same target in reference sample) adds an additional view within target normalization and is a better estimate of relative mRNA abundance between different biological groups. For ddCt calculations we used an RNA pool from all samples.

Immunohistochemistry

5 µm paraffin sections of placental villous tissue were deparaffinized in xylene and rehydrated with graded ethanol to potassium-phosphate-buffered saline solution, pH 7.2. Following antigen retrieval with citrate buffer, the sections were pretreated with 1% hydrogen peroxide for 15-min. followed by blocking, overnight incubation (at 4° C.) with the following primary antibodies: mouse monoclonal anti-Alz90 (1:250), mouse monoclonal DE2B4 (1:1,000), goat anti-ADAM10 (1:200, R&D Systems, Minneapolis, Minn.), goat anti-ADAM17 (1:50 R&D Systems), mouse monoclonal anti-BACE1 (1:150, MO2, clone 2C13, Abnova, Taipei, Taiwan), rabbit anti-BACE2 (1:200, Novus, Littleton, Colo.) and rabbit monoclonal anti-PSEN1 (1:100, Abcam, Cambridge, Mass.) and rabbit monoclonal anti-PSEN2 (1:100, Abcam). Trophoblastic epithelial cells and placental macrophages were identified on select sections as previously described using mouse monoclonal anti-cytokeratin-7 (1:100, Zymed/Invitrogen, Carlsbad, Calif.) or mouse monoclonal anti-CD163 Neomarkers, Fremont Calif.) antibodies, respectively (110, 111). After 1 h incubation at room temperature with the appropriate biotinylated secondary antibody (1:600, Jackson Immunochemicals), detection was performed using avidin-biotin staining (Vectastain Elite ABC, Vector Laboratories, Burlingame, Calif.) with Vector NovaRed (Vector Laboratories) as chromogen and hematoxylin as counterstain. The tissue sections were dehydrated in graded ethanols, cleared, and mounted. Negative control slides were incubated with rabbit or mouse isotype IgG as appropriate.

References (Each of which is Incorporated by Reference Herein)

1. K. S. Khan, D. Wojdyla, L. Say, A. M. Gulmezoglu, P. F. Van Look, WHO analysis of causes of maternal death: a systematic review. Lancet 367, 1066 (Apr. 1, 2006).
2. A. H. Shennan, C. Redman, C. Cooper, F. Milne, Are most maternal deaths from pre-eclampsia avoidable? Lancet 379, 1686 (May 5, 2012).
3. ACOG practice bulletin. Diagnosis and management of preeclampsia and eclampsia. Number 33, January 2002. American College of Obstetricians and Gynecologists. (2002).
4. B. M. Sibai, C. L. Stella, Diagnosis and management of atypical preeclampsia-eclampsia. American journal of obstetrics and gynecology 200, 481 el (May, 2009).
5. B. Sibai, G. Dekker, M. Kupferminc, Pre-eclampsia. Lancet 365, 785 (Feb. 26-Mar. 4, 2005).
6. A. A. Shamshirsaz, M. Paidas, G. Krikun, Preeclampsia, hypoxia, thrombosis, and inflammation. Journal of pregnancy 2012, 374047 (2012).
7. B. M. Sibai, Biomarker for hypertension-preeclampsia: are we close yet? American journal of obstetrics and gynecology 197, 1 (July, 2007).
8. W. Ramma et al., The elevation in circulating anti-angiogenic factors is independent of markers of neutrophil activation in preeclampsia. Angiogenesis 15, 333 (September, 2012).
9. R. Boij et al., Biomarkers of coagulation, inflammation, and angiogenesis are independently associated with preeclampsia. American journal of reproductive immunology 68, 258 (September, 2012).
10. U. D. Anderson, M. G. Olsson, K. H. Kristensen, B. Akerstrom, S. R. Hansson, Review: Biochemical markers to predict preeclampsia. Placenta 33 Suppl, S42 (February, 2012).
11. I. A. Buhimschi et al., Proteomic profiling of urine identifies specific fragments of SERPINA1 and albumin as biomarkers of preeclampsia. American journal of obstetrics and gynecology 199, 551 el (November, 2008).
12. J. A. Huntington, Serpin structure, function and dysfunction. Journal of thrombosis and haemostasis: JTH 9 Suppl 1, 26 (July, 2011).
13. P. Frid, S. V. Anisimov, N. Popovic, Congo red and protein aggregation in neurodegenerative diseases. Brain research reviews 53, 135 (January, 2007).
14. R. Kayed et al., Annular protofibrils are a structurally and functionally distinct type of amyloid oligomer. The Journal of biological chemistry 284, 4230 (Feb. 13, 2009).
15. R. Kayed et al., Common structure of soluble amyloid oligomers implies common mechanism of pathogenesis. Science 300, 486 (Apr. 18, 2003).
16. R. Kayed et al., Fibril specific, conformation dependent antibodies recognize a generic epitope common to amyloid fibrils and fibrillar oligomers that is absent in prefibrillar oligomers. Molecular neurodegeneration 2, 18 (2007).
17. C. G. Glabe, Common mechanisms of amyloid oligomer pathogenesis in degenerative disease. Neurobiology of aging 27, 570 (April, 2006).
18. M. A. Smith, P. L. Richey, R. N. Kalaria, G. Perry, Elastase is associated with the neurofibrillary pathology of Alzheimer disease: a putative link between proteolytic imbalance and oxidative stress. Restorative neurology and neuroscience 9, 213 (Jan. 1, 1996).
19. M. A. Salameh et al., The amyloid precursor protein/protease nexin 2 Kunitz inhibitor domain is a highly specific substrate of mesotrypsin. The Journal of biological chemistry 285, 1939 (Jan. 15, 2010).
20. M. Halimi et al., Prion urine comprises a glycosaminoglycan-light chain IgG complex that can be stained by Congo red. Journal of virological methods 133, 205 (May, 2006).
21. R. P. Linke, Highly sensitive diagnosis of amyloid and various amyloid syndromes using Congo red fluorescence. Virchows Archiv: an international journal of pathology 436, 439 (May, 2000).
22. W. E. Klunk, R. F. Jacob, R. P. Mason, Quantifying amyloid beta-peptide (Abeta) aggregation using the Congo red-Abeta (CR-abeta) spectrophotometric assay. Analytical biochemistry 266, 66 (Jan. 1, 1999).
23. R. J. Guidotti, D. (2005).
24. C. S. Buhimschi et al., Urinary angiogenic factors cluster hypertensive disorders and identify women with severe preeclampsia. American journal of obstetrics and gynecology 192, 734 (March, 2005).
25. Y. Yoshiike, R. Kayed, S. C. Milton, A. Takashima, C. G. Glabe, Pore-forming proteins share structural and functional homology with amyloid oligomers. Neuromolecular medicine 9, 270 (2007).
26. Y. Yoshiike et al., Amyloid oligomer conformation in a group of natively folded proteins. PloS one 3, e3235 (2008).
27. E. Cerf et al., Antiparallel beta-sheet: a signature structure of the oligomeric amyloid beta-peptide. The Biochemical journal 421, 415 (Aug. 1, 2009).
28. A. Laganowsky et al., Atomic view of a toxic amyloid small oligomer. Science 335, 1228 (Mar. 9, 2012).
29. T. Shirahama, A. S. Cohen, High-resolution electron microscopic analysis of the amyloid fibril. The Journal of cell biology 33. 679 (June, 1967).
30. J. D. Sipe, A. S. Cohen, Review: history of the amyloid fibril. Journal of structural biology 130, 88 (June, 2000).
31. H. Z. Malina, System in biology leading to cell pathology: stable protein-protein interactions after covalent modifications by small molecules or in transgenic cells. Journal of biomedical science 18, 7 (2011).
32. N. E. Hellman, S. Kono, H. Miyajima, J. D. Gitlin, Biochemical analysis of a missense mutation in aceruloplasminemia. The Journal of biological chemistry 277, 1375 (Jan. 11, 2002).
33. P. G. Winyard et al., Effects of oxidative stress on some physiochemical properties of caeruloplasmin. The Biochemical journal 258, 435 (Mar. 1, 1989).
34. S. Kumar et al., Serum immunoglobulin free light-chain measurement in primary amyloidosis: prognostic value and correlations with clinical features. Blood 116, 5126 (Dec. 9, 2010).
35. J. M. Kelly et al., Characterization of a human gene inducible by alpha- and beta-interferons and its expression in mouse cells. The EMBO journal 5, 1601 (July, 1986).
36. M. G. Turri, K. A. Cuin, A. C. Porter, Characterisation of a novel minisatellite that provides multiple splice donor sites in an interferon-induced transcript. Nucleic acids research 23, 1854 (Jun. 11, 1995).
37. F. Chiti, C. M. Dobson, Protein misfolding, functional amyloid, and human disease. Annual review of biochemistry 75, 333 (2006).
38. O. Conchillo-Sole et al., AGGRESCAN: a server for the prediction and evaluation of "hot spots" of aggregation in polypeptides. BMC bioinformatics 8, 65 (2007).
39. M. F. Knauer, B. Soreghan, D. Burdick, J. Kosmoski. C. G. Glabe, Intracellular accumulation and resistance to degradation of the Alzheimer amyloid A4/beta protein. Proceedings of the National Academy of Sciences of the United States of America 89, 7437 (Aug. 15, 1992).
40. D. Goldgaber, M. I. Lerman, O. W. McBride, U. Saffiotti, D. C. Gajdusek, Characterization and chromosomal localization of a cDNA encoding brain amyloid of Alzheimer's disease. Science 235, 877 (Feb. 20, 1987).
41. J. Kang, B. Muller-Hill, Differential splicing of Alzheimer's disease amyloid A4 precursor RNA in rat tissues: PreA4(695) mRNA is predominantly produced in rat and human brain. Biochemical and biophysical research communications 166, 1192 (Feb. 14, 1990).
42. B. De Strooper, R. Vassar, T. Golde, The secretases: enzymes with therapeutic potential in Alzheimer disease. Nature reviews. Neurology 6, 99 (February 2010).
43. I. Caille et al., Soluble form of amyloid precursor protein regulates proliferation of progenitors in the adult subventricular zone. Development 131, 2173 (May, 2004).
44. A. Schmitz, R. Tikkanen. G. Kirfel, V. Herzog, The biological role of the Alzheimer amyloid precursor protein in epithelial cells. Histochemistry and cell biology 117, 171 (February, 2002).
45. J. Hoffmann, C. Twiesselmann, M. P. Kummer, P. Romagnoli, V. Herzog, A possible role for the Alzheimer amyloid precursor protein in the regulation of epidermal basal cell proliferation. European journal of cell biology 79, 905 (December, 2000).
46. C. Haass, D. J. Selkoe, Cellular processing of beta-amyloid precursor protein and the genesis of amyloid beta-peptide. Cell 75, 1039 (Dec. 17, 1993).
47. H. J. Clarris, B. Key, K. Beyreuther, C. L. Masters, D. H. Small, Expression of the amyloid protein precursor of Alzheimer's disease in the developing rat olfactory system. Brain research. Developmental brain research 88, 87 (Aug. 28, 1995).
48. V. Muresan, N. H. Varvel, B. T. Lamb, Z. Muresan, The cleavage products of amyloid-beta precursor protein are sorted to distinct carrier vesicles that are independently transported within neurites. The Journal of neuroscience: the official journal of the Society for Neuroscience 29, 3565 (Mar. 18, 2009).
49. T. Oltersdorf et al., The secreted form of the Alzheimer's amyloid precursor protein with the Kunitz domain is protease nexin-II. Nature 341, 144 (Sep. 14, 1989).
50. L. Ho, K. Fukuchi, S. G. Younkin, The alternatively spliced Kunitz protease inhibitor domain alters amyloid beta protein precursor processing and amyloid beta protein production in cultured cells. The Journal of biological chemistry 271, 30929 (Nov. 29, 1996).
51. M. Barrachina et al., Amyloid-beta deposition in the cerebral cortex in Dementia with Lewy bodies is accompanied by a relative increase in AbetaPP mRNA isoforms containing the Kunitz protease inhibitor. Neurochemistry international 46, 253 (February, 2005).
52. Rare Disease Act of 2002 (accesed Jan. 10, 2013 at http://www.gpo.gov/fdsys/pkg/PLAW-107pub1280/html/PLAW-107pub1280.htm).
53. E. F. Funai et al., Long-term mortality after preeclampsia. Epidemiology 16, 206 (March, 2005).
54. F. H. Harlow, M. A. Brown, The diversity of diagnoses of preeclampsia. Hypertension in pregnancy: official journal of the International Society for the Study of Hypertension in Pregnancy 20, 57 (2001).
55. P. Zhang, M. Schmidt, L. Cook, Maternal vasculopathy and histologic diagnosis of preeclampsia: poor correlation 56. R. J. Perrin, A. M. Fagan, D. M. Holtzman, Multimodal techniques for diagnosis and prognosis of Alzheimer's disease. Nature 461, 916 (Oct. 15, 2009).
57. J. C. Morris et al., Cerebral amyloid deposition and diffuse plaques in "normal" aging: Evidence for presymptomatic and very mild Alzheimer's disease. Neurology 46, 707 (March, 1996).
58. P. V. Arriagada, K. Marzloff, B. T. Hyman, Distribution of Alzheimer-type pathologic changes in nondemented elderly individuals matches the pattern in Alzheimer's disease. Neurology 42, 1681 (September, 1992).
59. P. T. Nelson et al., Correlation of Alzheimer disease neuropathologic changes with cognitive status: a review of the literature. Journal of neuropathology and experimental neurology 71, 362 (May, 2012).
60. A. Serrano-Pozo et al., Stable size distribution of amyloid plaques over the course of Alzheimer disease. Journal of neuropathology and experimental neurology 71, 694 (August, 2012).
61. E. A. Oliver et al., Activation of the receptor for advanced glycation end products system in women with severe preeclampsia. The Journal of clinical endocrinology and metabolism 96, 689 (March, 2011).
62. X. Zhang, W. Le, Pathological role of hypoxia in Alzheimer's disease. Experimental neurology 223, 299 (June, 2010).
63. C. Ruiz de Almodovar, D. Lambrechts, M. Mazzone, P. Carmeliet, Role and therapeutic potential of VEGF in the nervous system. Physiological reviews 89, 607 (April, 2009).
64. G. Eskici, P. H. Axelsen, Copper and oxidative stress in the pathogenesis of Alzheimer's disease. Biochemistry 51, 6289 (Aug. 14, 2012).
65. P. Grammas, Neurovascular dysfunction, inflammation and endothelial activation: implications for the pathogenesis of Alzheimer's disease. Journal of neuroinflammation 8, 26 (2011).
66. E. Eiland, C. Nzerue, M. Faulkner, Preeclampsia 2012. Journal of pregnancy 2012, 586578 (2012).
67. R. Deane et al., RAGE mediates amyloid-beta peptide transport across the blood-brain barrier and accumulation in brain. Nature medicine 9, 907 (July, 2003).
68. L. F. Lue, S. D. Yan, D. M. Stern, D. G. Walker, Preventing activation of receptor for advanced glycation endproducts in Alzheimer's disease. Current drug targets. CNS and neurological disorders 4, 249 (June, 2005).
69. A. J. Howie, D. B. Brewer, Optical properties of amyloid stained by Congo red: history and mechanisms. Micron 40, 285 (April, 2009).
70. C. Wu, Z. Wang, H. Lei, W. Zhang, Y. Duan, Dual binding modes of Congo red to amyloid protofibril surface observed in molecular dynamics simulations. Journal of the American Chemical Society 129, 1225 (Feb. 7, 2007).
71. UNICEF-WHO, Antenatal Care in Developing Countries: Promises, Achievements and Missed Opportunities. World Health Organization, Geneva, Switzerland, (2003).
72. N. Murray et al., The clinical utility of routine urinalysis in pregnancy: a prospective study. The Medical journal of Australia 177, 477 (Nov. 4, 2002).
73. S. Thangaratinam et al., Estimation of proteinuria as a predictor of complications of pre-eclampsia: a systematic review. BMC medicine 7, 10 (2009).
74. I. H. Hinberg, L. Katz, L. Waddell, Sensitivity of in vitro diagnostic dipstick tests to urinary protein. Clinical biochemistry 11, 62 (April, 1978).
75. V. Maisnar et al., The problems of proteinuria measurement in urine with presence of Bence Jones protein. Clinical biochemistry 44, 403 (April, 2011).
76. N. Parker, A. C. Porter, Identification of a novel gene family that includes the interferon-inducible human genes 6-16 and ISG12. BMC genomics 5, 8 (Jan. 19, 2004).
77. M. Rosenzweig, H. Landau, Light chain (AL) amyloidosis: update on diagnosis and management. Journal of hematology & oncology 4, 47 (2011).
78. M. R. Hayden, S. C. Tyagi, M. M. Kerklo, M. R. Nicolls, Type 2 diabetes mellitus as a conformational disease. JOP: Journal of the pancreas 6, 287 (July, 2005).
79. J. H. Kang, K. S. Kim, S. Y. Choi, H. Y. Kwon, M. H. Won, Oxidative modification of human ceruloplasmin by peroxyl radicals. Biochimica et biophysica acta 1568, 30 (Nov. 7, 2001).
80. S. W. Griffiths, C. L. Cooney, Relationship between protein structure and methionine oxidation in recombinant human alpha 1-antitrypsin. Biochemistry 41, 6245 (May 21, 2002).
81. G. Joslin, R. J. Fallon, J. Bullock, S. P. Adams, D. H. Perlmutter, The SEC receptor recognizes a pentapeptide neodomain of alpha 1-antitrypsin-protease complexes. The Journal of biological chemistry 266, 11282 (Jun. 15, 1991).
82. G. Joslin et al., Amyloid-beta peptide, substance P, and bombesin bind to the serpin-enzyme complex receptor. The Journal of biological chemistry 266, 21897 (Nov. 15, 1991).
83. L. O. Tjernberg et al., Arrest of beta-amyloid fibril formation by a pentapeptide ligand. The Journal of biological chemistry 271, 8545 (Apr. 12, 1996).
84. R. T. Turner, 3rd et al., Subsite specificity of memapsin 2 (beta-secretase): implications for inhibitor design. Biochemistry 40, 10001 (Aug. 28, 2001).
85. M. T. Gersbacher, D. Y. Kim, R. Bhattacharyya, D. M. Kovacs, Identification of BACE1 cleavage sites in human voltage-gated sodium channel beta 2 subunit. Molecular neurodegeneration 5, 61 (2010).
86. B. Bohrmann et al., Endogenous proteins controlling amyloid beta-peptide polymerization. Possible implications for beta-amyloid formation in the central nervous system and in peripheral tissues. The Journal of biological chemistry 274, 15990 (Jun. 4, 1999).
87. P. A. Gollin, R. N. Kalaria, P. Eikelenboom, A. Rozemuller, G. Perry, Alpha 1-antitrypsin and alpha 1-antichymotrypsin are in the lesions of Alzheimer's disease. Neuroreport 3, 201 (February, 1992).
88. G. J. Howlett, K. J. Moore, Untangling the role of amyloid in atherosclerosis. Current opinion in lipidology 17, 541 (October, 2006).
89. R. E. Tanzi, R. D. Moir, S. L. Wagner, Clearance of Alzheimer's Abeta peptide: the many roads to perdition. Neuron 43, 605 (Sep. 2, 2004).
90. R. W. Carrell, D. A. Lomas, Conformational disease. Lancet 350. 134 (Jul. 12, 1997).
91. S. L. Cole, R. Vassar, The Alzheimer's disease beta-secretase enzyme. BACE1. Molecular neurodegeneration 2, 22 (2007).
92. A. F. Haney, W. S. Trought. The sonolucent placenta in high-risk obstetrics. Obstetrics and gynecology 55, 38 (January, 1980).

93. V. A. Varma, K. M. Kim, Placental calcification: ultrastructural and X-ray microanalytic studies. Scanning electron microscopy, 1567 (1985).
94. O. Yokota et al., NACP/alpha-synuclein immunoreactivity in diffuse neurofibrillary tangles with calcification (DNTC). Acta neuropathologica 104, 333 (October, 2002).
95. T. Cornelis, A. Odutayo, J. Keunen, M. Hladunewich, The kidney in normal pregnancy and preeclampsia. Seminars in nephrology 31, 4 (January, 2011).
96. B. M. Sibai, Imitators of severe pre-eclampsia. Seminars in perinatology 33, 196 (June, 2009).
97. S. Hirai, K. Okamoto, Amyloid beta/A4 peptide associated with Alzheimer's disease and cerebral amyloid angiopathy. Internal medicine 32, 923 (December, 1993).
98. R. C. Pattinson, M. Hall, Near misses: a useful adjunct to maternal death enquiries. British medical bulletin 67, 231 (2003).
99. S. f. M.-F. M. Publications Committee. B. M. Sibai, Evaluation and management of severe preeclampsia before 34 weeks' gestation. American journal of obstetrics and gynecology 205, 191 (September, 2011).
100. S. Lee, K. Carson, A. Rice-Ficht, T. Good, Hsp20, a novel alpha-crystallin. prevents Abeta fibril formation and toxicity. Protein science: a publication of the Protein Society 14, 593 (March, 2005).
101. M. D. Griffin et al., Thioflavin T fluorescence in human serum: correlations with vascular health and cardiovascular risk factors. Clinical biochemistry 43, 278 (February, 2010).
102. M. Sakono, T. Zakom Amyloid oligomers: formation and toxicity of Abeta oligomers. The FEBS journal 277, 1348 (March, 2010).
103. C. P. Price, R. G. Newall, J. C. Boyd, Use of proteinxreatinine ratio measurements on random urine samples for prediction of significant proteinuria: a systematic review. Clinical chemistry 51, 1577 (September, 2005).
104. F. Schoonjans, A. Zalata, C. E. Depuydt, F. H. Comhaire, MedCalc: a new computer program for medical statistics. Computer methods and programs in biomedicine 48, 257 (December, 1995).
105. B. Efron, R. J. Tibshirani, An introduction to the bootstrap. (CRC Press. Boca Raton, Fla., 1994).
106. E. R. DeLong, D. M. DeLong, D. L. Clarke-Pearson, Comparing the areas under two or more correlated receiver operating characteristic curves: a nonparametric approach. Biometrics 44, 837 (September, 1988).
107. J. D. Green, C. Goldsbury, J. Kistler, G. J. Cooper, U. Aebi, Human amylin oligomer growth and fibril elongation define two distinct phases in amyloid formation. The Journal of biological chemistry 279, 12206 (Mar. 26, 2004).
108. J. Rybarska et al., Evidence that supramolecular Congo red is the sole ligation form of this dye for L chain lambda derived amyloid proteins. Folia histochemica et cytobiologica/Polish Academy of Sciences, Polish Histochemical and Cytochemical Society 39, 307 (2001).
109. J. W. Slot, H. J. Geuze, Cryosectioning and immunolabeling. Nature protocols 2, 2480 (2007).
110. M. J. Wehrum et al., Accreta complicating complete placenta previa is characterized by reduced systemic levels of vascular endothelial growth factor and by epithelial-to-mesenchymal transition of the invasive trophoblast. American journal of obstetrics and gynecology 204, 411 el (May, 2011).
111. Z. Tang et al., Decreased levels of folate receptor-beta and reduced numbers of fetal macrophages (Hofbauer cells) in placentas from pregnancies with severe preeclampsia. American journal of reproductive immunology 70, 104 (August, 2013).

Example 3

Study Design and Specimens

There are two parts to the CRD test. The "wet part" includes preparation of the urine-Congo Red mixture, spotting the mixture as dots on a nitrocellulose sheet (CRD sheet array) followed by acquisition and storing of the two pictures on a smartphone (Pix 1: captured before washing the sheet and Pix2 captured after the hydrophobic wash). The "dry part" includes processing of the two images followed by the calculation of the CRD test result [% Congo Red Retention (CRR)] for each dot individually and for each subject as the average of the duplicate dots on the array after subtraction of the CRR result from the Blank sample (BLK, uses phosphate buffer saline [PBS] instead of human urine). This study was conducted in 3 stages, each seeking to synergistically simplify, speed and improve both the "wet part" and the "dry part" of the CRD test.

In stage 1 a preliminary version of the image processing software tool was evaluated on stored images that have been previously processed in Adobe Photoshop (Adobe, San Jose, Calif.) in preparation for manual analysis using ImageJ software (http://imagej.nih.gov/ij/). The results of stage 1 led to development of a standardized template for consistent positioning of the sample dots during the "wet part" of the test and of a mobile phone enabled image processing tool part of the optimization of the "dry part".

In stage 2, these improvements were tested in real-time on newly prepared standardized CRD arrays and the results were analyzed for agreement against the manual protocol and for test accuracy against a disease relevant prognostic standard (medically-indicated delivery for preeclampsia: MIDPE).

In stage 3, the test results were analyzed across 4 operators, including untrained personnel without any instruction or prior knowledge of our system to check for robustness and to improve error-handling and feedback of the system. In addition, the "wet part" of the protocol was further simplified to systematically modify and/or eliminate several steps to achieve the maximum possible simplification without loss in technical performance.

The urine specimens included in this study were collected (Example 2) as part of the study that reported on the molecular basis of the CRD principle. During evaluation, the CRR calculated manually by a single expert (IAB) acted as technical gold standard. MIDPE (a preeclampsia-related near-miss event) was chosen as the outcome of interest in comparative accuracy analyses. Statistical methods are summarized below.

Evaluation of Algorithms for Dot Quantification

Figure 20A:
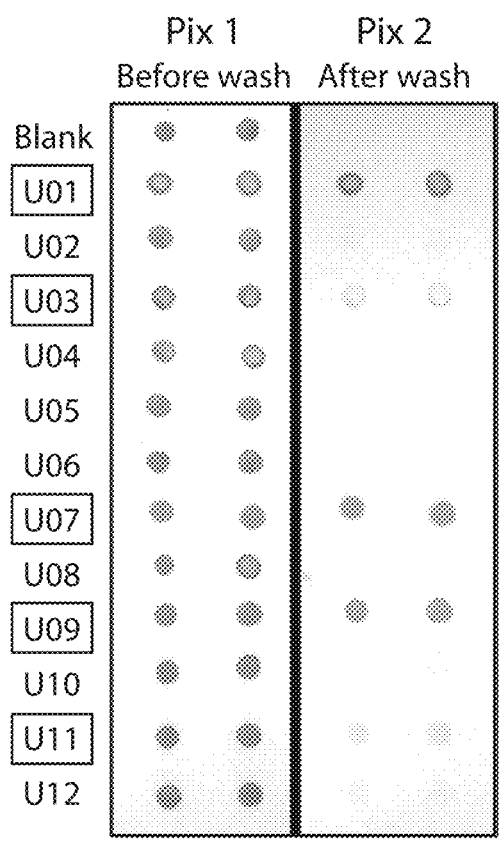
FIGS. 20A-20F show a comparison of an example of automated Congo Red retention calculation algorithms during stage 1 of the study described in Example 3.
Figure 20B:
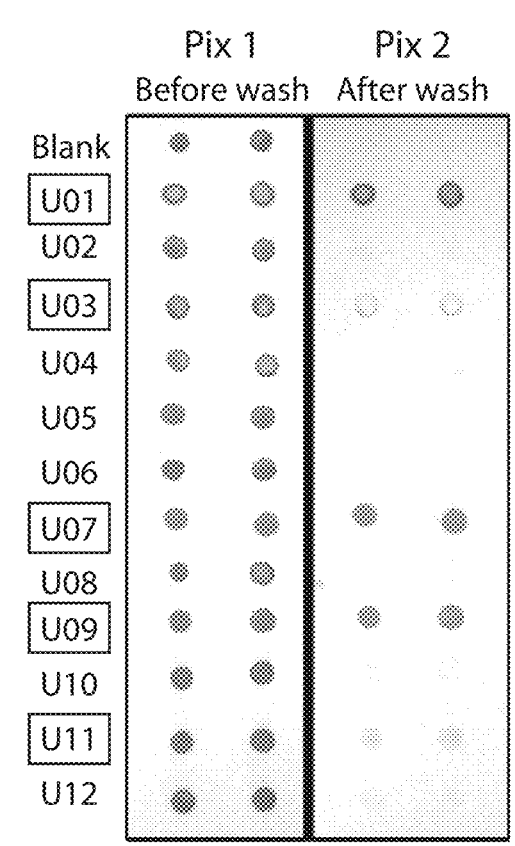
Figure 20C:
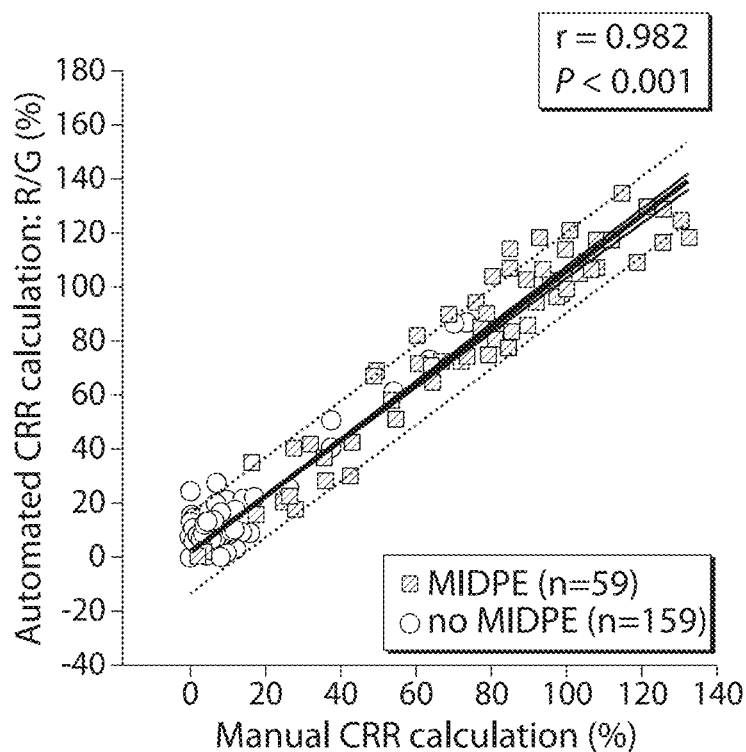
Figure 20D:
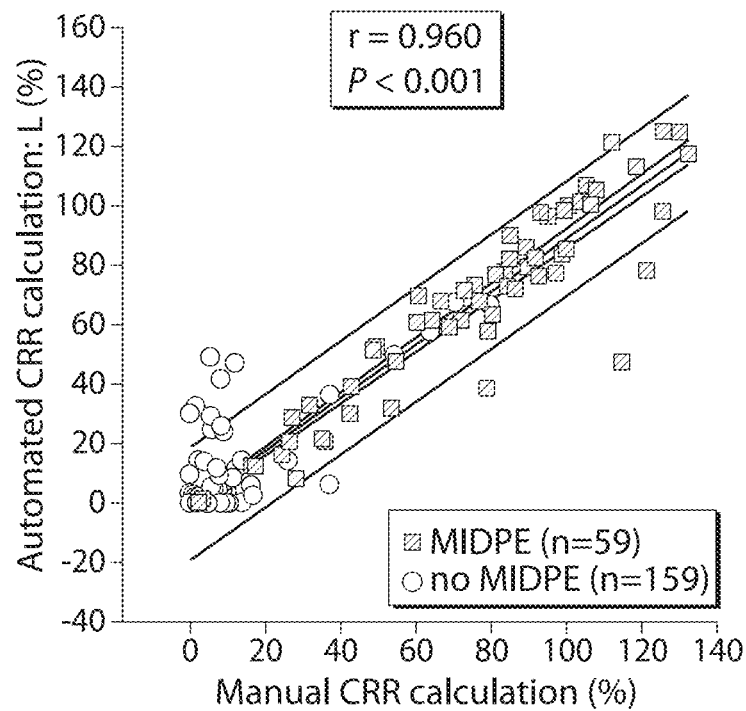
Figure 20E:
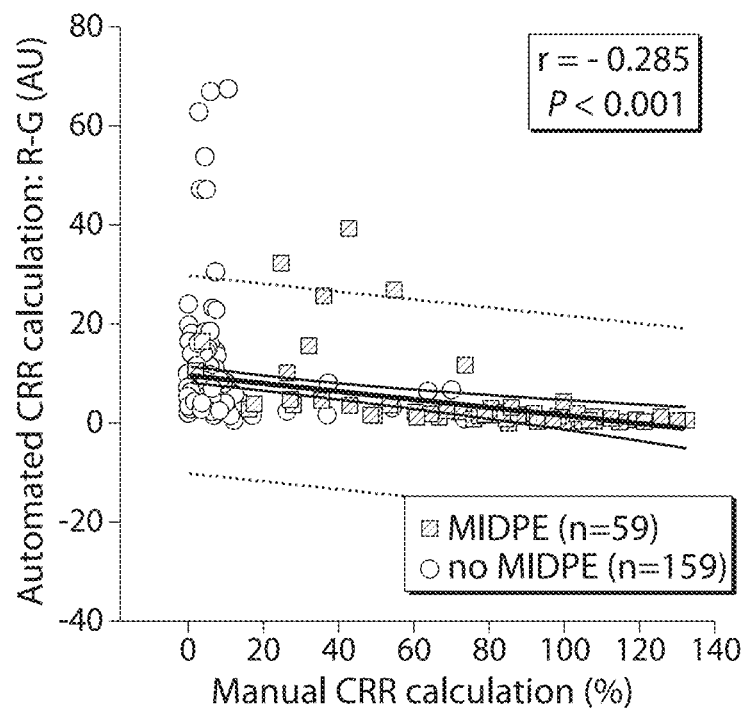
Figure 20F:
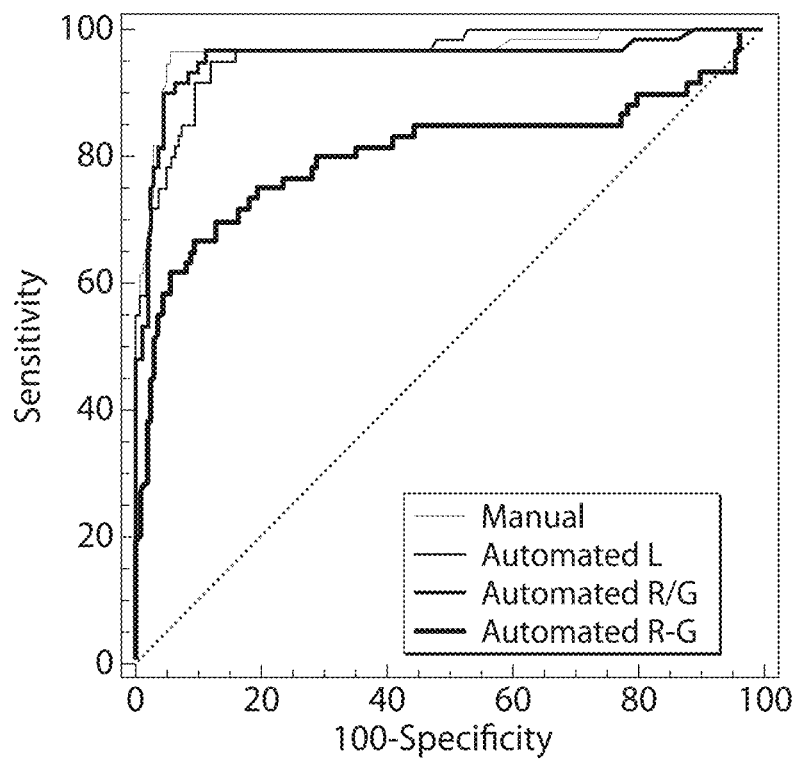

The stage 1 dataset originated from previously acquired images (before and after wash, Nikon Coolpix 4500) that have been manually quantified as part of the initial study. This data set consisted of 18 arrays from a total of 218 subjects. Each array held duplicate spots from 12-15 subjects (FIG. 20A). Based on an interest in the prominence of the red dots relative to that of the background sheet, two possible algorithms were tested, which would theoretically enhance the dye color: red channel pixel value divided by green channel (ratio R/G, with R and G ranging from 0-255), to enhance redness information by reducing background color. A second calculation used the red channel information subtracted by green channel (difference R-G) with the same reasoning. The green channel was selected over the blue channel due to the Bayer pattern which makes digital camera sensors more sensitive to green than to blue in order to match the heightened sensitivity of the human visual system towards the color green. Lastly, a luminance conversion equation was used to retain intensity of the colors while eliminating the color-information itself (FIG. 20B). The luminance (L) algorithm resembled the one employed by the manual processing routine. Simulated calculations performed with a command-line interface of our application (command-line version of the processing library run on a ThinkPad T500 with Linux Ubuntu operating system) determined that the R/G (FIG. 20C) and L (FIG. 20D) calculations returned CRR values that correlated significantly better with the manually derived CRR (z-test P<0.001 for both comparisons) compared to R-G (FIG. 20E). In comparative accuracy analysis (FIG. 20F) there was no difference between the area under the receiver operating curve (AUC) of the manually derived CRR [AUC=0.966; 95% CI [0.932-0.985]) and the CRR automatically calculated using the L conversion (0.962 [0.927-0.983], P=0.579). There was a small yet statistically significant different decrease in AUC when the CRR value was calculated as R/G (0.962 [0.927-0.983], P=0.042) compared to the manual integration. We attributed this difference to the subtle bathochromic shift (from red to purple) exhibited by selected urine specimens which impacted the R/G ratio significantly more than the L conversion. This, in addition to the general shorter processing time needed for greyscale images led us to choose the L-based algorithm for subsequent process development.

Standardization of the CRD Array Size and Layout

Figure 24:
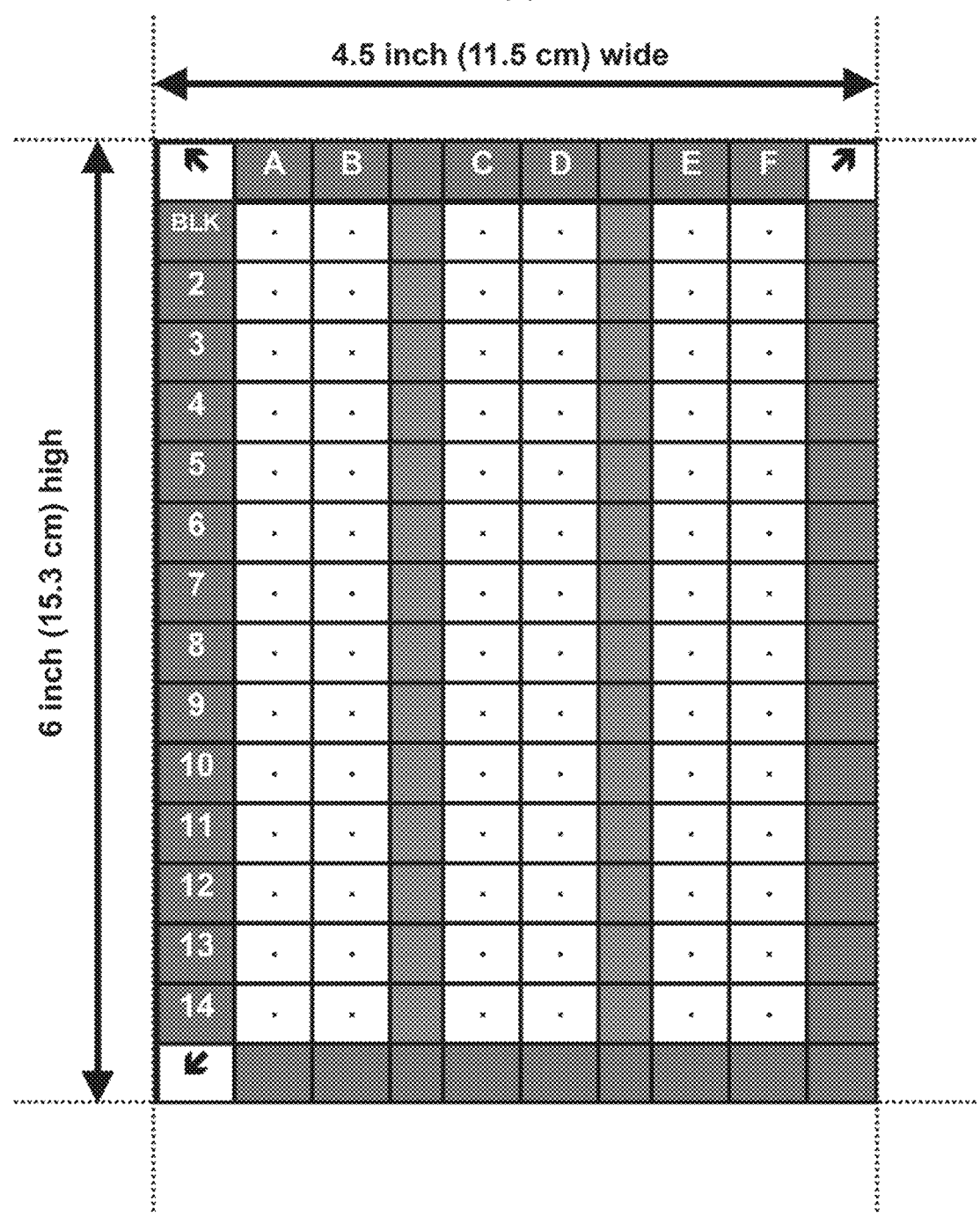
FIG. 24 shows an example of a sample positioning template for an array analysis.

For a fully automated routine, the automatic detection of the sheet as well as the consistent position of the dots on the acquired images emerged as a requirement during stage 1. In addition, the dimension and orientation of the sheet needed to be known. To achieve this, the layout of the CRD array was standardized and revisited. The modality in which Pix 1 and Pix2 were acquired was also standardized and revisited as follows: i) nitrocellulose sheets were cut to a standard size of 4.5 in wide by 6 in long which is proportional to the iPhone screen size; ii) three of the four corner squares of the sheet were punched using a handheld craft paper punch; iii) a sample positioning template (FIG. 21) was printed on sheet of plain paper, which was then placed inside a plastic sheet protector and under the nitrocellulose sheet. The true to size template was included for printout, as shown in FIG. 24. The template marks the sample positions for up to 41 subjects (each specimen is spotted in duplicate in adjacent cells of two columns). The black center points in each cell are visible through transparency and serve as a guide for sample placement to ensure the predictable dot positioning on the sheet. The sample dots corresponding to the blank (BLK or PBS) are placed in the first left corner; iv) acquisition of both Pix1 and Pix2 images is performed with the array sheet placed on a black surface, which results in the punched holes acting as position markers without the need for using ink that might percolate during the wash or other markers that might increase the cost of the sheet. This standardized format of the CRD test array borrows elements from QUICK RESPONSE® (QR) codes namely the sheet has a known aspect ratio and three of the four corners are highlighted. The detection of the three markers at the left and upper corners allows for the rotation, de-skewing and perfect superposition of each individual dot in Pix1 with its corresponding self (or position where the dye has been washed off) in Pix2. This last feature is achieved through an image processing sequence customized to run as an app on the same smartphone that is used to acquire Pix1 and Pix 2 (iPhone 4 in this case).

CRD Array Image Processing Sequence

Figure 21:
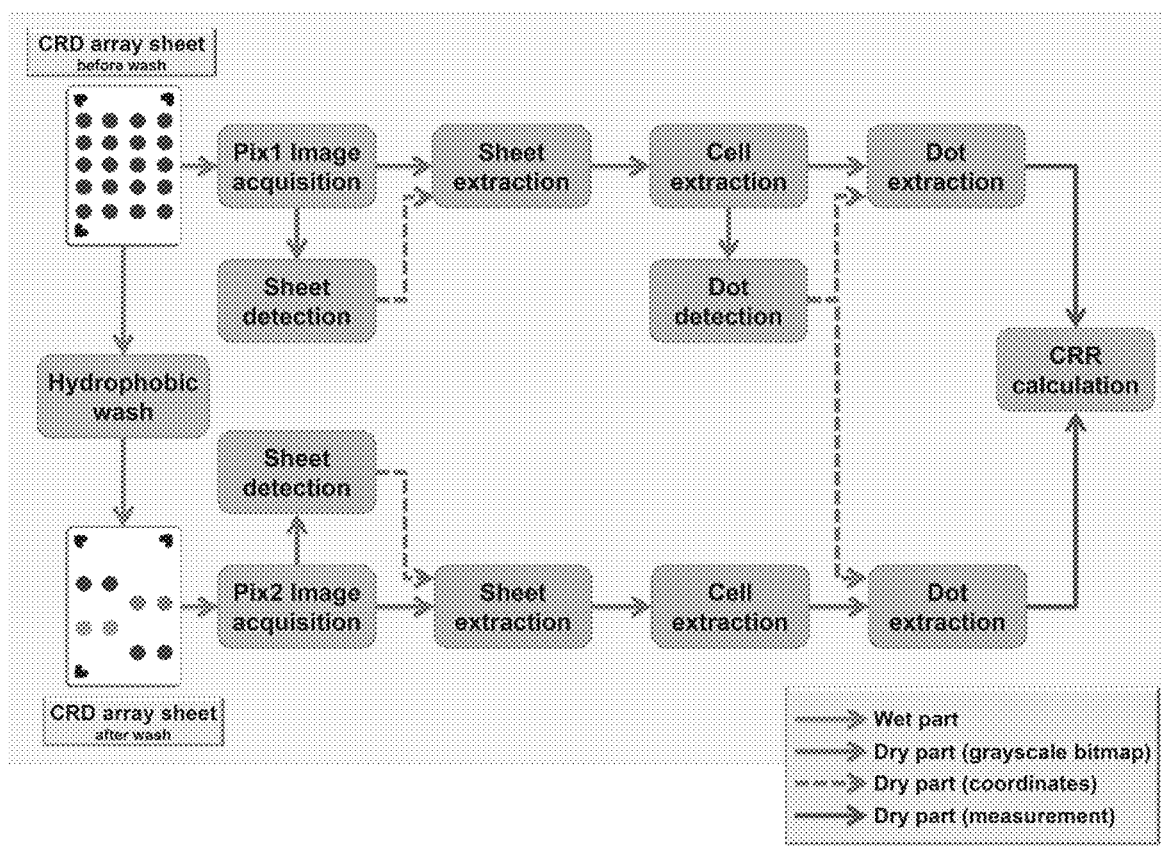
FIG. 21 shows a workflow diagram of an example of a Congo Red Dot test and image processing routine.

The sequence chains seven imaging processing steps as follows: i) acquisition of images part of the wet part of the CRD test; ii) sheet detection; iii) sheet extraction; iv) cell extraction; v) dot detection; vi) dot extraction and vii) CRR calculation. The process workflow is schematically represented in FIG. 21.

Image acquisition. The images are acquired using the build-in camera of the smartphone. The resolution of the iPhone 4 camera is sufficient to capture a sample dot with a maximum number of about 40 pixels per diameter. This results in approximately 1,200 pixels per sample dot. For speed of processing and robustness each image is converted into luminance grayscale for all the following steps.

Sheet detection. Since the exact location and deformation of the sheet due to variations in photographic angle is unknown de-skewing of perspective projection is first required. To achieve this, four corners were detected and then a simple interpolation was applied between the four corners to de-skew the sheet into a rectangular image. To find the corners, the sheet itself and then its edges have to be located. The two opposite sides of the sheet should be the same length; the corners have a 90-degree angle, and the ratio of the neighboring sides is equal to the ratio of the standardized template (0.75). For automatic detection, the grayscale input image is binarized using the Otsu method. Because the background of the image is black (due to the black photographic background visible through the punch holes) and the sheet is white, the Otsu threshold of the sheet is calculated to separate the foreground (sheet) from background. To further smooth the resulting binary image, all holes in the foreground part are filled applying mathematical morphology. Next, a gradient filter is applied to expose the sheet borders on the image. On this gradient image with over-expressed borders, the corners are detected using the Hough line transform (a method of finding lines in an image). A rough Hough line transform is first calculated to loosely find the four most prominent edges (borders of the sheet). Next, the 4 intersections of these lines are extracted. Because these positions do not match the corners perfectly, a second finer Hough line transform is performed separately on regions of interest around the previously found corners. In this second run, only the two main lines near the corners are extracted and intersected, which improves localization of the corner points while keeping memory usage to a minimum.

Sheet extraction. From the four corner points, the positions of the longer and shorter edges are estimated and the sheet is perspectively transformed into a rectangular geometry using bilinear interpolation. The geometric correction also reduces the number of pixels per dot to about 700 pixels (downscaling). To account for possible landscape versus portrait acquisition, the three position markers in the corners of the sheet are detected by calculating the average intensity in each corner and selecting the corner with the highest intensity (which corresponds to the corner without the punch-out marker) as the reference point. The sheet is transposed or rotated accordingly, such that all markers are repositioned on the upper and left corners. The normalized image now contains the sheet with the sheet spanning between the four image corners. This process is done individually on Pix1 and Pix2.

Cell extraction. The positions of the cells for each patient are extracted from the normalized image without further image processing, since the geometry of the array is well defined based on the standardized sample application template. However, each cell contains two dots at a yet unknown position. This process is done individually on Pix1 and Pix2.

Dot detection. All possible sample dots are present in Pix1 but some might disappear during washing (negative testing samples). Thus, the complete dot detection can only be performed on Pix 1. To determine the dot positions, a gradient filter is applied to each extracted cell on Pix1 to detect the dot edges. The radius of each dot is estimated. A Hough circle transform is then performed and the two most prominent circular shapes in each cell are selected. Because the relative position of the dot does not change during washing, the same position information from Pix1 is used for processing of Pix2.

Dot extraction. With the positions of the dots known, the intensity of the corresponding pixels are extracted and summed up. To account for white-balance and mild illumination changes, a background subtraction is performed by subtracting the average luminance of the cell outside the dot from the average luminance within the dot Table 5.

lence of the outcome of interest (MIDPE) in the stage 2 dataset was 40% among specimens (118/328) and among subjects (108/273).

Figures 22A, 22B, 22C:
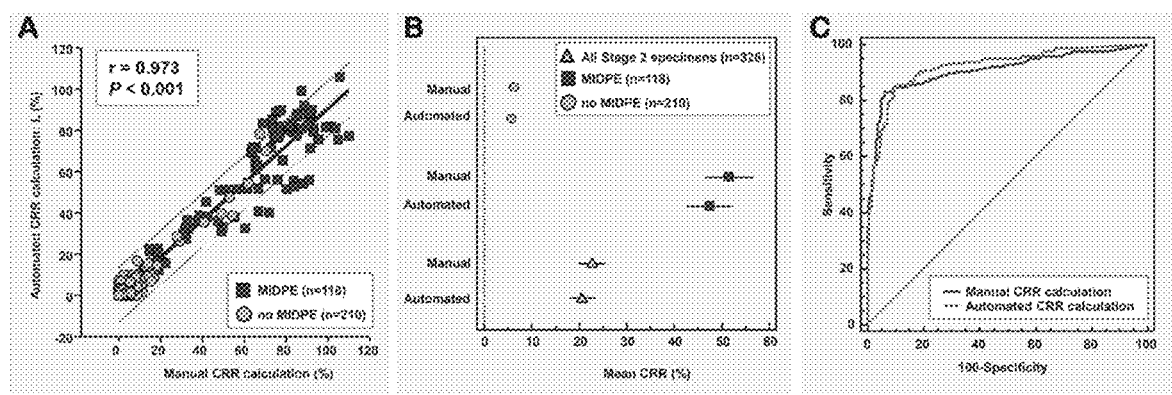
FIGS. 22A-22C show evaluation and equivalence testing of an example of a smartphone-assisted Congo Red retention calculation in stage 2 of the study described in Example 3.

Similar to stage 1, there was a significant level of agreement between the manual and the automated CRR measurements. Lin's concordance coefficient ($\rho_c$) of 0.968, 95% CI[0.961-0.974]) qualified as "substantial" based on a Pearson's precision coefficient $\rho=0.973$ and a bias correction factor Cb=0.995 (FIG. 22A). The two one-sided test (TOST) procedure determined that the smartphone-enabled CRR calculation was equivalent to the manual integration (FIG. 22B). This can be easily seen through the overlapping 90% confidence intervals of the CRRs calculated with the manual versus the automated procedure irrespective of whether the groups were analyzed combined or separated by outcome. Uniquely to TOST analysis the 90% confidence intervals correspond to the P=0.05 significance level. The margin of equivalence was 10% for the MIDPE group and 5% for the group without MIDPE and the overall dataset. An ROC analysis using the first specimen from each subject determined no statistically significant difference in AUC between the manual quantification of the CRR (0.911 [0.882-0.935]) and the smartphone enabled calculation (0.923 [0.986-0.945], P=0.329) (FIG. 22C).

TABLE 5

Handling issues encountered in stage 3 of our study and solutions

| Issue * | Imaging issue | Effect | Remedy |
|---|---|---|---|
| 1 | Extreme viewpoint or perspective | Linear interpolation fails; wrong localization of patient cells | Warning message if opposing borders vary more than 10% (15° viewing angle); changed acquisition protocol to inclined background |
| 2 | Sheet not completely captured on image | Corners detection impossible | Error message upon missing corner; template position and orientation overlay on camera view |
| 3 | Non-uniform illumination and shadowing | Misclassification because of dark foreground | Warning message if high variance in illumination is detected |
| 4 | Reflection of water on, or near the sheet | Boundary and corner detection fails | Warning message suggesting inclined photographic surface to avoid puddle formation |
| 5 | Blurriness/Out-of-focus | The sheet is blurred | Blurring was neglected due to minor impact (tolerated up to Gaussian blur with sigma = 5) |

* listed in the order of decreasing frequency with which they were observed

CRR calculation. Analogues with the manual formula, the test result (CRR) is calculated as the ratio of average intensity of the dots on Pix1 to the average intensity of the dot in Pix2. The value of the blank sample (dots in the left upper cells position) is subtracted from all other calculated CRR values on the sheet.

Validation and Equivalence/Non-Inferiority Testing

Figure 23A:
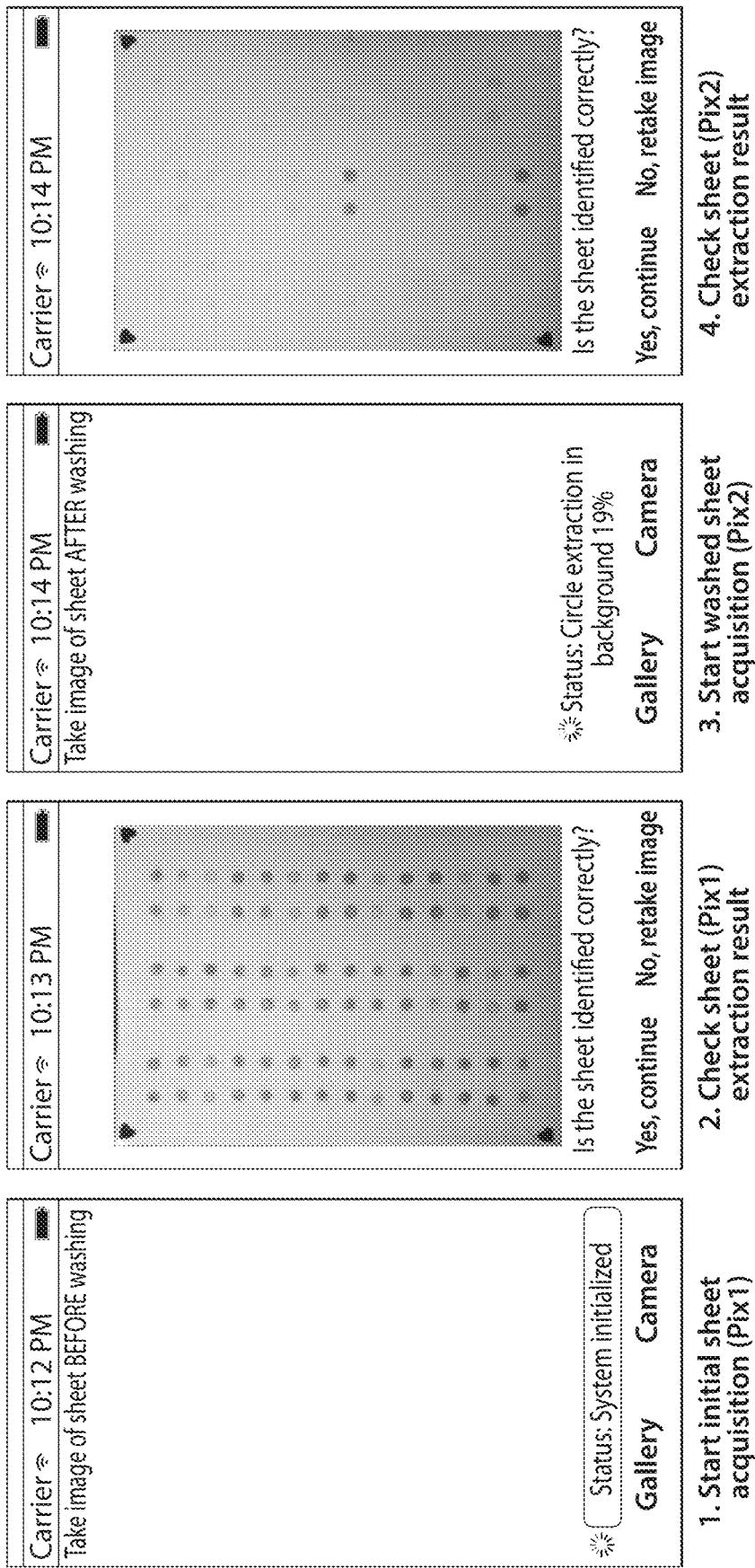
Figure 23B:
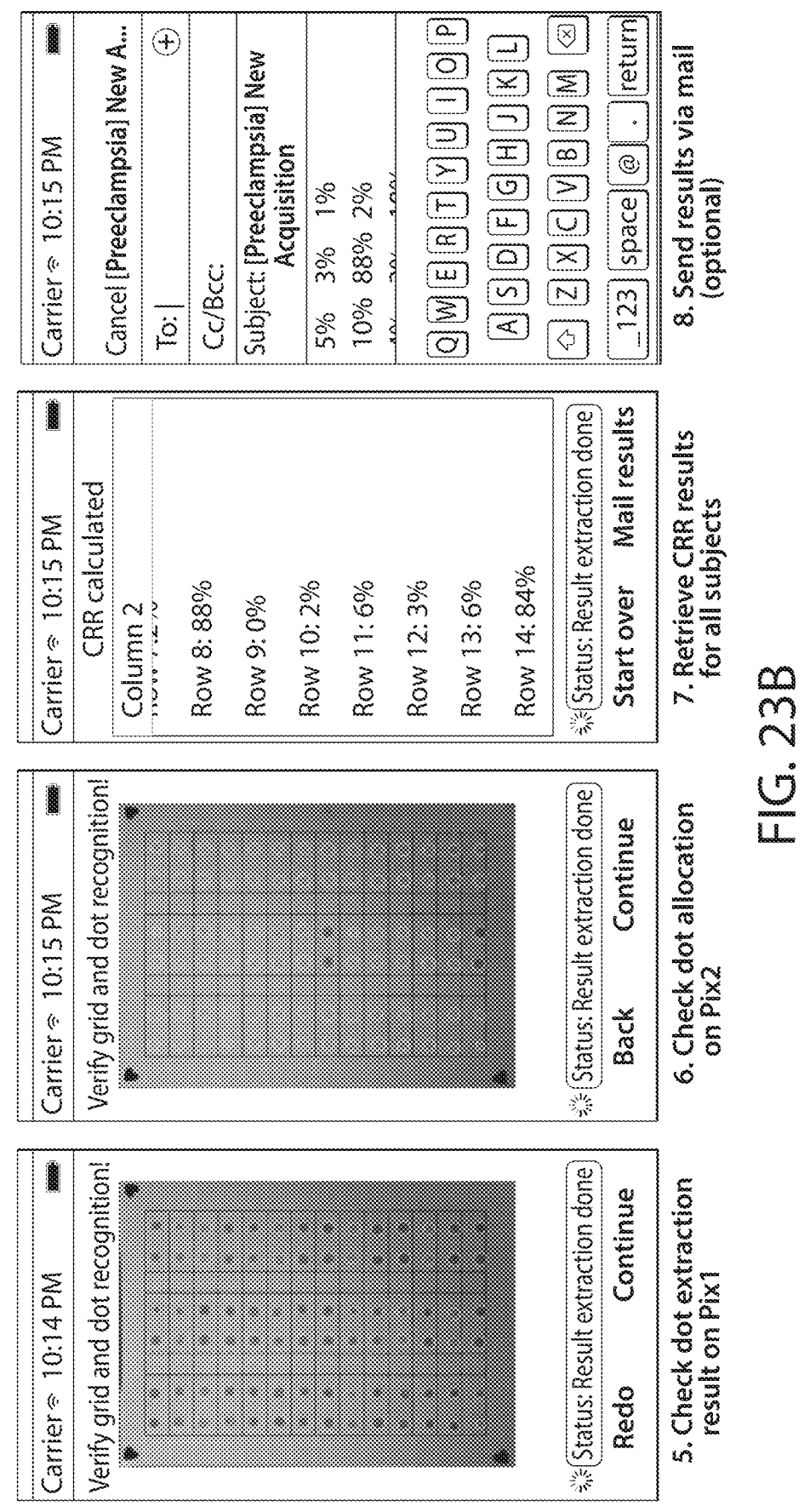

In stage 2, images were acquired and processed with an iPhone 4 and an application running the above sequence. For repeatability, the iPhone camera was used for acquisition, but the images then transferred to a computer where the processing was performed in an iPhone simulator. Eight CRD arrays containing 328 different urine specimens were analyzed as part of stage 2. These arrays were prepared specifically for this study from aliquots maintained frozen at −80° C. The specimens originated from 273 different women (55 specimens were subsequent collections at a time later in pregnancy). All specimens were consecutive with respect to specimen collection and storage. There was no overlap in specimens with those analyzed part of stage 1. The preva- Processing Time A screen by screen workflow of the iPhone app illustrating the processing time is included in FIG. 23 (in the shown example pictures Pix1 and Pix2 have been previously acquired and stored in the smartphone's picture library). Utilizing our image processing tool, the time from the conclusion of the "wet part" of the CRD test array to result was reduced to approximately 2 minutes of processing time on the smartphone.

Performance and Engineering Tolerance Analysis

To verify our algorithm and further improve the robustness our imaging protocol in stage 3 of our study, an additional dataset of 6 standardized CRD arrays was acquired. The experiments were performed by an untrained person who was also not given instruction on how to position the smartphone in order to acquire the images or avoid uneven illumination and shading (camera angle). This dataset helped to evaluate possible sources of operator-induced error. These handling issues are summarized in Table 5 along with their consequences on the imaging processing chain and remedies implemented in an updated version. The most often observed handling error was the excess perspective with which Pix1 and Pix2 were acquired. The majority of the issues were remedied through feedback to the user with instructions on how to reacquire the image in order to avoid the issue. The robustness of our imaging chain was further improved by setting a limit on the level of uneven illumination tolerated on Pix1 and Pix2. The user was prompted through the interface to retake the picture and move away from the light source when the shading exceeded the tolerance level in variance (coefficient of variation >15%).

Additional Optimizations of the Wet Part of the CRD Test

As part of stage 3, additional arrays were performed on a consecutive set of 94 urine samples comparing the previously validated "wet part" of the CRD test with two abbreviated versions: one omitting urine protein normalization and the other omitting both protein normalization and the 1-hour agitation with Congo Red. Omitting both urine normalization and agitation (samples mixed with Congo Red were placed immediately on the sheet) resulted in acceptable concordance (Lin's p=0.914 [0.873-0.942]) with the original protocol. In multivariate linear regression, the degree of bias was solely determined by the CRR level and not by position on the sheet, operator proficiency or urine protein concentration. Accuracy (Cb=0.997) exceeded precision (Pearson's p=0.916), suggesting that although the numbers may vary slightly, omitting normalization will not significantly affect the disease classification. Other experiments were carried out to replace methanol washing with alternatives easier to procure and dispose of. Through trial and error we determined that pharmacy grade isopropanol (90%) proved more effective than methanol and shortened the washing time (measured until complete blank decolorization) to 7 min. Pharmacy grade ethanol (70%) was not suitable as a methanol substitute. Denaturing agents (namely acetone, added in the U.S. to make it undrinkable) affected pore size in the nitrocellulose sheet which resulted in unacceptable loss of signal on positive samples.

Statistical Procedures

MedCalc software (v 12.5 Ostend, Belgium) was used as statistical aid unless otherwise specified. Correlations were tested using the Pearson's product moment correlation while agreement was determined using Lin's concordance coefficient and the McBride descriptive scaling of agreement. Equivalence/non-inferiority testing was performed in Microsoft Excel using the TOST/XLSTAT add-ins procedure. Multivariate stepwise linear regression was used to determine the impact of multiple variables on the level of bias (difference between the result obtained using the manual method and result after systematic elimination of steps in the wet protocol). Variables were entered in the model if P<0.05 and removed if P>0.1. For all procedures a P<0.05 was used to denote statistical significance. Equations $$L(x, y) = 0.3 \times R(x, y) + 0.59 \times G(x, y) + 0.11 \times B(x, y) \quad \text{(Equation 1)}$$

with $L(x,y)$ being the luminance, and $R(x,y)$, $G(x,y)$, and $B(x,y)$ determine the red, green, and blue values of the pixel at position x,y, respectively.

$$r(d_i) = \frac{\sum_{x,y \in d_i} L(x, y)}{N_{d_i}} - \frac{\sum_{(x,y) \in c_i, (x,y) \notin d_i} L(x, y)}{N_{c_i} - N_{d_i}} \quad \text{(Equation 2)}$$

with $r(d_i)$ being the normalized luminance (regarded as "redness") of dot $d_i$, $c_i$ the cell containing dot $d_i$, and N the number of pixels in $c_i$ or $d_i$.

References (Each of which is Incorporated by Reference Herein)

1. S. Lunde, in *Wipro*. (Wipro Ltd), vol. 2013.
2. C. Free et al., The effectiveness of M-health technologies for improving health and health services: a systematic review protocol. *BMC research notes* 3, 250 (2010).
3. M. Fiordelli, N. Diviani, P. J. Schulz, Mapping mHealth research: a decade of evolution. *Journal of medical Internet research* 15, e95 (2013).
4. E. Ozdalga, A. Ozdalga, N. Ahuja, The smartphone in medicine: a review of current and potential use among physicians and students. *Journal of medical Internet research* 14, e128 (2012).
5. A. Hart, K. Tallevi, D. Wickland, R. E. Kearney, J. A. Cafazzo, A contact-free respiration monitor for smart bed and ambulatory monitoring applications. *Conference proceedings: . . . Annual International Conference of the IEEE Engineering in Medicine and Biology Society. IEEE Engineering in Medicine and Biology Society. Conference* 2010, 927 (2010).
6. J. M. Ruano-Lopez et al., The SmartBioPhone, a point of care vision under development through two European projects: OPTOLABCARD and LABONFOIL. *Lab on a chip* 9, 1495 (Jun. 7, 2009).
7. J. J. Oresko, H. Duschl, A. C. Cheng, A wearable smartphone-based platform for real-time cardiovascular disease detection via electrocardiogram processing. *IEEE transactions on information technology in biomedicine: a publication of the IEEE Engineering in Medicine and Biology Society* 14, 734 (May, 2010).
8. K. Boehret, in All Things Reviewed. (http://allthingsd.com/20130813/device-nags-you-to-sit-up-straight/, 2013), vol. accessed Oct. 18, 2013.
9. H. Engel et al., Remote real-time monitoring of free flaps via smartphone photography and 3G wireless Internet: a prospective study evidencing diagnostic accuracy. *Microsurgery* 31, 589 (November, 2011).
10. E. Jonathan, M. Leahy, Investigating a smartphone imaging unit for photoplethysmography. *Physiological measurement* 31, N79 (November, 2010).
11. R. A. Joundi, J. S. Brittain, N. Jenkinson, A. L. Green, T. Aziz, Rapid tremor frequency assessment with the iPhone accelerometer. *Parkinsonism & related disorders* 17, 288 (May, 2011).
12. R. Lemoyne, T. Mastroianni, M. Cozza, C. Coroian, W. Grundfest, Implementation of an iPhone as a wireless accelerometer for quantifying gait characteristics. *Conference proceedings: . . . Annual International Conference of the IEEE Engineering in Medicine and Biology Society. IEEE Engineering in Medicine and Biology Society. Conference* 2010, 3847 (2010).
13. R. Lemoyne, T. Mastroianni, M. Cozza, C. Coroian, W. Grundfest, Implementation of an iPhone for characterizing Parkinson's disease tremor through a wireless accelerometer application. *Conference proceedings: . . . Annual International Conference of the IEEE Engineering in Medicine and Biology Society. IEEE Engineering in Medicine and Biology Society. Conference* 2010, 4954 (2010).
14. J. A. Wolf et al., Diagnostic inaccuracy of smartphone applications for melanoma detection. *JAMA dermatology* 149, 422 (April, 2013).

15. I. A. Buhimschi et al., Protein misfolding, urine congophilia, oligomeric state immunoreactivity and defective amyloid precursor protein processing in preeclampsia. *Manuscript in review.*
26. I. A. Buhimschi et al., Proteomic profiling of urine identifies specific fragments of SERPINA1 and albumin as biomarkers of preeclampsia. *American journal of obstetrics and gynecology* 199, 551 e 1 (November, 2008).
17. W. Gottesman, N. Baum, QR codes: next level of social media. *The Journal of medical practice management: MPM* 28, 345 (May-June, 2013).
18. N. Otsu, A threshold selection method from gray-level histograms. *IEEE Transactions on Systems, Man, and Cybernetics* 9, 62 (1979).
19. P. V. C. Hough, Machine Analysis of Bubble Chamber Pictures. *Proc. Int. Conf. High Energy Accelerators and Instrumentation*, (1959).
20. T. M. Lehmann, Gönner. C., Spitzer, K., Interpolation methods in medical image processing. *IEEE Trans Med Imaging* 18, 1049(1999).
21. O. Duda, P. E. Hart, Use of the Hough transformation to detect lines and curves in pictures. *Communications of Association for Computing Machinery* 15, 11 (1972).
22. L. I. Lin, A concordance correlation coefficient to evaluate reproducibility. *Biometrics* 45, 255 (March, 1989).
23. G. B. McBride, A proposal for strength-of-agreement criteria for Lin's Concordance Correlation Coefficient. *NIWA Client Report HAM* 2005-062, (2005).
24. E. Walker, A. S. Nowacki, Understanding equivalence and noninferiority testing. *Journal of general internal medicine* 26, 192 (February, 2011).
25. A. A. Okunad, V. X. Murthy, Technology as a 'major driver' of health care costs: a cointegration analysis of the Newhouse conjecmre. *Journal of health economics* 21, 147 (January, 2002).
26. A. F. Coskun, R. Nagi, K. Sadeghi, S. Phillips, A. Ozcan. Albumin testing in urine using a smart-phone. *Lab on a chip* 13, 4231 (Nov. 7, 2013).
27. S. Adibi, Mobile health (mHealth) biomedical imaging paradigm. *Conference proceedings: . . . Annual International Conference of the IEEE Engineering in Medicine and Biology Society. IEEE Engineering in Medicine and Biology Society. Conference* 2013, 6453 (July, 2013).
28. A. Labrique, L. Vasudevan, L. W. Chang, G. Mehl, H_pe for mHealth: more "y" or "o" on the horizon? *International journal of medical informatics* 82, 467 (May, 2013).
29. ACOG practice bulletin. Diagnosis and management of preeclampsia and eclampsia. Number 33, January 2002. American College of Obstetricians and Gynecologists. (2002).
30. K. S. Khan, D. Wojdyla, L. Say, A. M. Gulmezoglu, P. F. Van Look, WHO analysis of causes of maternal death: a systematic review. *Lancet* 367, 1066 (Apr. 1, 2006).
31. R. J. Guidotti, D. (2005).
32. F. Schoonjans, A. Zalata, C. E. Depuydt, F. H. Comhaire, MedCalc: a new computer program for medical statistics. *Computer methods and programs in biomedicine* 48, 257 (December, 1995).

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); and in yet another embodiment, to both A and B (optionally including other elements). Similarly, a reference to "A, B and/or C", when used in conjunction with open-ended language such as "comprising" can refer, in some embodiments, to A only (optionally including elements other than B and C); in another embodiment, to B only (optionally including elements other than A and C); in yet another embodiment, to C only (optionally including elements other than C and C); in yet another embodiment, to A and B (optionally including other elements), to A and C (optionally including other elements), to B and C (optionally including other elements), or to A, B and C (optionally including other elements).

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in some embodiments, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements).

It should also be understood that, unless clearly indicated to the contrary, in any methods claimed herein that include more than one step or act, the order of the steps or acts of the method is not necessarily limited to the order in which the steps or acts of the method are recited.

All references, patents and patent applications disclosed herein are incorporated by reference with respect to the subject matter for which each is cited, which, in some cases, may encompass the entirety of the document.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

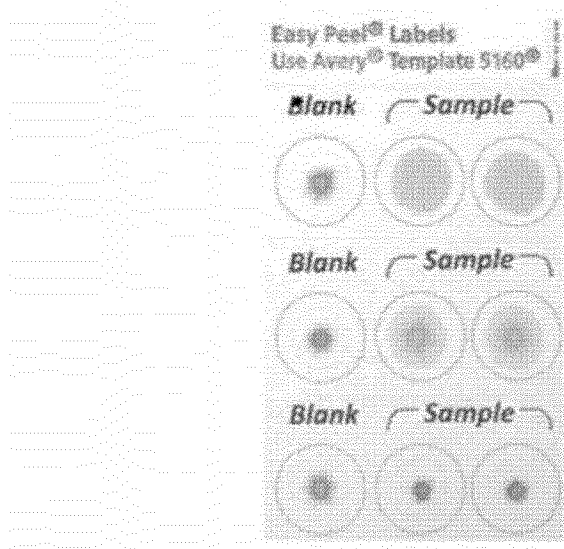

What is claimed is:

1. A method of detecting misfolded proteins in a biological sample obtained from a pregnant woman comprising: (a) applying a biological sample of a pregnant woman to a surface onto which a dye is adsorbed to produce a surface comprising a biological sample and the dye; (b) subjecting the surface to isoelectric focusing; and (c) determining the extent or rate of migration of the dye, wherein the extent or rate of migration of the dye is indicative of presence or absence of the misfolded proteins in the biological sample, such that the presence or absence of the misfolded proteins is detected.

2. The method of claim 1 further comprising the step of:
(d) comparing the extent or rate migration of the dye to a positive or negative control, wherein a difference in the extent or rate migration of the dye in comparison to the positive or negative control is indicative of misfolded proteins present in the biological sample.

3. The method of claim 1, wherein the dye is selected from the group consisting of sirius red F58 (CI 35780), benzo scarlet 4BNS (CI 29200), sirius scarlet GG (CI 40270), orange G, crystal violet Congo Red, Thioflavin S, Thioflavin T, Evans Blue, Trypan blue, amino-8-napthalene sulfonate (ANS) and bis-azo ANS.

4. The method of claim 3, wherein the dye is Congo Red.

5. The method of claim 1, wherein the surface is porous.

6. The method of claim 5, wherein the surface is a gel or a bead.

7. The method of claim 6, wherein the gel comprises agarose.

8. The method of claim 6, wherein the bead comprises agarose.

9. The method of claim 1, wherein the biological sample is urine.

10. The method of claim 2, wherein the biological sample is urine.

11. The method of claim 2, wherein the negative control is selected from the group consisting of (a) urine that does not comprise misfolded proteins, (b) saline and (c) phosphate buffered saline.

12. The method of claim 2, wherein the positive control is selected from the group consisting of (a) urine that comprises misfolded proteins and (b) Alzheimer's Disease brain tissue lysate.

13. The method of claim 2, wherein if the extent or rate migration of the dye is equal to or less than the negative control, the misfolded proteins are not present in the biological sample.

14. The method of claim 2, wherein if the extent or rate migration of the dye is equal to or greater than the positive control, the misfolded proteins are present in the biological sample.

15. The method of claim 14, wherein if the misfolded proteins are present in the biological sample, the pregnant woman has, or is at risk of having, preeclampsia.

16. The method of claim 2, wherein if the extent or rate migration of the dye is less than the positive control, the misfolded proteins are absent from the biological sample.

17. The method of claim 2, wherein the dye intercalates with the misfolded proteins.

18. The method of claim 17, wherein the dye is Congo Red.

19. The method of claim 17, wherein the misfolded proteins are selected from the group consisting of Serpina-1, albumin, IgG, kappa-free light chain, ceruloplasmin, interferon-inducible protein 6-16 (IFI6), amyloid precursor protein (APP) and combinations thereof.

20. The method of claim 1, wherein the mammal is a woman.

* * * * *

UNITED STATES PATENT AND TRADEMARK OFFICE
CERTIFICATE OF CORRECTION

PATENT NO. : 11,953,505 B2
APPLICATION NO. : 17/361967
DATED : April 9, 2024
INVENTOR(S) : Irina Buhimschi et al.

It is certified that error appears in the above-identified patent and that said Letters Patent is hereby corrected as shown below:

On the Title Page

Under Abstract Line 10 should read - 19 Claims, 44 Drawing Sheets -, as shown on the attached Title Page.

In the Claims

At Column 72, Claim 20, on Lines 34-35 should be canceled.

Signed and Sealed this
Third Day of September, 2024

Katherine Kelly Vidal
Director of the United States Patent and Trademark Office

CERTIFICATE OF CORRECTION (continued)

(12) United States Patent
Buhimschi et al.

(10) Patent No.: US 11,953,505 B2
(45) Date of Patent: Apr. 9, 2024

(54) METHODS AND COMPOSITIONS FOR DETECTING MISFOLDED PROTEINS

(71) Applicant: Yale University, New Haven, CT (US)

(72) Inventors: Irina Buhimschi, Columbus, OH (US); Catalin S. Buhimschi, Columbus, OH (US); Michael Choma, Hamden, CT (US); Hemant Tagare, North Haven, CT (US); Stephan Michael Jonas, Alsdorf (DE)

(73) Assignee: Yale University, New Haven, CT (US)

( * ) Notice: Subject to any disclaimer, the term of this patent is extended or adjusted under 35 U.S.C. 154(b) by 113 days.

(21) Appl. No.: 17/361,967

(22) Filed: Jun. 29, 2021

(65) Prior Publication Data
US 2022/0043001 A1 Feb. 10, 2022

Related U.S. Application Data

(60) Continuation of application No. 16/406,942, filed on May 8, 2019, now Pat. No. 11,079,392, which is a
(Continued)

(51) Int. Cl.
G01N 33/52 (2006.01)
C09B 69/10 (2006.01)
(Continued)

(52) U.S. Cl.
CPC .......... *G01N 33/689* (2013.01); *G01N 33/52* (2013.01); *G01N 33/6839* (2013.01);
(Continued)

(58) Field of Classification Search
CPC .. G01N 33/689; G01N 33/52; G01N 33/6839; G01N 21/78; G01N 2800/368; G01N 33/68; C09B 69/106
See application file for complete search history.

(56) References Cited

U.S. PATENT DOCUMENTS 4,444,879 A 4/1984 Foster et al.
5,998,216 A 12/1999 O'Donnell
(Continued)

FOREIGN PATENT DOCUMENTS

CN 102483415 A 5/2012
CN 103012599 A 4/2013
(Continued)

OTHER PUBLICATIONS

International Search Report and Written Opinion for International Application No. PCT/US2009/005957 dated May 26, 2010.
(Continued)

*Primary Examiner* — Jennifer Wecker
*Assistant Examiner* — Ali Husain Faraz
(74) *Attorney, Agent, or Firm* — Wolf, Greenfield & Sacks, P.C.

(57) ABSTRACT

Various aspects and embodiments of the present disclosure are directed to methods and compositions (e.g., kits) for the identification of subjects with misfolded proteins in their urine. For example, methods and compositions for determining that a urine sample from a pregnant woman contains or does not contain misfolded are provided. In some embodiments, the presence of misfolded proteins in a urine sample from a pregnant woman is an indication of preeclampsia.

19 Claims, 44 Drawing Sheets

Specification includes a Sequence Listing.